US009598418B2

(12) United States Patent
Srivastava et al.

(10) Patent No.: US 9,598,418 B2
(45) Date of Patent: Mar. 21, 2017

(54) SUBSTITUTED PHTHALAZIN-1 (2H)-ONE DERIVATIVES AS SELECTIVE INHIBITORS OF POLY (ADP-RIBOSE) POLYMERASE-1

(71) Applicant: CADILA HEALTHCARE LIMITED, Ahmedabad, Gujarat (IN)

(72) Inventors: Brijesh K. Srivastava, Gujarat (IN); Ranjit C. Desai, Gujarat (IN); Pankaj R. Patel, Gujarat (IN)

(73) Assignee: Cadila Healthcare Limited, Gujarat (IN)

( * ) Notice: Subject to any disclaimer, the term of this patent is extended or adjusted under 35 U.S.C. 154(b) by 0 days.

(21) Appl. No.: 14/647,088

(22) PCT Filed: Dec. 23, 2013

(86) PCT No.: PCT/IN2013/000794

§ 371 (c)(1),
(2) Date: May 23, 2015

(87) PCT Pub. No.: WO2014/102817

PCT Pub. Date: Jul. 3, 2014

(65) Prior Publication Data

US 2015/0291603 A1 Oct. 15, 2015

(30) Foreign Application Priority Data

Dec. 31, 2012 (IN) ......................... 3742/MUM/2012

(51) Int. Cl.

| | |
|---|---|
| ***C07D 498/04*** | (2006.01) |
| ***C07D 487/04*** | (2006.01) |
| ***C07D 237/32*** | (2006.01) |
| ***C07D 491/048*** | (2006.01) |
| ***C07D 495/04*** | (2006.01) |
| ***C07D 513/04*** | (2006.01) |
| ***C07D 403/10*** | (2006.01) |

(52) U.S. Cl.

CPC ......... *C07D 487/04* (2013.01); *C07D 237/32* (2013.01); *C07D 403/10* (2013.01); *C07D 491/048* (2013.01); *C07D 495/04* (2013.01); *C07D 498/04* (2013.01); *C07D 513/04* (2013.01)

(58) Field of Classification Search

CPC .................................................... C07D 237/32

See application file for complete search history.

(56) References Cited

U.S. PATENT DOCUMENTS

| | | | |
|---|---|---|---|
| 2005/0059663 | A1 | 3/2005 | Martin et al. |
| 2008/0269234 | A1 | 10/2008 | Gandhi et al. |

FOREIGN PATENT DOCUMENTS

| | | |
|---|---|---|
| WO | 2007/138351 | 12/2007 |
| WO | 2008/083027 | 7/2008 |
| WO | 2009/004356 | 1/2009 |
| WO | 2009/063244 | 5/2009 |
| WO | 2009/093032 | 7/2009 |
| WO | 2012/019426 | 2/2012 |
| WO | 2012/019427 | 2/2012 |
| WO | 2012/071684 | 6/2012 |

OTHER PUBLICATIONS

International Search Report issued in PCT/IN2013/000794, dated Apr. 28, 2014 (7 pages).

*Primary Examiner* — Paul V Ward

(74) *Attorney, Agent, or Firm* — Nixon & Vanderhye P.C.

(57) ABSTRACT

The present invention relates to novel compounds of general formula (I), their stereoisomers, regioisomers, tautomeric forms and novel intermediates involved in their synthesis, their pharmaceutically acceptable salts, pharmaceutically acceptable solvates and pharmaceutical compositions containing them. The present invention also relates to a process of preparing novel compounds of general formula (I), their stereoisomers, regioisomers, their tautomeric forms, their pharmaceutically acceptable salts, pharmaceutically acceptable solvates, pharmaceutical compositions containing them, and novel intermediates involved in their synthesis.

(I)

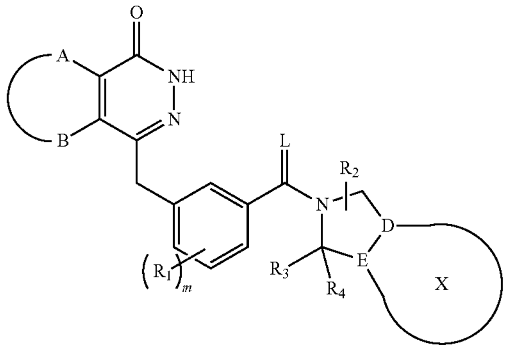

15 Claims, No Drawings

SUBSTITUTED PHTHALAZIN-1 (2H)-ONE DERIVATIVES AS SELECTIVE INHIBITORS OF POLY (ADP-RIBOSE) POLYMERASE-1

This application is a U.S. National Phase Entry of International Application No. PCT/IN2013/000794, filed Dec. 23, 2013, which designated the U.S. and claimed the benefit of Indian Application No. 3742/MUM/2012, filed Dec. 31, 2012. The entire contents of each of the above-identified applications are hereby incorporated herein by reference.

FIELD OF THE INVENTION

The present invention relates to novel compounds of general formula (I), their stereoisomers, regioisomers, tautomeric forms and novel intermediates involved in their synthesis, their pharmaceutically acceptable salts, pharmaceutically acceptable solvates and pharmaceutical compositions containing them. The present invention also relates to processes for preparing the novel compounds of general formula (I), their stereoisomers, regioisomers, their tautomeric forms, their pharmaceutically acceptable salts, pharmaceutically acceptable solvates, pharmaceutical compositions containing them, and novel intermediates involved in their synthesis.

(I)

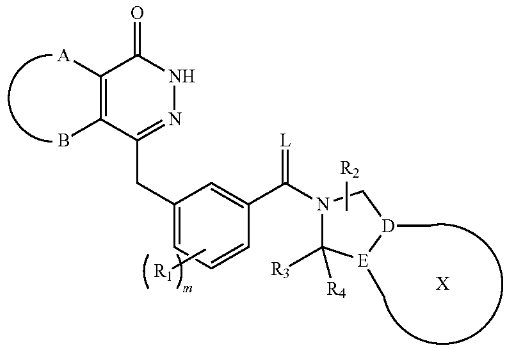

The present invention is further directed to compounds which cause selective inhibition of the poly (ADP-ribose) polymerase-1.

BACKGROUND & PRIOR ART

Exploitation of synthetic lethal relationship is a trustworthy therapeutic strategy to target genetic differences between tumor and normal cells which eventually provide large therapeutic window for the treatment of cancer. Poly (ADP-ribose) polymerase-1(PARP-1, 113 kDa) is a prototype member of the 17 member PARP protein superfamily. PARP-1 is a nuclear protein whose zinc finger DNA binding domain localizes PARP-1 to the site of DNA damage. This NAD dependent enzyme catalyzes poly (ADP-ribosylation) of proteins, involved in the detection and repair of DNA damage. It plays a frontal role in the decision of a cell to live or to die in a stress situation [Senthil kumar B., Rajmohan, et al., *Mol. Cell. Biol.* 2009, 29(15), 4116-4129]. The primary structure of the enzyme is highly conserved in eukaryotes with human enzyme having 92% homology with mouse enzyme at the level of amino acid sequence and a 50 amino acid block showing 100% homology between vertebrates [Virag Laszlo and Szabo Csaba, *Pharmacol. Reviews* 2002, 54(3), 375-429]. Studies on the molecular mechanism of PARP-1 suggests that, it is involved in various DNA related functions including gene amplifications, cell division, differentiation, apoptosis, DNA base excision repair and also effects on telomere length and chromosome stability [d'Add di Fagogna et al., *Nature Gen.* 1999, 23(10), 76-80].

It has been reported that PARP-1 modulates DNA repair and other processes and can produce long chains of poly (ADP-ribose) within the cell nucleus which is central to its activity [Althaus, F. R.; Richter, *C. Mol. Biol., Biochem. Biophys.* 1987, 37, 1-237]. Different studies on knock out mouse models, report that the deletion of PARP-1 impairs DNA repair but is not embryonically lethal. Double knock out PARP-1 and PARP-2 mice die during early embryogenesis, which shows that PARP-2 as the closest homolog of PARP-1 (62% identical in its catalytic domain to PARP-1) & plays a major role in the DNA repair during the absence of PARP-1 enzyme [Ratnam Kapil and Law Jenifer A. *Clin. Cancer Res.* 2007, 17(5), 1383-1388]. A group of scientists from Newcastle University and University of Konstanz, in *British Journal of Cancer* 2009, 101(2), 256-26, claims to be the first to directly compare PARP-1 polymorphisms, cellular levels of PARP-1 protein and PARP activity in a systematic way and reveals that PARP activity depends on other factors beside the level of protein and the active site SNP.

In a recent review from *Free Radical Biology & Medicine* 2009, 47, 13-26 suggests that PARP inhibitors could be used not only as chemo/radiotherapy sensitizers, but also as single agents to selectively kill cancers which are due to defect in DNA repair, specifically cancers with mutations in the breast cancer-associated gene (BRCA1 and BRCA2). PARP becomes activated in response to oxidative DNA damage and depletes cellular energy pools, thus leading to cellular dysfunction in various tissues. The activation of PARP may also induce various cell death processes and promotes an inflammatory response associated with multiple organ failure.

Recently some of the investigators have demonstrated in *Biochem. Pharmacol.* 2009, 77, 1348-1357 that PARP inhibitors combined with DNA-damage inducing cytostatic agents like taxol can lead to effective tumor therapy through activation of PI-3-kinase-Akt pathway.

The American Society of Clinical Oncology held its Annual Meeting in Orlando, Fla. (May 29-Jun. 2, 2009) and as reported in *Eur. J. Cancer* 2009, 45, 1897-1901 that two drugs Olaparib and BSI-201 from a new class of targeted agents called poly (ADP-ribose) polymerase (PARP) inhibitors have demonstrated significant activity against hard-to treat breast cancers, according to findings from two separate phase II trials.

Several small molecules that specifically target PARP-1 enzyme as an inhibitor are being investigated and among them BSI 201 (BiPar) is in Phase III clinical trial and AG 14699 (Cancer Res. UK), AZD 2281 (KuDOS), ABT 888 (Abbott) are in Phase II clinical trial, with promising initial results. However, special attention must be paid to the possibility that enhanced therapeutic efficacy might be accompanied by increased off-target effects because of effect on DNA-repair mechanism in normal tissues.

Recent findings have thrust poly(ADP-ribose) polymerases (PARPs) into the limelight as potential chemotherapeutic targets as described in *Nature Reviews Cancer* 4 Mar. 2010, 1-9. Crystal Structure of the Catalytic Domain of Human PARP2 in Complex with PARP Inhibitor ABT-888 reported by [Herwig Schuler et al., *Pharmacol. Biochemistry* 2010, 49, 1056-1058]

Novel compounds which are selective PARP-1 inhibitors, their preparation and their use in medicine have also been reported in WO 2002036576, WO 2006039545, WO 2007062413, WO 2004080976, WO 2009093032, WO 2008047082, WO 2001042219, WO 2005066163, WO 2006106326, WO 2008146035, WO 2006021801, US 20090192156, WO 2012019427, WO 2012071684, WO 2012019426, WO 2012072033, which are incorporated as references in their entirety.

Synthesis of pthalazinone derivatives of the following general formula and having the potential to inhibit PARP for the treatment of cancer or for potentiating tumor cells for the treatment with ionizing radiation or chemotherapeutic agents has been disclosed in US 2009/0192156 A1 and WO 2009/093032 A1.

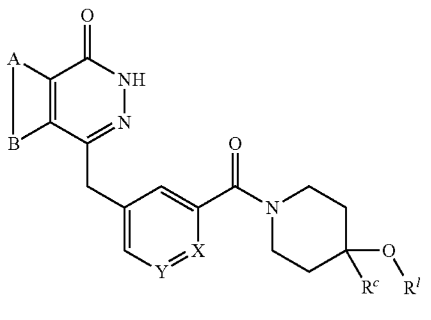

Synthesis of thiophene carboxamide class of compounds as the combination of CHK and PARP inhibitors for the treatment of cancer is disclosed in WO 2008146035 A1 and WO 2005066163 A2. Representative compounds have the following general formula,

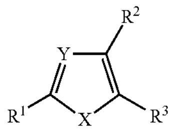

Wherein X is selected from NH, S and O. Y is selected from CH or N.

Crystalline form and improved method for the synthesis of particular pthalazinone derivatives and use of the crystalline form as PARP-1 inhibitor has been reported in WO 2008047082. Representative compounds have the following structure:

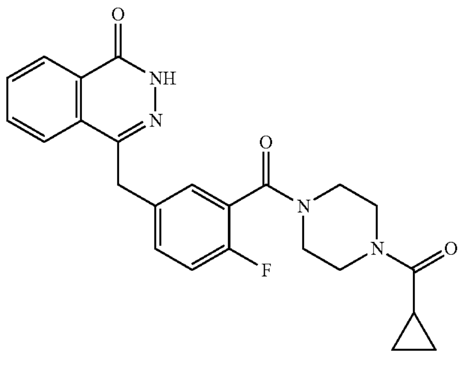 [SMILES: O=C(c1cc(Cc2n[nH]c(=O)c3ccccc23)ccc1F)N1CCN(C(=O)C2CC2)CC1]

Synthesis of 4-heteroarylmethyl substituted pthalazinone derivatives has been disclosed in WO 2006021801 A1 and WO 2004080976 A1 for use in treating cancer or other diseases ameliorated by the inhibition of PARP.

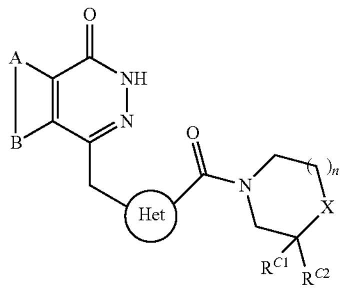

wherein, A and B together represent an optionally substituted, fused aromatic ring; X can be $NR^X$ or $CR^XR^Y$; If $X{=}NR^X$ then n is 1 or 2 and if $X{=}CR^XR^Y$ then n is 1; $R^X$ is selected from the group consisting of H, optionally substituted $C_{1-20}$ alkyl, $C_{1-20}$ aryl, $C_{(3-20)}$ heterocyclyl, thioamido, ester, acyl, and sulfonyl groups; $R^Y$ is selected from H, hydroxyl, amino; $R^X$ and $R^Y$ may together form a spiro $C_{3-7}$ cycloalkyl or heterocyclyl group; $R^{C1}$ and $R^{C2}$ are independently selected from the group consisting of H and $C_{1-4}$ alkyl; $R^1$ is selected from H and halo; And Het is selected from

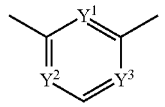

where $Y^1$ is selected from CH and N, $Y^2$ is selected from CH and N, $Y^3$ is selected from CH, CF and N, where one or two of $Y^1$, $Y^2$, and $Y^3$ can be N; and

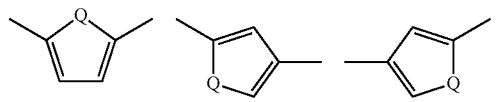

wherein Q is O or S.

Optimization of Phenyl-Substituted Benzimidazole Carboxamide Poly(ADP-Ribose) 5-Benzamidoisoquinolin-1-ones and 5-(ω-Carboxyalkyl)isoquinolin-1-ones as Isoform-Selective Inhibitors of Poly(ADP-ribose) Polymerase 2 (PARP-2) has been described in *J. Med. Chem.* 2011, 54, 2049-2059 by Peter T. Sunderland et. al.

Tumor Growth Inhibition by Olaparib in BRCA2 Germline-Mutated Patient-Derived Ovarian Cancer Tissue Xenografts has been recently published in *Clin Cancer Res* 2011, 17, 783-791.

Simultaneous determination of ABT-888, a poly (ADP-ribose) polymerase inhibitor, and its metabolite in human plasma by liquid chromatography/tandem mass spectrometry has been described in *Journal of Chromatography B,* 2011, 878, 333-339.

"Evolution of Poly(ADP-ribose)Polymerase-1 (PARP-1) inhibitors, From Concept to Clinic" a review article by Dana V. Ferraris has been published in *J. Med. Chem.* 2010, 53, 4561-4584, which describes in details of the efforts by different pharmaceutical industries and academic institutions in the development of the PARP 1 inhibitors.

“Development of substituted 6-[4-fluoro-3-(piperazin-1-ylcarbonyl)benzyl]-4,5-dimethylpyridazin-3-(2H)-ones as potent poly(ADP-ribose)polymerase-1 (PARP-1) inhibitors active in BRCA deficient cells” article has been published by Federica Ferrigno et al. in *Bioorg. Med. Chem. Lett.* 2010, 20, 1100-1105.

‘Polymerase Inhibitors: Identification of (S)-2-(2-Fluoro-4-(pyrrolidin-2-yl)phenyl)-1H-benzimidazole-4-carboxamide (A-966492), a highly Potent and Efficacious Inhibitor’ has been described in *J. Med. Chem.*, 2010, 53, 3142-3153.

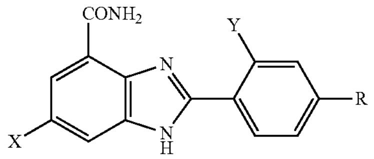

Design, synthesis of Quinoline-8-carboxamides, a new class of Poly (adenosine-diphosphate-ribose) polymerase-1 (PARP-1) Inhibitor has been described in *J. Med. Chem.* 2009, 52, 868-877. Synthesis of 2-[(R)-2-methylpyrrolidin-2-yl]-1H-benzimidazole-4-carboxamide as a Poly (ADP-ribose) Polymerase (PARP) Inhibitor has been disclosed in *J. Med. Chem.* 2009, 52, 514-523.

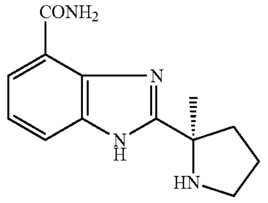 [SMILES: C[C@]1(c2nc3c(C(N)=O)cccc3[nH]2)CCCN1]

Synthesis of aminoethyl pyrrolo dihydroisoquinolinones as novel poly (ADP-ribose) polymerase-1 inhibitors has been described in *Bioorg. Med. Chem. Lett.* 2009, 19, 4042-4045. Representative compounds have the following general formula.

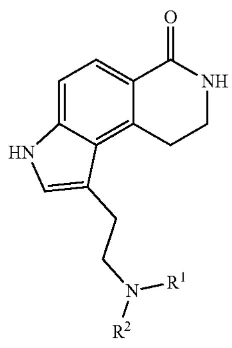

Synthesis of isoquinolinone-based tetracycles as poly (ADP-ribose) polymerase-1 (PARP-1) inhibitors has been described in *Bioorg. Med. Chem. Lett.* 2009, 19, 7537-7541. Representative compounds have the following general formula.

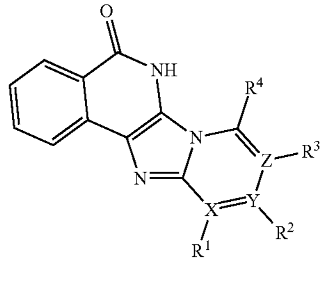

Identification of substituted pyrazolo[1,5-a]quinazolin-5(4H)-one as potent poly(ADP-ribose)polymerase-1 (PARP-1) inhibitors has been described in *Bioorg. Med. Chem. Lett.* 2009, 19, 4196-4200. Representative compounds have the following general formula

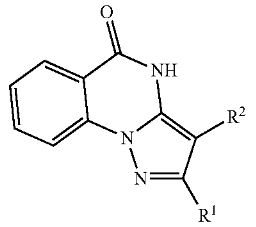

Synthesis of novel tricyclic quinoxalinone as the inhibitors of poly (ADP-ribose) polymerase-1 (PARP-1) has been stated in *Bioorg. Med. Chem. Lett.* 2009, 19, 4050-4054. Representative compounds have the following general formula.

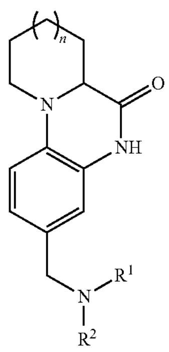

Identification of ring-fused pyrazolo pyridin-2-ones as novel poly (ADP-ribose) polymerase-1 inhibitors has been published in *Bioorg. Med. Chem. Lett.* 2008, 18, 5126-5129. This describes compounds of the following general formula.

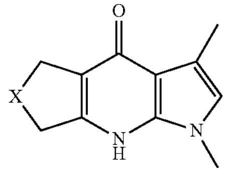 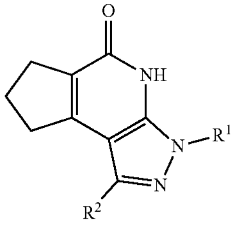

-continued

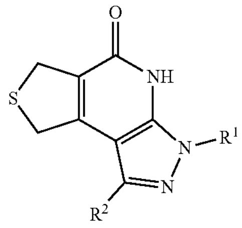

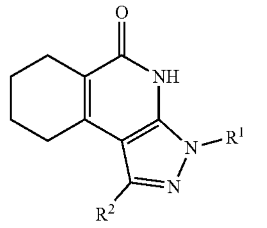

Discovery of Orally Active and Brain-Penetrable Quinoxalinone Inhibitors of Poly (ADP-ribose) polymerase has been disclosed in *J. Med. Chem.* 2004, 47, 4151-4154 and describes compounds of the following general formula.

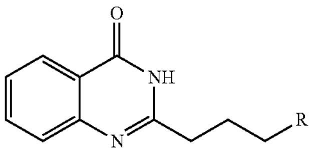

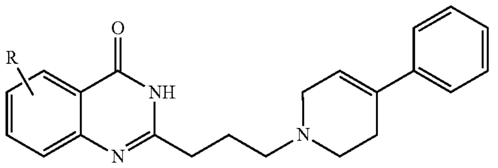

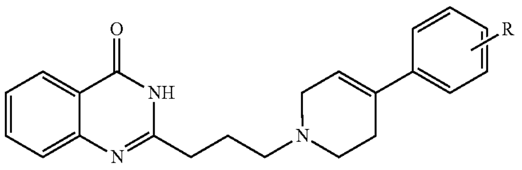

Discovery of potent Poly(ADP-ribose) Polymerase-1 Inhibitors from the modification of Indeno[1,2-c]isoquinolinone and the described compounds of the following general formula I has been reported in *J. Med. Chem.* 2005, 48, 5100-5103.

(1)

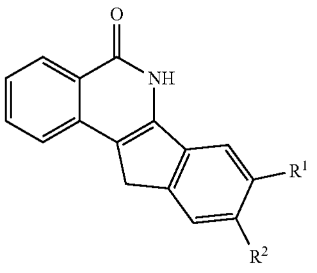

WO 2012 019426 discloses PARP inhibitors of the following general formula (I)

(I)

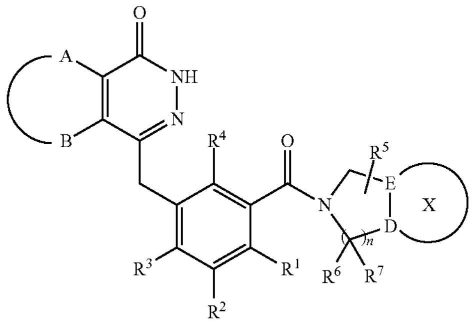

wherein: A and B are connected together to the carbon atoms to form a cycloalkyl group, heterocyclic group, aryl or heteroaryl group, Each of the ring atoms D or E is independently selected from C or N atoms; when n is 1, D and E are connected to one another to accomplish 6~10-membered ring X; This specification is incorporated as reference in its entirety.

WO 2012 072033 discloses compounds of formula I or II, their isomers, salts, solvates, chemically protected form, and prodrugs:

I

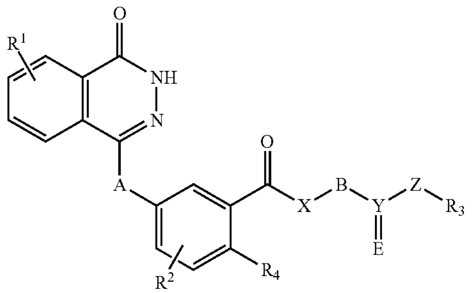

II

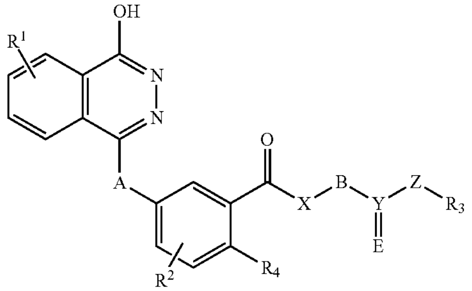

wherein the substituents are as defined in the specification which is incorporated in entirety as reference.

New Gen Therapeutics, Inc has published a patent WO 2012166983 and disclosed tricyclic inhibitors of poly(ADP-ribose)polymerase.

Substituted 4-(4-fluoro-3-(piperazine-1-carbonyl)benzyl) phthalazin-1(2H)-one derivatives as Poly (ADP-ribose) polymerase-1 inhibitors has been published in WO 2012014221 by Cadila Healthcare Ltd. and discloses the following general structure (I)

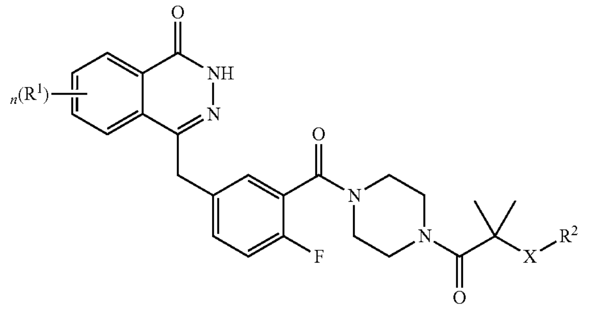

Shanghai Institute of Materia Medica, Chinese Academy of Science disclosed 2-Arylbenzofuran-7-formamide compounds preparation method and use thereof in patent WO 2013117120 and mentions the following formula:

(I)

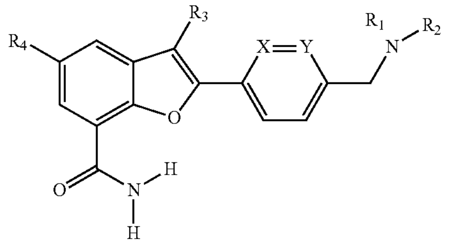

Merck disclosed tetrahydro-quinazolinone derivatives as tankyrase and PARP inhibitors in patent WO 2013/117288 and mentions the following general structure (I)

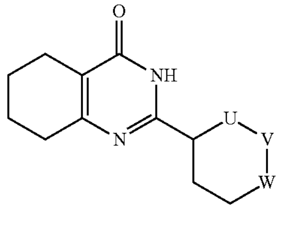

Novel compounds having PARP inhibitory activity has been disclosed by Santen Pharmaceutical Co. Ltd. in a patent WO 2013/008872 and the following formula has been disclosed.

(I)

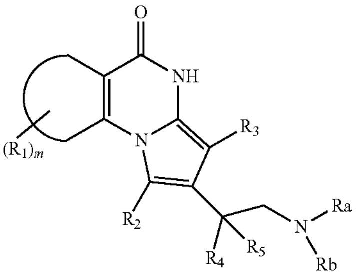

Fused tetra or penta-cyclic pyridophthalazinones as PARP inhibitors have been reported by Belgena, Ltd. in a patent WO 2013097226.

AstraZeneca AB has published a patent U.S. Pat. No. 8,475,842 for immediate release pharmaceutical formation of 4-[3-4(cyclopropanecarbonyl-piperazine-1-carbonyl)-4-fluoro-benzyl]-2H-phthalazin-1-one.

BioMarin recently published a patent US 2013/0053365 and disclosed the formula (M)

formula (M)

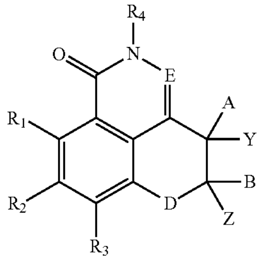

Though several compounds have been reported in the literature as PARP-I inhibitors, very few have actually shown actual clinical benefits and none have been approved so far. Looking at the large unmet medical needs, there appears a need for developing further compounds which have better safety and efficacy profile. We herein disclose a new series of compounds which shows potential as PARP-I inhibitors.

SUMMARY OF THE INVENTION

The present invention describes novel compounds useful as poly (ADP-ribose) polymerase-1 inhibitors. The compounds are defined by the general formula (I) below.

(I)

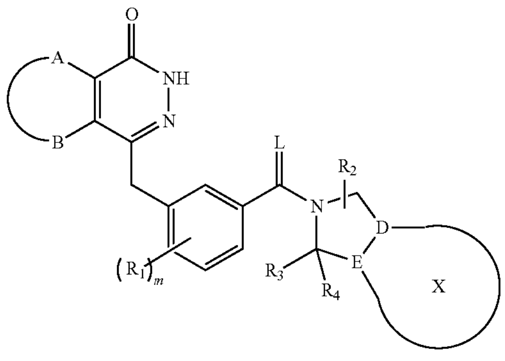

:

The compounds of the present invention acts by inhibiting PARP1 enzyme to prevent the process of DNA repair and induce cell mediated apoptosis. As a result of compromised repair, PARP-1 deficient or inhibited cells are more sensitive to DNA damaging agents (γ radiation, topoisomerase inhibitors, and alkylating agents). The compounds of the present invention are selective inhibitors of the poly (ADP-ribose) polymerase-1.

OBJECTS OF THE INVENTION

The main object of the present invention is to provide novel compounds of general formula (I), their stereoisomers, tautomeric forms, their regioisomers, novel intermediates involved in their synthesis, their pharmaceutically acceptable salts, their pharmaceutically acceptable solvates and pharmaceutical compositions containing them or their mixtures and their use in medicine.

(I)

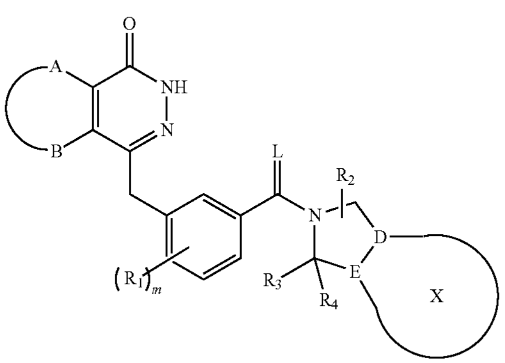

Another object of the present invention is provided a process for the preparation of novel compounds of general formula (I), their stereoisomers, regioisomers and their tautomeric forms, novel intermediates involved in their synthesis, pharmaceutically acceptable salts, pharmaceutically acceptable solvates and pharmaceutical compositions containing them.

Another object of the present invention is to provide a method of treatment of diseases which can be treated or whose symptoms can be reversed with by administering a therapeutically effective & non-toxic amount of the compound of formula (I) or their pharmaceutically acceptable compositions to the mammals.

DETAILED DESCRIPTION OF THE INVENTION

The compounds of the present invention are defined by the general formula (I) below:

(I)

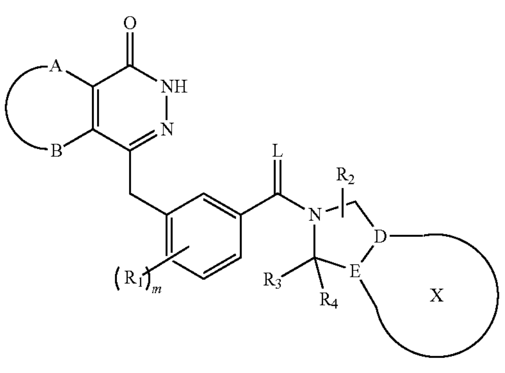

wherein 'A' and 'B' may be independently selected from hydrogen, alkyl or connected together to the carbon atoms to form a cycloalkyl, heterocyclyl, aryl or heteroaryl groups, wherein each of the said cycloalkyl, heterocyclyl, aryl or heteroaryl groups are further substituted independently by one or more substituent groups selected from alkyl, halogen, hydroxyl, alkoxy, cycloalkyl, heterocyclyl, aryl, heteroaryl, —C(O)OR$^5$, —OC(O)R$^5$, —O(CH$_2$)$_p$C(O)OR$^5$, —C(O)R$^5$, —NHC(O)R$^5$, —NR$^6$R$^7$, —OC(O)NR$^6$R$^7$ or —C(O)NR$^6$R$^7$ groups.

R$^1$ at each occurrence is independently selected from H, halogen, or the groups selected from (C$_1$-C$_{12}$)alkyl, haloalkyl, cycloalkyl, alkylthio or the group (OSO$_2$) alkyl, wherein each of these groups may be further substituted by suitable substituents selected from those disclosed hereinafter below; m=1-4;

L=—O, —S, —NH;

R$^2$ is selected from substituent groups consisting of hydrogen atom, hydroxyl, alkyl, cycloalkyl, oxo, C(O)OR$^5$, —C(O)R$^5$, or —C(O)NR$^6$R$^7$, wherein said alkyl or cycloalkyl group may be further substituted by one or more substituents groups selected from halogen, hydroxyl, alkyl or alkoxy.

R$^3$ and R$^4$ are each independently selected from the groups such as hydrogen atom, alkyl, hydroxyl, alkoxy, cycloalkyl, —C(O)OR$^5$, —OC(O)R$^5$, —O(CH$_2$)$_p$C(O)OR$^5$, —C(O)R$^5$, —NHC(O)R$^5$, —NR$^6$R$^7$, —OC(O)NR$^6$R$^7$ or —C(O)NR$^6$R$^7$; alternatively, R$^3$ and R$^4$ together form an oxo group;

Each of ring atoms 'D' and 'E' is independently selected from C or N atoms;

'D' and 'E' are connected to one another to form 5 membered ring 'X', wherein 'X' is selected from the groups such as cycloalkyl, heterocyclyl, heteroaryl, wherein the cycloalkyl, heterocyclyl or heteroaryl groups is further substituted with one or more substituents selected from alkyl, halogen, hydroxyl, alkoxy, cycloalkyl, heterocyclyl, aryl or heteroaryl, benzyl, oxo, OR$^5$, —C(O)OR$^5$, —OC(O)R$^5$, —O(CH$_2$)$_p$C(O)OR$^5$, C(O)R$^5$, S(O)$_n$R$^5$, —NHC(O)R$^5$, NR$^6$R$^7$, —OC(O)NR$^6$R$^7$ or —C(ONR$^6$R$^7$, wherein the alkyl, cycloalkyl, heterocyclyl, aryl, heteroaryl or benzyl are each independently substituted further with one or more substituents selected from alkyl, halogen, hydroxyl, alkoxy, cycloalkyl, heterocyclyl, aryl, heteroaryl, oxo, —C(O)OR$^5$, —OC(O)R$^5$, O(CH$_2$)$_p$C(O)OR$^5$, —C(O)R$^5$, —S(O)nR$^5$, —NHC(O)R$^5$, NR$^6$R$^7$, —OC(O)NR$^6$R$^7$ or —C(O)NR$^6$R$^7$ substituents;

R$^5$ at each occurrence is independently selected from hydrogen atom, alkyl, cycloalkyl, heterocyclyl, aryl or heteroaryl groups; wherein said alkyl, cycloalkyl, heterocyclyl, aryl or heteroaryl groups are each independently substituted by one or more substituents selected from alkyl, halogen, hydroxyl, alkoxy, cycloalkyl, heterocyclyl, aryl, heteroaryl, carboxylic acid or carboxylic acid ester substituents.

Each of R$^6$ or R$^7$ at each occurrence are independently selected from the groups consisting of hydrogen atom, alkyl, cycloalkyl, heterocyclyl, aryl or heteroaryl groups; wherein said alkyl, cycloalkyl, heterocyclyl, aryl or heteroaryl groups are each independently further substituted by one or more substituents selected from alkyl, halogen, hydroxyl, alkoxy, cycloalkyl, heterocyclyl, aryl, heteroaryl, carboxylic acid or carboxylic acid ester substituents;

Alternatively, R$^6$ and R$^7$ are joined together with nitrogen atom to form a heterocyclic ring; wherein said heterocyclic ring contains one or more heteroatoms selected from N, O, S(O)$_n$, furthermore the stated heterocyclic ring is further substituted with one or more substituents selected from alkyl, halogen, hydroxyl, alkoxy, cycloalkyl, heterocyclyl, aryl, heteroaryl, carboxylic acid or carboxylic acid ester substituted substituents;

n is 0, 1 or 2 and p is 0, 1 or 2.

Suitable substituents wherever applicable and where substituents are not specifically mentioned includes, but are not limited to the following radicals, alone or in combination with other radicals, hydroxyl, oxo, halo, thio, nitro, amino, alkyl, alkoxy, haloalkyl or haloalkoxy groups.

The preferred heterocycles representing

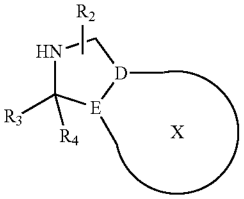

may be selected from the following bicyclic rings mentioned below

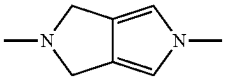, 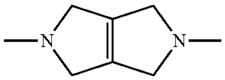,

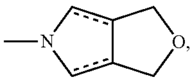, 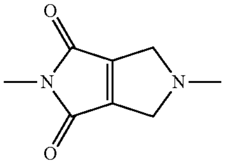,

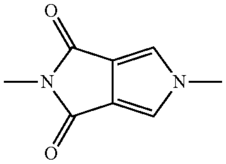 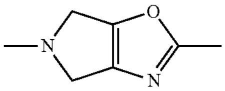,

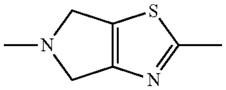, 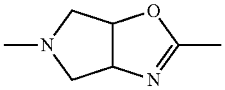,

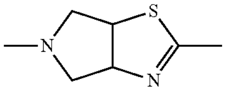 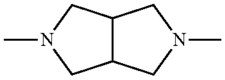,

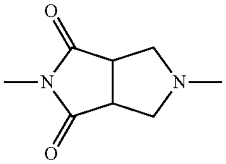, 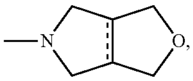,

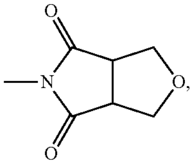, 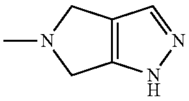

In another preferred embodiment, the groups representing the above may further be selected from those described hereinafter.

The "aryl" may be selected from phenyl, naphthyl, tetrahydronaphthyl, indenyl, dihydroindenyl, biphenyl groups and each of these groups may be optionally substituted with one or more substituents selected from hydrogen, halogen, alkyl, alkoxy, hydroxyl, haloalkyl, haloalkoxy, cyano, thioalkyl, cycloalkyl groups;

"Heteroaryl" or "heteroaromatic" is selected from suitable single or fused mono, bi or tricyclic aromatic heterocyclic radicals containing one or more hetero atoms selected from O, N or S, more preferably the groups are selected from pyridyl, thienyl, furyl, pyrrolyl, indolinyl, indolyl, pyridofuranyl, pyridothienyl, thienopyrimidyl, quinolinyl, pyrimidinyl, pyrazolyl, quinazolinyl, pyridazinyl, purinyl groups, each of these groups may be further optionally substituted with one or more substituents selected from hydrogen, halogen, alkyl, alkoxy, hydroxyl, haloalkyl, haloalkoxy, aryl, aralkyl, cyano, alkylthio, thioalkyl groups;

"Heterocyclyl" may be selected from suitable saturated, partially saturated or unsaturated aromatic or non-aromatic mono, bi or tricyclic radicals, containing one or more heteroatoms selected from nitrogen, sulfur and oxygen, more preferably selected from aziridinyl, azetidinyl, pyrrolidinyl, imidazolidinyl, piperidinyl, piperazinyl, 2-oxopiperidinyl, 4-oxopiperidinyl, 2-oxopiperazinyl, 3-oxopiperazinyl, morpholinyl, thiomorpholinyl, 2-oxomorpholinyl, azepinyl, diazepinyl, oxapinyl, thiazepinyl, oxazolidinyl, thiazolidinyl, dihydrothiophene, dihydropyran, dihydrofuran, dihydrothiazole, benzopyranyl, benzopyranonyl, benzodihydrofuranyl, benzodihydrothienyl, pyrazolopyrimidonyl, azaquinazolinoyl, thienopyrimidonyl, quinazolonyl, pyrimidonyl, benzoxazinyl, benzoxazinonyl, benzothiazinyl, benzothiazinonyl, thienopiperidinyl groups, each of these groups may be optionally substituted with one or more substituents selected from hydrogen, halogen, alkyl, alkoxy, hydroxyl, haloalkyl, haloalkoxy, aryl, aralkyl, cyano, alkylthio, thioalkyl groups;

In a further embodiment the groups, radicals described above may be selected from:

- the term"alkyl" used either alone or in combination with other radicals, denotes a linear or branched radical containing one to six carbons, selected from methyl, ethyl, n-propyl, iso-propyl, n-butyl, sec-butyl, tert-butyl, amyl, t-amyl, n-pentyl, n-hexyl, and the like;
- the term"alkoxy" used either alone or in combination with other radicals, is selected from groups containing an alkyl radical, as defined above, attached directly to an oxygen atom, more preferably groups selected from methoxy, ethoxy, n-propoxy, iso-propoxy, n-butoxy, t-butoxy, iso-butoxy, pentyloxy, hexyloxy, and the like;
- the term"haloalkyl" is selected from an alkyl radical, as defined above, suitably substituted with one or more halogens; such as fluoromethyl, difluoromethyl, trifluoromethyl, fluoroethyl, difluoroethyl, trifluoroethyl, mono or polyhalo substituted methyl, ethyl, propyl, butyl, pentyl or hexyl groups;
- "Haloalkoxy" is selected from suitable haloalkyl, as defined above, directly attached to an oxygen atom, more preferably groups selected from fluoromethoxy, chloromethoxy, fluoroethoxy, chloroethoxy and the like;
- the term "alkylthio" used either alone or in combination with other radicals, denotes a straight or branched or cyclic monovalent substituent comprising an alkyl group as defined above, linked through a divalent sulfur atom having a free valence bond from the sulfur atom, more preferably the groups may be selected from methylthio, ethylthio, propylthio;
- the term "aralkyl" represents an aryl group as defined above attached to an alkyl group as described above;

"Heteroaralkyl" and "heterocyclyclakyl" represents heteroaryl and heterocyclyl groups respectively as defined above attached to an alkyl group as defined above.

The compounds of formula (I) may optionally be converted to their suitable pharmaceutically acceptable salts by processes as are known in the art. The novel compounds of the present invention can further be formulated into suitable pharmaceutically acceptable compositions by combining with suitable excipients by techniques and processes and concentrations as are well known.

The compounds of the present invention modulate PARP-1 receptor and are useful as a therapeutic target for many diseases and especially for the treatment of cancer.

The compounds prepared according to present invention include, but are not limited to:

Example 1: 4-(3-(5-benzyloctahydropyrrolo[3,4-c]pyrrole-2-carbonyl)-4-fluorobenzyl)phthalazin-1(2H)-one;

Example 2: 2-benzyl-5-(2-fluoro-5-((4-oxo-3,4-dihydrophthalazin-1-yl)methyl) benzoyl)tetrahydropyrrolo[3,4-c]pyrrole-1,3(2H,3aH)-dione;

Example 3: 4-(4-fluoro-3-(1,4,5,6-tetrahydropyrrolo[3,4-c] pyrazole-5-carbonyl) benzyl)phthalazin-1 (2H)-one;

Example 4: 4-(3-(5-(cyclopropanecarbonyl)octahydropyrrolo[3,4-c]pyrrole-2-carbonyl)-4-fluorobenzyl) phthalazin-1(2H)-one;

Example 5: 4-(3-(1-(cyclopropylmethyl)-1,4,5,6-tetrahydropyrrolo[3,4-c]pyrazole-5-carbonyl)-4-fluorobenzyl) phthalazin-1(2H)-one;

Example 6: 4-(3-(5-(cyclopropylmethyl)octahydropyrrolo [3,4-c]pyrrole-2-carbonyl)-4-fluorobenzyl)phthalazin-1 (2H)-one;

Example 7: 4-(4-fluoro-3-(5-(2,2,2-trifluoroethyl)octahydropyrrolo[3,4-c]pyrrole-2-carbonyl)benzyl)phthalazin-1 (2H)-one;

Example 8: 4-(3-(5-(cyclopropylmethyl)-1,2,3,4,5,6-hexahydropyrrolo[3,4-c]pyrrole-2-carbonyl)-4-fluorobenzyl) phthalazin-1(2H)-one;

Example 9: 4-(3-(5-benzyloctahydropyrrolo[3,4-c]pyrrole-2-carbonyl)-4-fluorobenzyl)phthalazin-1(2H)-one hydrochloride;

Example 10: 4-(4-fluoro-3-(5-(2-((3-fluorophenyl)thio)-2-methylpropanoyl) octahydropyrrolo[3,4-c]pyrrole-2-carbonyl)benzyl)phthalazin-1(2H)-one;

Example 11: 2-benzyl-5-(2-fluoro-5-((4-oxo-3,4-dihydrophthalazin-1-yl)methyl) benzoyl)tetrahydropyrrolo[3,4-c]pyrrole-1,3(2H,3aH)-dione;

Example 12: 4-(3-(1-(cyclopropanecarbonyl)-1,4,5,6-tetrahydropyrrolo[3,4-c]pyrazole-5-carbonyl)-4-fluorobenzyl)phthalazin-1 (2H)-one;

Example 13: tert-butyl 5-(2-fluoro-5-((4-oxo-3,4-dihydrophthalazin-1-yl)methyl) benzoyl) hexahydropyrrolo [3,4-c]pyrrole-2(1H)-carboxylate;

Example 14: 4-(4-fluoro-3-(hexahydro-1H-furo[3,4-c]pyrrole-5-carbonyl) benzyl)phthalazin-1 (2H)-one;

Example 15: 4-(4-fluoro-3-(octahydropyrrolo[3,4-c]pyrrole-2-carbonyl) benzyl) phthalazin-1 (2H)-one;

Example 16: 4-(4-fluoro-3-(5-(methylsulfonyl)octahydropyrrolo[3,4-c]pyrrole-2-carbonyl)benzyl) phthalazin-1 (2H)-one;

Example 17: 4-(4-fluoro-3-(1-(methylsulfonyl)-1,4,5,6-tetrahydropyrrolo[3,4-c]pyrazole-5-carbonyl)benzyl) phthalazin-1 (2H)-one;

Example 18: 4-(3-(5-benzoyloctahydropyrrolo[3,4-c]pyrrole-2-carbonyl)-4-fluorobenzyl)phthalazin-1(2H)-one;

Example 19: 4-(3-(5-(2,4-difluorobenzyl)octahydropyrrolo [3,4-c]pyrrole-2-carbonyl)-4-fluorobenzyl) phthalazin-1 (2H)-one;

Example 20: 4-(3-(5,6-dihydro-4H-furo[3,4-c]pyrrole-5-carbonyl)-4-fluorobenzyl) phthalazin-1 (2H)-one;

Example 21: 4-(4-fluoro-3-(5-methyloctahydropyrrolo[3,4-c]pyrrole-2-carbonyl) benzyl)phthalazin-1 (2H)-one;

Example 22: 5-(2-fluoro-5-((4-oxo-3,4-dihydrophthalazin-1-yl)methyl)benzoyl) tetrahydropyrrolo[3,4-c]pyrrole-1,3 (2H,3aH)-dione;

Example 23: 4-(4-fluoro-3-(octahydrocyclopenta[c]pyrrole-2-carbonyl)benzyl) phthalazin-1 (2H)-one;

Example 24: 4-(4-fluoro-3-(5-(4-fluorobenzyl)octahydropyrrolo[3,4-c]pyrrole-2-carbonyl)benzyl) phthalazin-1 (2H)-one;

Example 25: 4-(4-fluoro-3-(5-(2-fluorobenzyl)octahydropyrrolo[3,4-c]pyrrole-2-carbonyl)benzyl) phthalazin-1 (2H)-one;

Example 26: 4-(4-fluoro-3-(5-(2-4-(4-fluoro-3-(5-((6-methoxypyridin-2-yl)methyl) octahydropyrrolo [3,4-c] pyrrole-2-carbonyl)benzyl)phthalazin-1(2H)-one;

Example 27: 5-(2-fluoro-5-((4-oxo-3,4-dihydrophthalazin-1-yl)methyl)benzoyl)-2-methyl tetrahydropyrrolo[3,4-c] pyrrole-1,3(2H,3aH)-dione;

Example 28: 4-(4-fluoro-3-(1-methyl-1,4,5,6-tetrahydropyrrolo[3,4-c]pyrazole-5-carbonyl)benzyl)phthalazin-1 (2H)-one compound with 4-(4-fluoro-3-(2-methyl-2,4,5,6-tetrahydropyrrolo[3,4-c]pyrazole-5-carbonyl)benzyl) phthalazin-1(2H)-one (1:3);

Example 29: 4-(3-(2,2-dioxido-3,4,5,6-tetrahydro-1H-thieno[3,4-c]pyrrole-5-carbonyl)-4-fluorobenzyl) phthalazin-1 (2H)-one;

Example 30: 4-(3-(5,6-dihydro-4H-thieno[3,4-c]pyrrole-5-carbonyl)-4-fluorobenzyl) phthalazin-1 (2H)-one;

Example 31: 4-(4-fluoro-3-(1,2,3,4,5,6-hexahydropyrrolo[3,4-c]pyrrole-2-carbonyl) benzyl)phthalazin-1 (2H)-one;

Example 32: 4-(4-fluoro-3-(5-phenyloctahydropyrrolo[3,4-c]pyrrole-2-carbonyl) benzyl)phthalazin-1 (2H)-one;

Example 33: 4-(4-fluoro-3-(5-methyl-1,2,3,4,5,6-hexahydropyrrolo[3,4-c]pyrrole-2-carbonyl)benzyl) phthalazin-1 (2H)-one;

Example 34: 4-(3-((3aR,8bR)-decahydropyrrolo[3,4-a]pyrrolizine-2-carbonyl)-4-fluorobenzyl)phthalazin-1(2H)-one;

Example 35: 4-(4-fluoro-3-(2-methyl-2,4,5,6-tetrahydropyrrolo[3,4-c]pyrazole-5-carbonyl)benzyl)phthalazin-1 (2H)-one;

Example 36: 4-(4-fluoro-3-(1-methyl-2,4,5,6-tetrahydropyrrolo[3,4-c]pyrazole-5-carbonyl)benzyl) phthalazin-1 (2H)-one;

Example 37: 2-((5-(2-fluoro-5-((4-oxo-3,4-dihydrophthalazin-1-yl)methyl) benzoyl) hexahydropyrrolo [3,4-c]pyrrol-2(1H)-yl)methyl)-6-methoxypyridine-1-oxide;

Example 38: 4-(3-(5-(difluoromethyl)octahydropyrrolo[3,4-c]pyrrole-2-carbonyl)-4-fluorobenzyl) phthalazin-1 (2H)-one;

Example 39: 4-(4-fluoro-3-((3aR,6aS)-5-oxooctahydrocyclopenta[c]pyrrole-2-carbonyl)benzyl) phthalazin-1 (2H)-one;

Example 40: Mixture of 1 & 2 Ethyl 4-(3-(2,4,5,6-tetrahydropyrrolo[3,4-c]pyrazole-5-carbonyl)-4-fluorobenzyl) phthalazin-1(2H)-one;

Example 41: 4-(3-(2-ethyl-2,4,5,6-tetrahydropyrrolo[3,4-c] pyrazole-5-carbonyl)-4-fluorobenzyl)phthalazin-1(2H)-one;

Example 42: 4-(3-(1-ethyl-1,4,5,6-tetrahydropyrrolo[3,4-c] pyrazole-5-carbonyl)-4-fluorobenzyl)phthalazin-1(2H)-one;

Example 43: 4-(4-fluoro-3-(1-isopropyl-1,4,5,6-tetrahydropyrrolo[3,4-c]pyrazole-5-carbonyl)benzyl) phthalazin-1(2H)-one;

Example 44: Mixture of (1 & 2 isopropyl) 4-(4-fluoro-3-(1,4,5,6-tetrahydropyrrolo [3,4-c]pyrazole-5-carbonyl)benzyl)phthalazin-1(2H)-one;

Example 45: 4-(4-fluoro-3-(2-isopropyl-2,4,5,6-tetrahydropyrrolo[3,4-c]pyrazole-5-carbonyl)benzyl) phthalazin-1(2H)-one;

Example 46: 4-(3-((3aR,6aS)-5,5-difluorooctahydrocyclopenta[c]pyrrole-2-carbonyl)-4-fluorobenzyl)phthalazin-1(2H)-one;

Example 47: 4-(4-fluoro-3-(5-(2-methoxyethyl)octahydropyrrolo[3,4-c]pyrrole-2-carbonyl)benzyl) phthalazin-1(2H)-one;

Example 48: N-((3 aR,6aS)-2-(2-fluoro-5-((4-oxo-3,4-dihydrophthalazin-1-yl)methyl) benzoyl)octahydrocyclopenta[c]pyrrol-5-yl)cyclopropanecarboxamide;

Example 50: 4-(4-fluoro-3-(1-methyl-2,4,5,6-tetrahydropyrrolo[3,4-c]pyrazole-5-carbonyl)benzyl) phthalazin-1(2H)-one hydrobromide;

Example 51: 4-(4-fluoro-3-(1-methyl-2,4,5,6-tetrahydropyrrolo[3,4-c]pyrazole-5-carbonyl)benzyl) phthalazin-1(2H)-one hydrochloride;

Example 52: 4-(4-fluoro-3-(1-methyl-1,4,5,6-tetrahydropyrrolo[3,4-c]pyrazole-5-carbonyl)benzyl) phthalazin-1(2H)-one sulfate;

Example 53: 4-(4-fluoro-3-(1-methyl-1,4,5,6-tetrahydropyrrolo[3,4-c]pyrazole-5-carbonyl)benzyl) phthalazin-1(2H)-one 4-methylbenzenesulfonate;

Example 53: 4-(4-fluoro-3-(1-methyl-1,4,5,6-tetrahydropyrrolo[3,4-c]pyrazole-5-carbonyl)benzyl) phthalazin-1(2H)-one benzenesulfonate;

Example 54: 5-(2-fluoro-5-((4-oxo-3,4-dihydrophthalazin-1-yl)methyl)benzoyl)-2-isopropyl-2,4,5,6-tetrahydropyrrolo[3,4-c]pyrazol-2-ium hydrogensulfate;

Example 55: 4-(3-(1-cyclopropyl-1,4,5,6-tetrahydropyrrolo[3,4-c]pyrazole-5-carbonyl)-4-fluorobenzyl) phthalazin-1(2H)-one;

Suitable groups and substituents on the groups may be selected from those described anywhere in the specification.

The compounds of the present invention may be prepared using the methods described below, together with conventional techniques known to those skilled in the art of organic synthesis, or variations thereon as appreciated by those skilled in the art. Referred methods include, but are not limited to those described below, where all symbols are as defined earlier.

The compounds of the present invention can be prepared according to the following schemes 1

Scheme 1:

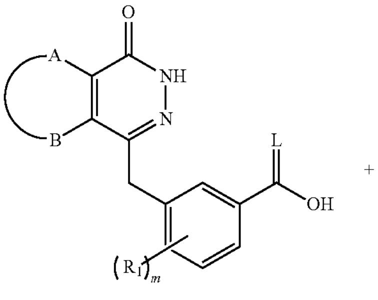

(II)

-continued

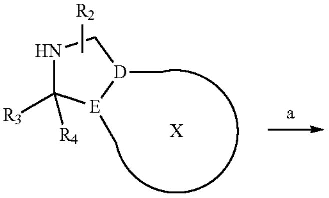

(III)

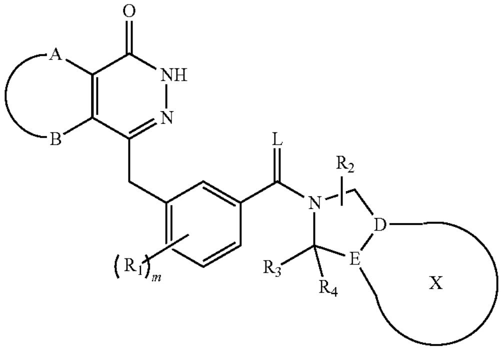

(I)

[a]Reagents and conditions: , DMF, TBTU, triethylamine, 0-27° C., 2-6 h

Synthesis of Compound of General Formula (I)

General Process of Preparation:

The Compounds of the general formula (II) can be synthesized by processes reported for e.g. in *J. Med. Chem.* 2008, 51, 6581-6591 with suitable modifications/alterations as required which are within the skills of a skilled person.

Compounds of the general formula (I) can be synthesized by coupling the compounds of the general formula (III) with the compounds of the general formula (II), using suitable coupling agents such as O-(Benzotriazol-1-yl)-N,N,N',N'-tetramethyluronium-tetrafluoroborate (TBTU), dimethylaminopyridine (DMAP), dicyclohexylcarbodiimide (DCC), hydroxybenzotriazole ($HOBt.H_2O$), and 1-Ethyl-3-(3-dimethylaminopropyl) carbodiimide hydrochloride (EDC. HCl) & the like in the presence of organic bases such as DIPEA, TEA, pyridine, & the like in the solvents such as tetrahydrofuran, dimethyl formamide, dichloromethane, chloroform & the like or their suitable mixtures at ambient temperature.

The invention is further exemplified by the following non-limiting examples which are provided for exemplifying the invention and should not be construed as limiting the scope of the invention in any ways. It will be appreciated that the other embodiments which are not exemplified can be easily practiced by a skilled person using his routine skills after reading the specific examples provided below. Such changes/alterations/modifications etc. which may be required to practice the full scope of the invention as described and claimed in the present invention are well within the scope of a person skilled in the art.

Unless otherwise specified, 1H NMR spectral data given in the examples are recorded using a 400 MHz spectrometer (Bruker Topspin 2.0) and reported in δ scale. Tetra methyl silane is used as the internal standard.

EXAMPLE 1

Synthesis of 4-(3-(5-benzyloctahydropyrrolo[3,4-c]pyrrole-2-carbonyl)-4-fluorobenzyl)phthalazin-1(2H)-one

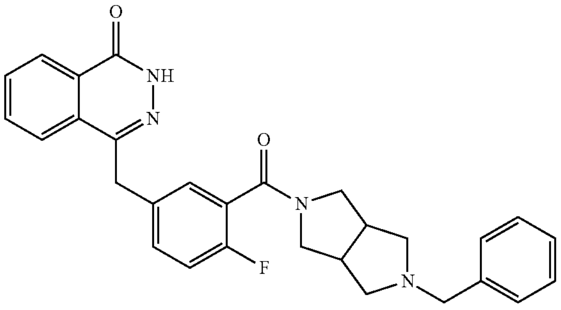 [SMILES: O=C(c1cc(Cc2n[nH]c(=O)c3ccccc23)ccc1F)N1CC2CN(Cc3ccccc3)CC2C1]

To a solution of 2-fluoro-5-((4-oxo-3,4-dihydrophthalazin-1-yl)methyl)benzoic acid (1 g, 3.35 mmol) in dry DMF (15 mL) was added TBTU (1.292 g, 4.02 mmol) at room temperature under atmosphere of nitrogen. To this 2-benzyloctahydropyrrolo[3,4-c]pyrrole (0.678 g, 3.35 mmol) and DIPEA (1.32 mL, 6.71 mmol) were added. The reaction mixture was stirred at room temperature for 2 h. The progress of reaction was checked by TLC by using mobile phase 5% methanol in chloroform. The reaction mixture was diluted with ethyl acetate. The organic layer was washed with water, dried over anhydrous $Na_2SO_4$ and solvents were evaporated on a rotatory evaporator under reduced pressure to crude solid which was purified by the flash column chromatography using eluent chloroform:methanol (97:3) to afford 4-(3-(5-benzyloctahydropyrrolo[3,4-c]pyrrole-2-carbonyl)-4-fluorobenzyl) phthalazin-1(2H)-one as white solid (1.19 g, 74%).

$^1$H-NMR (400 MHz, DMSO-$d_6$) δ 12.59 (s, 1H), 8.25 (dd, J=7.6 Hz & 0.6 Hz, 1H), 7.94(d, J=7.6 Hz, 1H), 7.86-7.80 (m, 2H), 7.35 (m, 1H), 7.32 (dd, 1H), 5.29-7.24 (m, 4H), 7.23-7.20 (m, 2H), 4.32 (s, 2H), 3.63 (m, 1H), 3.47 (m, 1H), 3.46 (m, 2H), 3.36 (m, 1H), 2.9 (dd, 1H), 2.60-2.8 (m, 3H), 2.51-2.49 (m, 2H), 2.1 (m, 1H).

EXAMPLE 2

2-benzyl-5-(2-fluoro-5-((4-oxo-3,4-dihydrophthalazin-1-yl)methyl)benzoyl) tetrahydropyrrolo[3,4-c]pyrrole-1,3(2H,3aH)-dione

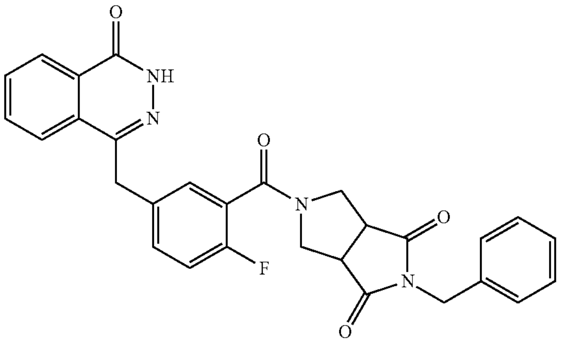 [SMILES: O=C(c1cc(Cc2n[nH]c(=O)c3ccccc23)ccc1F)N1CC2C(=O)N(Cc3ccccc3)C(=O)C2C1]

$^1$H-NMR (400 MHz, DMSO-$d_6$) δ 12.59 (s, 1H), 8.25 (d, J=7.6 Hz, 1H), 7.80-7.89(m, 3H), 7.41-7.43 (m, 1H), 7.13-7.40 (m, 7H), 4.55 (s, 2H), 4.26 (s, 2H), 4.15-4.17 (brd, 1H), 3.50-3.62 (m, 4H), 3.37-3.40 (brd, 1H).

EXAMPLE 3

4-(4-fluoro-3-(1,4,5,6-tetrahydropyrrolo[3,4-c]pyrazole-5-carbonyl)benzyl) phthalazin-1 (2H)-one

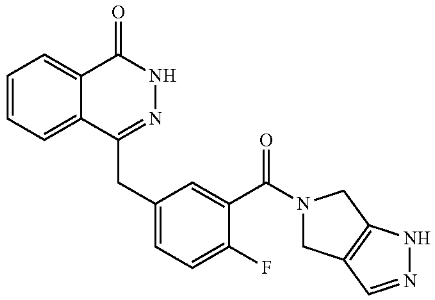 [SMILES: O=C(c1cc(Cc2n[nH]c(=O)c3ccccc23)ccc1F)N1Cc2cn[nH]c2C1]

$^1$H-NMR (400 MHz, DMSO-$d_6$) δ 12.74 (s, 1H), 12.58 (s, 1H), 8.25 (d, J=7.6 Hz, 1H), 7.97 (dd, J=8 & 3.6 Hz, 1H), 7.80-7.90 (m, 2H), 7.42-7.59 (m, 3H), 7.25 (t, J=9 Hz, 1H), 4.56 (s, 2H), 4.35 (s, 2H), 4.25-4.29 (brd, 2H).

EXAMPLE 4

4-(3-(5-(cyclopropanecarbonyl) octahydropyrrolo[3,4-c]pyrrole-2-carbonyl)-4-fluorobenzyl) phthalazin-1(2H)-one

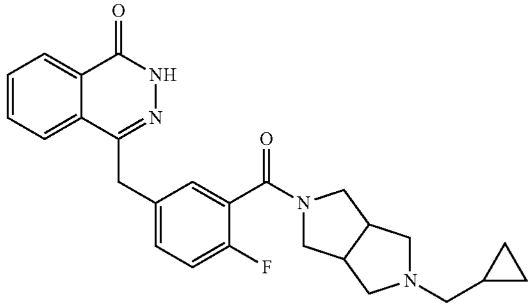

$^1$H-NMR (400 MHz, DMSO-$d_6$) δ 12.59 (s, 1H), 8.24 (d, J=1.2 Hz, 1H), 7.96 (dd, J=8 & 4.8 Hz, 1H), 7.82-7.90 (m, 2H), 7.40 (dd, J=6.8 & 5.2 Hz, 2H), 7.23 (dd, J=9.6 & 3.6 Hz, 2H), 4.32 (s, 2H), 3.89-3.90 (brt, 1H), 3.70-3.80 (m, 1H), 3.50-3.60 (m, 1H), 3.40-3.49 (m, 2H), 3.22-3.26 (m, 2H), 3.11-3.16 (m, 2H), 2.90-3.0 (m, 1H), 1.17-1.25 (m, 1H), 0.69-0.72 (brt, 4H).

EXAMPLE 5

4-(3-(1-(cyclopropylmethyl)-1,4,5,6-tetrahydropyrrolo[3,4-c]pyrazole-5-carbonyl)-4-fluorobenzyl) phthalazin-1(2H)-one

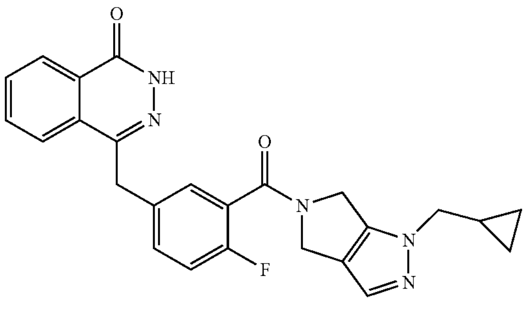 [SMILES: O=C(c1cc(Cc2n[nH]c(=O)c3ccccc23)ccc1F)N1Cc2cnn(CC3CC3)c2C1]

1H NMR (400 MHz, DMSO-d6): δ 12.77 (brs, 1H), 8.30 (d, J=7.6 Hz, 1H), 8.03 (dd, J=7.6 & 4.8 Hz, 1H), 7.83-7.91 (m, 2H), 7.46-7.58 (m, 3H), 7.24-7.29 (brt, 1H), 4.57 (s, 2H), 4.37 (s, 2H), 4.25-4.29 (brd, 2H), 4.0 (d, J=7.2 Hz, 2H), 1.12-1.19 (m, 1H), 0.35-0.47 (m, 4H).

EXAMPLE 6

4-(3-(5-(cyclopropylmethyl)octahydropyrrolo[3,4-c]pyrrole-2-carbonyl)-4-fluorobenzyl)phthalazin-1(2H)-one

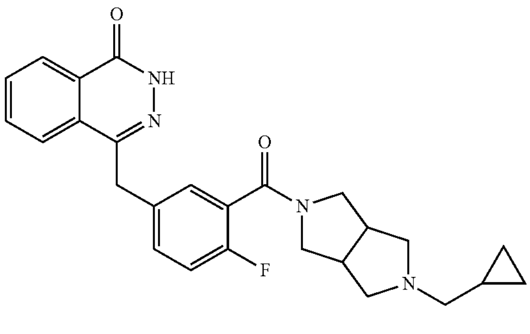

1H NMR (400 MHz, CDCl3): δ 10.30 (s, 1H), 8.44-8.47 (m, 1H), 7.70-7.79 (m, 3H), 7.35 (dd, J=6.4 & 2.4 Hz, 1H), 7.26-7.31 (m, 1H), 7.0-7.05 (brt, 1H), 4.27 (s, 2H), 3.75-3.76 (brd, 2H), 3.45-3.47 (m, 1H), 2.88-3.24 (m, 4H), 2.36-2.52 (m, 5H), 0.98 (brs, 1H), 0.56-0.58 (brd, 2H), 0.19-0.58 (brd, 2H).

EXAMPLE 7

4-(4-fluoro-3-(5-(2,2,2-trifluoroethyl)octahydropyrrolo[3,4-c]pyrrole-2-carbonyl) benzyl)phthalazin-1(2H)-one

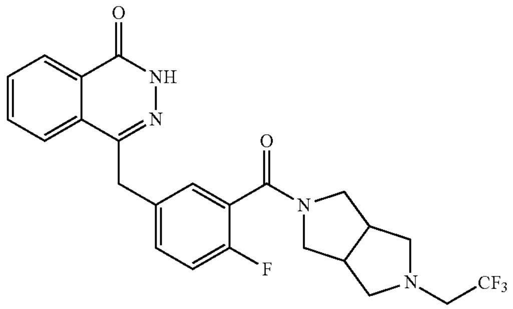 [SMILES: O=C(c1cc(Cc2n[nH]c(=O)c3ccccc23)ccc1F)N1CC2CN(CC(F)(F)F)CC2C1]

1H NMR (400 MHz, In CDCl3): δ 10.28 (s, 1H), 8.45-8.47 (m, 1H), 7.70-7.77 (m, 3H), 7.36 (dd, J=6.4 & 2.4, 1H), 7.26-7.29 (m, 1H), 6.99-7.04 (m, 1H), 4.27 (s, 2H ), 3.86-3.91 (m, 1H), 3.61-3.65 (m, 1H), 3.48-3.53 (m, 1H), 3.15-3.19 (m, 1H), 3.0-3.07 (m, 1H), 2.86-2.99 (m, 1H), 2.69-2.82 (m, 3H), 2.50-2.53 (m, 1H)

EXAMPLE 8

4-(3-(5-(cyclopropylmethyl)-1,2,3,4,5,6-hexahydropyrrolo[3,4-c]pyrrole-2-carbonyl)-4-fluorobenzyl) phthalazin-1(2H)-one

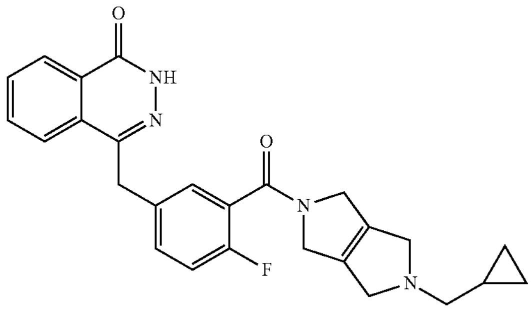 [SMILES: O=C(c1cc(Cc2n[nH]c(=O)c3ccccc23)ccc1F)N1CC2=C(CN(CC3CC3)C2)C1]

1H NMR (400 MHz, DMSO-d6): δ 12.59 (s, 1H), 8.27-8.25 (m, 1H), 7.97 (d, J=7.6 Hz, 1H), 7.91-7.87 (m, 1H), 7.83 (dd, J=7.6 Hz & 1.2 Hz, 1H), 7.42 (dd, J=10.4 Hz & 5.2 Hz, 2H), 7.26-7.22 (m, 1H), 4.32 (s, 2H), 4.23 (s, 2H), 3.92 (s, 2H), 3.78-3.46 (m, 3H), 3.42 (s, 1H), 2.69-2.66 (m, 1H), 1.0-0.7 (m, 1H), 0.5-0.035 (m, 2H), 0.2 (m, 2H).

EXAMPLE 9

4-(3-(5-benzyloctahydropyrrolo[3,4-c]pyrrole-2-carbonyl)-4-fluorobenzyl)phthalazin-1(2H)-one hydrochloride

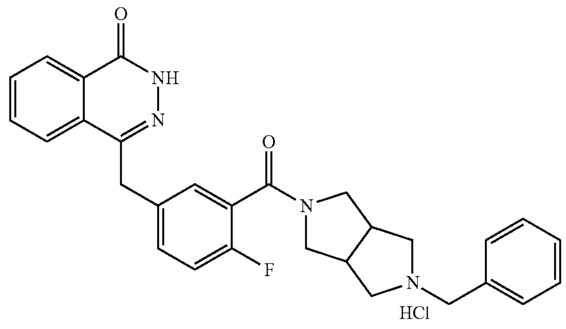 [SMILES: O=C(c1cc(Cc2n[nH]c(=O)c3ccccc23)ccc1F)N1CC2CN(Cc3ccccc3)CC2C1 ; Cl]

1H NMR (400 MHz, DMSO-d6): δ 12.62 (s, 1H), 10.81 (s, 1H), 8.26 (m, 1H), 8.32-7.98 (m, 1H), 7.87-7.61 (m, 1H), 7.59 (dd, 1H), 7.53 (dd, 1H), 7.44 (m, 4H), 7.38-7.35 (m, 1H), 7.27-7.19 (m, 1H), 4.39-4.31 (m, 4H), 3.72 (d, 1H), 3.28 (m, 1H), 3.16 (m, 2H), 2.99-2.89 (m, 2H), 2.73-2.49 (m, 2H).

EXAMPLE 10

4-(4-fluoro-3-(5-(2-((3-fluorophenyl)thio)-2-methylpropanoyl)octahydropyrrolo[3,4-c]pyrrole-2-carbonyl)benzyl)phthalazin-1(2H)-one

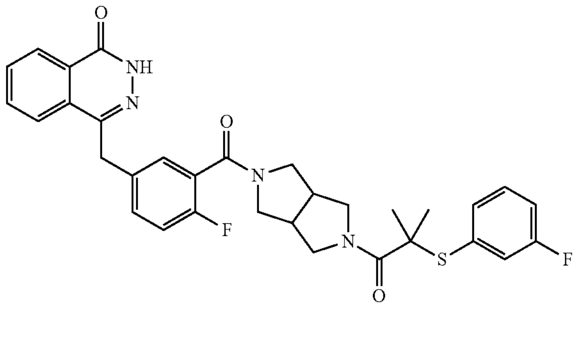 [SMILES: CC(C)(Sc1cccc(F)c1)C(=O)N1CC2CN(C(=O)c3cc(Cc4n[nH]c(=O)c5ccccc45)ccc3F)CC2C1]

1H NMR (400 MHz, DMSO-d6): δ 12.58 (s, 1H), 8.25 (d, J=6.4 Hz, 1H), 7.90 (d, 1H), 7.88 (t, 1H), 7.82 (t, 1H), 7.37 (d, J=6.4 Hz, 1H), 7.34 (m, 2H), 7.19 (t, 2H), 7.1 (m, 2H), 4.45 (d, 2H), 4.39 (t, 4H), 4.30 (s, 2H), 3.43-3.36 (m, 3H), 3.17 (d, 2H), 1.4 (s, 6H).

EXAMPLE 11

2-benzyl-5-(2-fluoro-5-((4-oxo-3,4-dihydrophthalazin-1-yl)methyl)benzoyl) tetrahydropyrrolo[3,4-c]pyrrole-1,3(2H,3aH)-dione

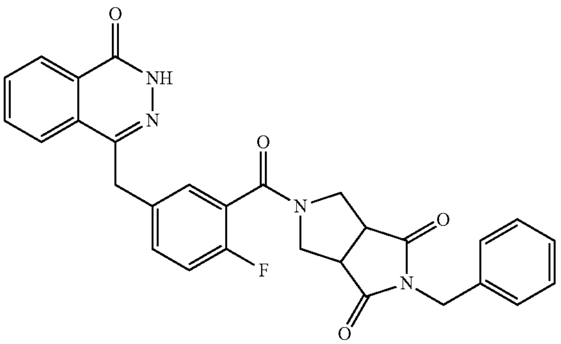 [SMILES: O=C(c1cc(Cc2n[nH]c(=O)c3ccccc23)ccc1F)N1CC2C(=O)N(Cc3ccccc3)C(=O)C2C1]

10 $^1$H NMR (400 MHz, DMSO-$d_6$): δ 12.59 (s, 1H), 8.25 (dd, J=7.6 Hz & 0.6 Hz, 1H), 7.94 (d, J=7.6 Hz, 1H), 7.86-7.80 (m, 2H), 7.35 (m, 1H), 7.32 (dd, 1H), 5.29-7.24 (m, 4H), 7.23-7.20 (m, 2H), 4.32 (s, 2H), 3.63 (m, 1H), 3.47 (m, 1H), 3.46 (m, 2H), 3.36 (m, 1H), 2.9 (dd, 1H), 2.60-2.8 (m, 3H), 2.51-2.49 (m, 2H), 2.1 (m, 1H)

EXAMPLE 12

4-(3-(1-(cyclopropanecarbonyl)-1,4,5,6-tetrahydropyrrolo[3,4-c]pyrazole-5-carbonyl)-4-fluorobenzyl) phthalazin-1(2H)-one

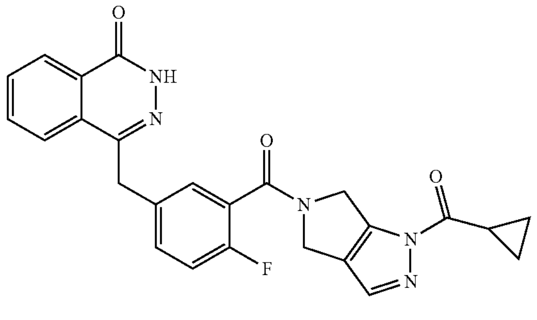 [SMILES: O=C(c1cc(Cc2n[nH]c(=O)c3ccccc23)ccc1F)N1Cc2cnn(C(=O)C3CC3)c2C1]

1H NMR (400 MHz, DMSO-d6): δ 12.57-12.60 (brd, 1H), 8.26 (d, J=7.6 Hz, 1H), 7.97 (d, J=7.6 Hz, 1H), 7.69-7.92 (m, 3H), 7.45-7.49 (m, 2H), 7.25-7.30(brt, 1H), 4.80(brs, 2H), 4.37 (brs, 2H), 4.34 (s, 2H), 4.28(brs, 1H), 2.97-3.0 (m, 1H), 1.07-1.23 (m, 4H).

EXAMPLE 13 tert-butyl 5-(2-fluoro-5-((4-oxo-3,4-dihydrophthalazin-1-yl)methyl)benzoyl) hexahydropyrrolo[3,4-c]pyrrole-2(1H)-carboxylate

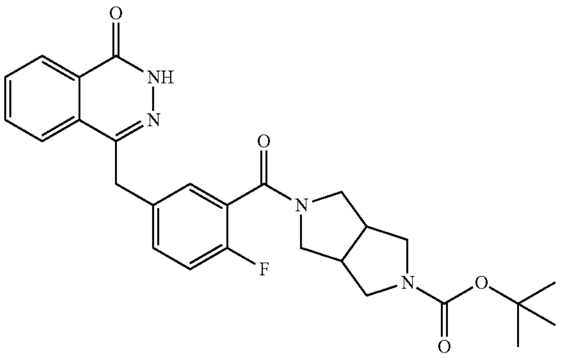 [SMILES: CC(C)(C)OC(=O)N1CC2CN(C(=O)c3cc(Cc4n[nH]c(=O)c5ccccc45)ccc3F)CC2C1]

1H NMR (400 MHz, DMSO-d6): δ 12.59 (s, 1H), 8.25 (t, J=8 Hz, 1H), 7.97 (d, J=8 Hz, 1H), 7.82-7.88 (m, 2H), 7.39-7.41 (m, 2H), 7.21-7.23 (brt, 1H), 4.32 (s, 2H), 3.68 (brs, 1H), 3.50 (brd, 2H), 3.39-3.41 (brd, 2H), 3.00-3.03 (brt, 2H), 2.81-2.89 (brd, 2H), 1.39 (s, 9H).

EXAMPLE 14

4-(4-fluoro-3-(hexahydro-1H-furo[3,4-c]pyrrole-5-carbonyl)benzyl)phthalazin-1 (2H)-one

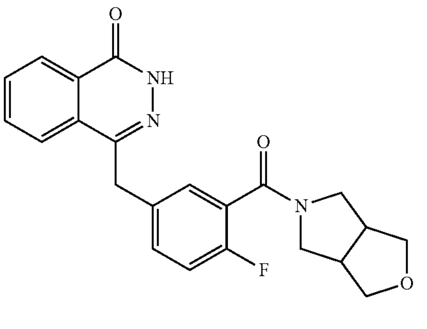 [SMILES: O=C(c1cc(Cc2n[nH]c(=O)c3ccccc23)ccc1F)N1CC2COCC2C1]

1H NMR (400 MHz, DMSO-d6): δ 12.59 (s, 1H), 8.26 (dd, J=7.6 & 0.8 Hz, 1H), 7.97 (d, J=8 Hz, 1H), 7.80-7.89 (m, 2H), 7.39-7.43 (m, 1H), 8.35 (dd, J=6.4& 2 Hz, 1H), 7.19-7.23 (brt, 1H), 4.32 (s, 2H), 3.74-3.78 (m, 1H), 3.64-3.69 (m, 2H), 3.33-3.55 (m, 4H), 3.01-3.02 (m, 2H), 2.91-3.07 (m, 2H).

EXAMPLE 15

4-(4-fluoro-3-(octahydropyrrolo[3,4-c]pyrrole-2-carbonyl)benzyl)phthalazin-1(2H)-one

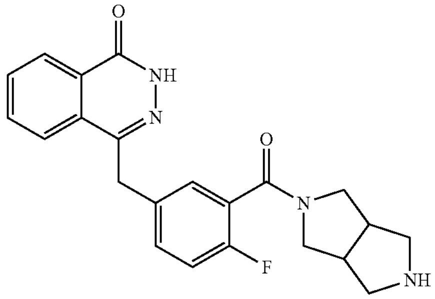 [SMILES: O=C(c1cc(Cc2n[nH]c(=O)c3ccccc23)ccc1F)N1CC2CNCC2C1]

1H NMR (400 MHz, DMSO-d6): δ 12.60 (s, 1H), 8.26 (dd, J=7.6& 0.8 Hz, 1H), 7.96 (d, J=7.6 Hz, 1H), 7.82-7.88 (m, 2H), 7.32-7.34 (m, 1H), 7.18-7.23 (m, 1H), 4.32 (s, 2H), 3.67-3.72 (m, 1H), 3.30-3.40 (m, 2H),2.77-2.96 (m, 2H), 2.58-2.73 (m, 4H), 2.41-2.44 (m, 1H).

EXAMPLE 16

4-(4-fluoro-3-(5-(methylsulfonyl)octahydropyrrolo[3,4-c]pyrrole-2-carbonyl)benzyl) phthalazin-1 (2H)-one

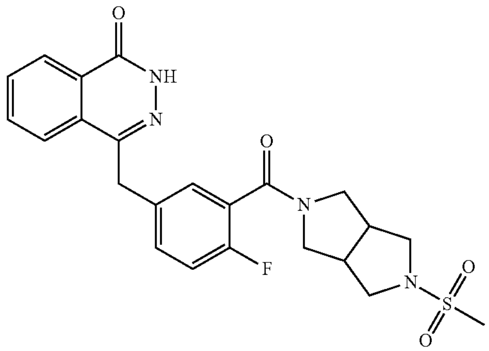 [SMILES: CS(=O)(=O)N1CC2CN(C(=O)c3cc(Cc4n[nH]c(=O)c5ccccc45)ccc3F)CC2C1]

1H NMR (400 MHz, DMSO-d6): δ 12.58 (s, 1H), 8.26 (dd, J=8 &1.2 Hz, 1H), 7.96 (d, J=8 Hz, 1H), 7.82-7.89 (m, 2H), 7.39-7.41 (brd, 2H), 7.19-7.24 (m, 1H), 4.32 (s, 2H), 3.69-3.74 (m, 1H), 3.39-3.50 (m, 5H), 2.98-3.15 (m, 4H), 2.91 (s, 3H).

EXAMPLE 17

4-(4-fluoro-3-(1-(methylsulfonyl)-1,4,5,6-tetrahydropyrrolo[3,4-c]pyrazole-5-carbonyl)benzyl) phthalazin-1(2H)-one

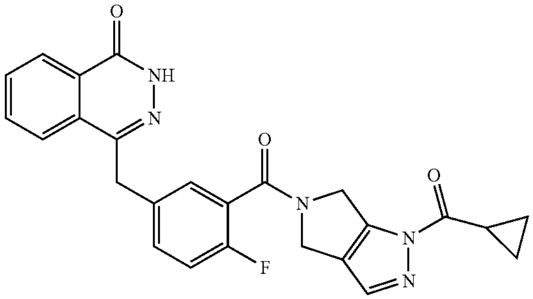 [SMILES: O=C(c1cc(Cc2n[nH]c(=O)c3ccccc23)ccc1F)N1Cc2cnn(C(=O)C3CC3)c2C1]

1H NMR (400 MHz, DMSO-d6): δ 12.59 (brd, 1H), 8.26 (d, J=7.6 Hz, 1H), 7.97 (d, J=8 Hz, 1H), 7.72-7.90 (m, 3H), 7.47-7.50 (m, 2H), 7.29-7.30(m, 1H), 4.81 (brs, 1H), 4.58 (brs, 2H), 4.34 (brs, 1H), 3.52-3.57(brd, 3H).

EXAMPLE 18

4-(3-(5-benzoyloctahydropyrrolo[3,4-c]pyrrole-2-carbonyl)-4-fluorobenzyl) phthalazin-1 (2H)-one

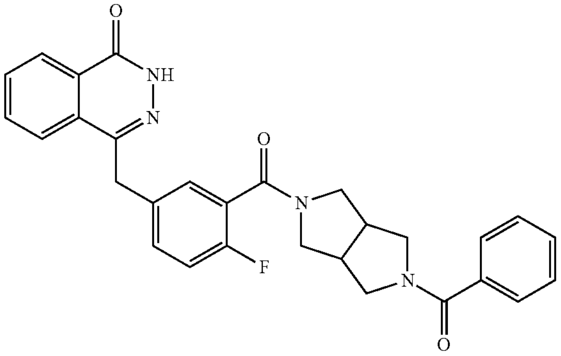 [SMILES: O=C(c1ccccc1)N1CC2CN(C(=O)c3cc(Cc4n[nH]c(=O)c5ccccc45)ccc3F)CC2C1]

1H NMR (400 MHz, DMSO-d6): δ 12.59 (s, 1H), 8.25 (d, J=7.2 Hz, 1H), 7.80-7.96 (m, 3H), 7.23-7.50 (m, 7H), 7.21-7.23 (m, 1H), 4.30-4.33 (brd, 2H), 3.38-3.75 (m, 5H).

EXAMPLE 19

4-(3-(5-(2,4-difluorobenzyl)octahydropyrrolo[3,4-c] pyrrole-2-carbonyl)-4-fluorobenzyl)phthalazin-1 (2H)-one

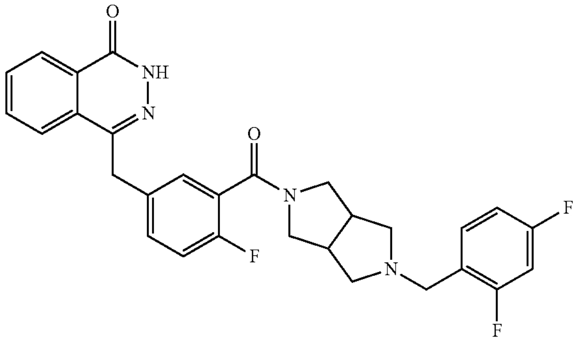 [SMILES: O=C(c1cc(Cc2n[nH]c(=O)c3ccccc23)ccc1F)N1CC2CN(Cc3ccc(F)cc3F)CC2C1]

1H NMR (400 MHz, CDCl3): δ 12.59 (s, 1H), 8.44-8.46 (m, 1H), 7.69-7.78 (m, 3H), 7.31-7.37 (m, 2H), 7.26-7.29 (m, 1H), 6.99-7.04 (brt, 1H), 6.75-6.86 (m, 2H), 4.27 (s, 2H), 3.83-3.88 (m, 1H), 3.60-3.66 (m, 4H), 3.14-3.18 (m, 1H), 2.51-2.88 (m, 5H), 2.33-2.35 (m, 1H).

EXAMPLE 20

4-(3-(5,6-dihydro-4H-furo[3,4-c]pyrrole-5-carbonyl)-4-fluorobenzyl)phthalazin-1(2H)-one

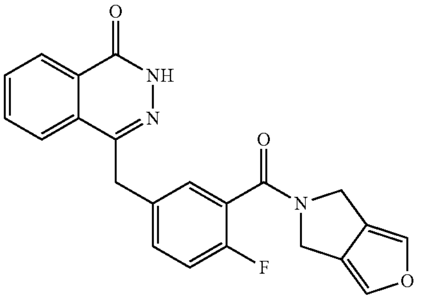 [SMILES: O=C(c1cc(Cc2n[nH]c(=O)c3ccccc23)ccc1F)N1Cc2cocc2C1]

1H NMR (400 MHz, DMSO-d6): δ 12.59 (s, 1H), 8.26 (dd, J=7.6 Hz & 1.2 Hz, 1H), 7.97 (d, J=7.6 Hz, 1H), 7.91-7.87 (m, 1H), 7.85-7.81 (m, 1H), 7.53 (d, J=1.2 Hz, 1H), 7.46-7.42 (m, 2H), 7.41-7.40 (d, J=1.2 Hz, 1H), 7.28-7.23 (m, 1H), 4.56 (s, 2H), 4.34 (s, 2H), 4.26 (s, 2H).

EXAMPLE 21

4-(4-fluoro-3-(5-methyloctahydropyrrolo[3,4-c]pyrrole-2-carbonyl)benzyl)phthalazin-1(2H)-one

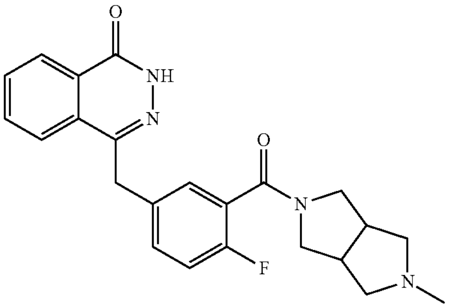 [SMILES: CN1CC2CN(C(=O)c3cc(Cc4n[nH]c(=O)c5ccccc45)ccc3F)CC2C1]

1H NMR (400 MHz, CDCl3): δ9.90 (s, 1H), 8.44-8.47 (m, 1H), 7.70-7.79 (m, 3H), 7.27-7.52 (m, 2H), 6.99-7.04 (brq, 1H), 4.26 (s, 2H), 3.85-3.90 (m, 1H), 3.62-3.64 (m, 1H), 3.44-3.51 (m, 1H), 3.19-3.21 (m, 1H), 2.73-2.97 (m, 4H).

EXAMPLE 22

5-(2-fluoro-5-((4-oxo-3,4-dihydrophthalazin-1-yl) methyl)benzoyl)tetrahydropyrrolo[3,4-c]pyrrole-1,3 (2H,3aH)-dione

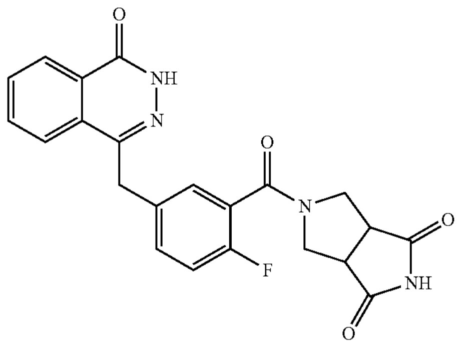 [SMILES: O=C1NC(=O)C2CN(C(=O)c3cc(Cc4n[nH]c(=O)c5ccccc45)ccc3F)CC12]

1H NMR (400 MHz, DMSO-d6): δ 12.58 (s, 1H), 11.4 (s, 1H), 8.26 (dd, J=7.6 Hz & 0.8 Hz, 1H), 7.87-7.96 (m, 2H), 7.80-7.85 (m, 1H), 7.41-7.43 (m, 1H), 7.37 (dd, J=6.4 Hz & 2.4 Hz, 1H), 7.20-7.24 (brt, 1H), 4.31 (s, 2H), 4.09-4.12 (brd, 1H), 3.38-3.58 (m, 5H).

EXAMPLE 23

4-(4-fluoro-3-(octahydrocyclopenta[c]pyrrole-2-carbonyl)benzyl)phthalazin-1(2H)-one

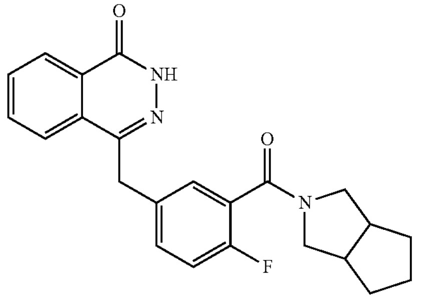 [SMILES: O=C(c1cc(Cc2n[nH]c(=O)c3ccccc23)ccc1F)N1CC2CCCC2C1]

1H NMR (400 MHz, CDCl3): δ 10.04 (s, 1H), 8.44-8.46 (m, 1H), 7.70-7.77 (m, 3H), 7.24-7.33 (brt, 1H), 7.01-7.03 (m, 1H), 6.99-7.03 (brt, 1H), 4.26 (s, 2H), 3.79-3.84 (m, 1H), 3.43-3.49 (m, 2H), 3.0-3.04 (m, 1H), 2.60-2.72 (m, 2H), 1.49-1.88 (m, 6H).

EXAMPLE 24

4-(4-fluoro-3-(5-(4-fluorobenzyl)octahydropyrrolo [3,4-c]pyrrole-2-carbonyl)benzyl) phthalazin-1 (2H)-one

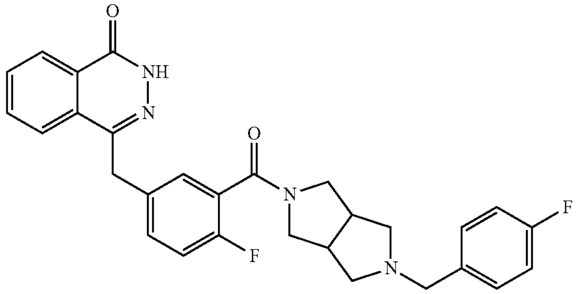 [SMILES: O=C(c1cc(Cc2n[nH]c(=O)c3ccccc23)ccc1F)N1CC2CN(Cc3ccc(F)cc3)CC2C1]

1H NMR (400 MHz, CDCl3): δ 10.18 (s, 1H), 8.44-8.46 (m, 1H), 7.69-7.76 (m, 3H), 7.33-7.35 (m, 1H), 7.25-7.34 (m, 3H), 6.96-7.04 (m, 3H), 4.27 (s, 2H), 3.83-3.88 (m, 1H), 3.45-3.64 (m, 4H), 3.13-3.17 (m, 1H), 2.80-2.90 (m, 2H), 2.62-2.63 (m, 1H), 2.49-2.52 (m, 2H), 2.28-2.31 (m, 1H).

EXAMPLE 25

4-(4-fluoro-3-(5-(2-fluorobenzyl)octahydropyrrolo [3,4-c]pyrrole-2-carbonyl)benzyl) phthalazin-1(2H)-one

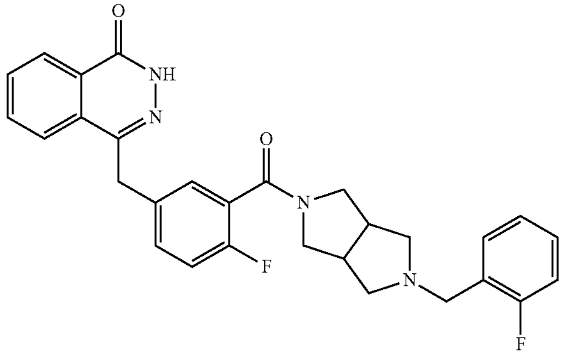 [SMILES: O=C(c1cc(Cc2n[nH]c(=O)c3ccccc23)ccc1F)N1CC2CN(Cc3ccccc3F)CC2C1]

1H NMR (400 MHz, CDCl3): δ 10.09 (s, 1H), 8.44-8.46 (m, 1H), 7.69-7.76 (m, 3H), 7.34-7.37 (m, 2H), 7.21-7.28 (m, 2H), 6.99-7.12 (m, 3H), 4.26 (s, 2H), 3.84-3.89 (m, 1H), 3.59-3.65 (m, 3H), 3.45-3.50 (m, 1H), 3.14-3.18 (m, 1H), 2.8-2.9 (m, 2H), 2.67-2.69 (m, 1H), 2.53-2.61 (m, 2H), 2.33-2.36 (m, 1H).

EXAMPLE 26

4-(4-fluoro-3-(5-(2-4-(4-fluoro-3-(5-((6-methoxy-pyridin-2-yl)methyl) octahydropyrrolo[3,4-c]pyrrole-2-carbonyl)benzyl)phthalazin-1(2H)-one

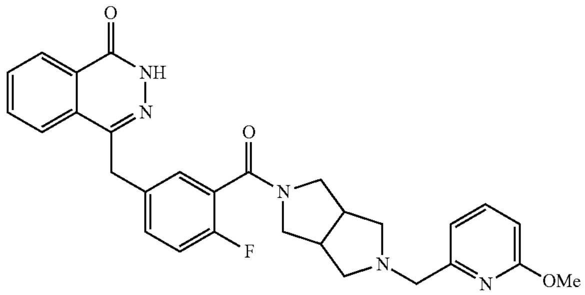 [SMILES: COc1cccc(CN2CC3CN(C(=O)c4cc(Cc5n[nH]c(=O)c6ccccc56)ccc4F)CC3C2)n1]

1H NMR (400 MHz, CDCl3): δ 10.19 (s, 1H), 8.43-8.46 (m, 1H), 7.69-7.76 (m, 3H), 7.51-7.55 (m, 1H), 7.34-7.36 (m, 1H), 7.26-7.28 (m, 1H), 7.0-7.04 (brt, 1H), 6.95 (d, J=6.8 Hz, 1H), 6.60 (d, J=8.4 Hz, 1H), 4.26 (s, 2H), 3.91 (s, 3H), 3.85-3.91 (m, 1H), 3.18-3.22 (m, 1H), 2.60-2.79 (m, 5H), 2.08-2.44 (m, 1H).

EXAMPLE 27

5-(2-fluoro-5-((4-oxo-3,4-dihydrophthalazin-1-yl) methyl)benzoyl)-2-methyl tetrahydropyrrolo[3,4-c] pyrrole-1,3(2H,3aH)-dione

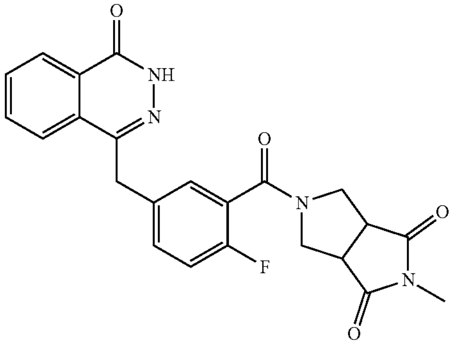 [SMILES: CN1C(=O)C2CN(C(=O)c3cc(Cc4n[nH]c(=O)c5ccccc45)ccc3F)CC2C1=O]

1H NMR (400 MHz, DMSO-d6): δ 10.17 (s, 1H), 8.45-8.47 (m, 1H), 7.74-7.82 (m, 2H), 7.69-7.71 (m, 1H), 7.26-7.34 (m, 2H), 7.02-7.06 (m, 1H), 4.45-4.49 (brd, 1H), 4.26 (s, 2H), 3.58-3.69 (m, 2H), 3.36-3.46 (m, 2H), 3.0 (s, 3H).

EXAMPLE 28

Mixture of 4-(4-fluoro-3-(1-methyl-1,4,5,6-tetrahydropyrrolo[3,4-c]pyrazole-5-carbonyl)benzyl) phthalazin-1(2H)-one compound with 4-(4-fluoro-3-(2-methyl-2,4,5,6-tetrahydropyrrolo[3,4-c]pyrazole-5-carbonyl)benzyl)phthalazin-1(2H)-one (1:3)

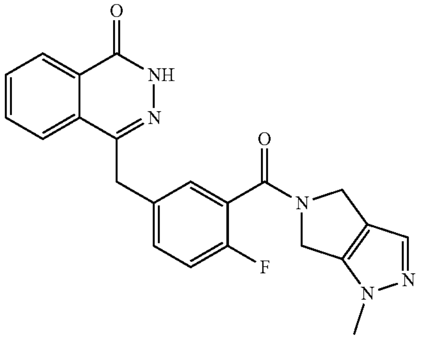

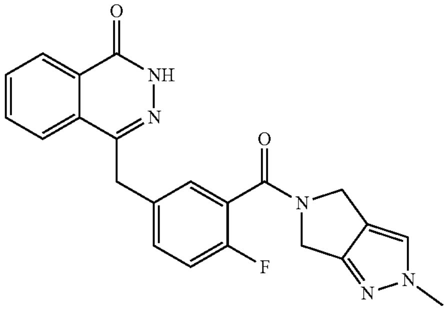

1H NMR (400 MHz, DMSO-d6): δ 12.59 (s, 1H), 8.24-8.27 (m, 1H), 7.96-7.99 (m, 1H), 7.81-7.90 (m, 2H), 7.43-7.56 (m, 3H), 7.23-7.27 (m, 1H), 4.54 (s, 2H), 4.33 (s, 2H), 4.23-4.27 (brd, 2H), 3.82 (s, 3H).

EXAMPLE 29

4-(3-(2,2-dioxido-3,4,5,6-tetrahydro-1H-thieno[3,4-c]pyrrole-5-carbonyl)-4-fluorobenzyl)phthalazin-1 (2H)-one

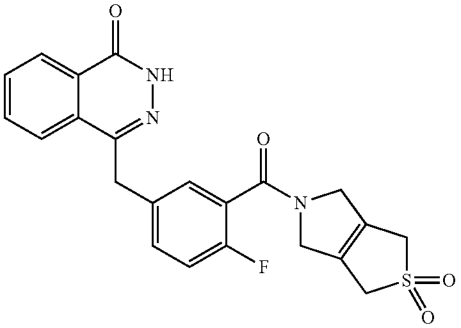 [SMILES: O=C(c1cc(Cc2n[nH]c(=O)c3ccccc23)ccc1F)N1CC2=C(C1)CS(=O)(=O)C2]

1H NMR (400 MHz, DMSO-d6): δ 12.58 (s, 1H), 8.27 (d, J=7.6 Hz, 1H), 7.98 (d, J=8 Hz, 1H), 7.91 (dd, J=14 Hz & 6.8 Hz, 1H), 7.85-7.81 (m, 1H), 7.45-7.44 (m, 2H), 7.28-7.23 (m, 1H), 4.35-4.32 (d, 4H), 4.06 (s, 2H), 4.007 (s, 2H), 3.88 (s, 2H).

EXAMPLE 30

4-(3-(5,6-dihydro-4H-thieno[3,4-c]pyrrole-5-carbonyl)-4-fluorobenzyl)phthalazin-1(2H)-one

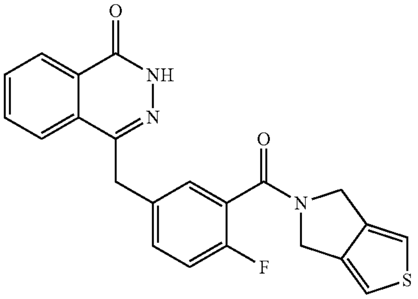 [SMILES: O=C(c1cc(Cc2n[nH]c(=O)c3ccccc23)ccc1F)N1Cc2cscc2C1]

1H NMR (400 MHz, DMSO-d6): δ 12.58 (s, 1H), 8.26 (dd, J=8 Hz & 1.2 Hz, 1H), 7.97 (d, J=7.6 Hz, 1H), 7.91-7.87 (m, 1H), 7.85-7.81 (m, 1H), 7.46-7.43 (m, 2H), 7.29-7.23 (m, 2H), 7.16 (m, 1H), 4.59 (s, 2H), 4.34 (s, 2H), 4.29 (s, 2H).

EXAMPLE 31

4-(4-fluoro-3-(1,2,3,4,5,6-hexahydropyrrolo[3,4-c] pyrrole-2-carbonyl)benzyl) phthalazin-1(2H)-one

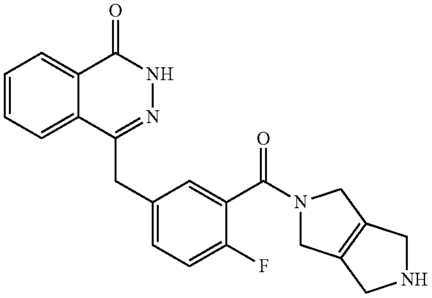 [SMILES: O=C(c1cc(Cc2n[nH]c(=O)c3ccccc23)ccc1F)N1CC2=C(CNC2)C1]

1H NMR (400 MHz, DMSO-d6): δ 12.59 (s, 1H), 8.26 (m, J=7.6 Hz & 1.2 Hz, 1H), 7.96 (d, J=7.6 Hz, 1H), 7.90-7.84 (m, 1H), 7.82-7.80 (m, 1H), 7.44-7.40 (m, 2H), 7.22-7.21 (m, 1H), 4.32 (s, 2H), 4.26-4.19 (d, 2H), 3.96-3.87 (d, 2H), 3.63-3.59 (d, 2H), 3.58-3.48 (d, 2H).

m

EXAMPLE 32

4-(4-fluoro-3-(5-phenyloctahydropyrrolo[3,4-c]pyrrole-2-carbonyl)benzyl)phthalazin-1(2H)-one

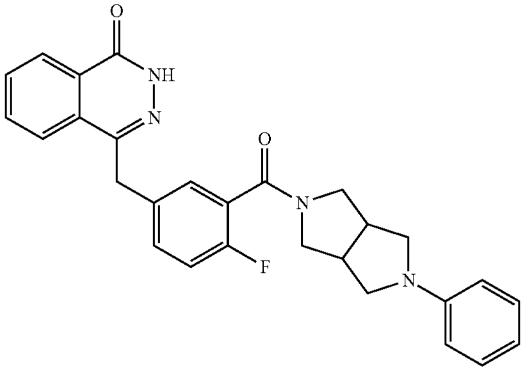 [SMILES: O=C(c1cc(Cc2n[nH]c(=O)c3ccccc23)ccc1F)N1CC2CN(c3ccccc3)CC2C1]

1H NMR (400 MHz, DMSO-d6): δ 12.58 (s, 1H), 8.25 (dd, J=7.6 & 1.2 Hz, 1H), 7.95 (d, J=7.6 Hz, 1H), 7.80-7.85 (m, 2H), 7.36-7.42 (m, 2H), 7.14-7.23 (m, 3H), 6.62 (t, J=7.6 Hz, 1H), 6.52 (d, J=8 Hz, 2H), 4.31 (s, 2H), 3.74-3.79 (m, 1H), 3.42-3.48 (m, 3H), 3.32-3.36 (m, 1H), 3.18-3.22 (m, 1H), 2.96-3.10 (m, 4H)

EXAMPLE 33

4-(4-fluoro-3-(5-methyl-1,2,3,4,5,6-hexahydropyrrolo[3,4-c]pyrrole-2-carbonyl) benzyl) phthalazin-1 (2H)-one

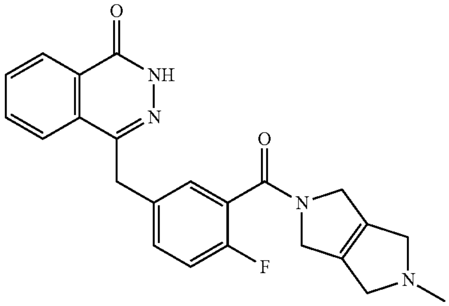 [SMILES: CN1CC2=C(C1)CN(C(=O)c1cc(Cc3n[nH]c(=O)c4ccccc34)ccc1F)C2]

1H NMR (400 MHz, DMSO-d6): δ 12.59 (s, 1H), 8.26 (dd, J=8 Hz & 0.8 Hz, 1H), 7.96 (d, J=7.6 Hz, 1H), 7.90-7.86 (m, 1H), 7.84-7.80 (m, 1H), 7.43-7.40 (m, 2H), 7.25-7.21 (m, 1H), 4.32 (s, 2H), 4.19 (s, 2H), 3.58 (s, 2H), 3.43 (s, 2H), 2.42 (s, 3H).

EXAMPLE 34

4-(3-((3 aR,8bR)-decahydropyrrolo[3,4-a]pyrrolizine-2-carbonyl)-4-fluorobenzyl) phthalazin-1 (2H)-one

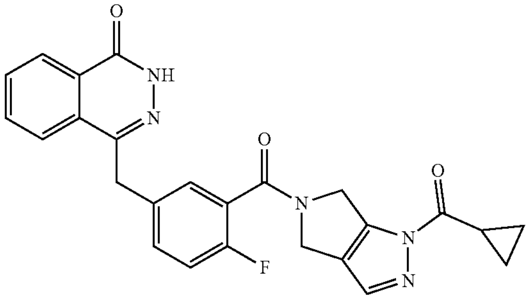 [SMILES: O=C(c1cc(Cc2n[nH]c(=O)c3ccccc23)ccc1F)N1Cc2cnn(C(=O)C3CC3)c2C1]

1H NMR (400 MHz, DMSO-d6): δ 10.5-10.2 (d, 1H), 8.44-8.46 (m, 1H), 7.71-7.77 (m, 3H), 7.41-7.38 (m, 1H), 7.24 (d, J=2.4 Hz, 1H), 7.02-6.99 (m, 1H), 4.24 (s, 2H), 3.89-0.88 (m, 15H).

EXAMPLE 35

4-(4-fluoro-3-(2-methyl-2,4,5,6-tetrahydropyrrolo[3,4-c]pyrazole-5-carbonyl)benzyl) phthalazin-1(2H)-one

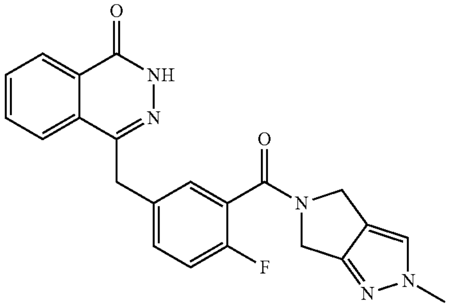 [SMILES: Cn1cc2c(n1)CN(C(=O)c1cc(Cc3n[nH]c(=O)c4ccccc34)ccc1F)C2]

1H NMR (400 MHz, CDCl3): δ 10.02 (s, 1H), 8.44-8.46 (m, 1H), 7.69-7.79 (m, 3H), 7.29-7.40 (m, 2H), 7.04-7.17 (m, 2H), 4.73-4.77 (brd, 2H), 4.37-4.39 (brd, 2H), 4.28 (s, 2H), 3.89-3.90 (brd, 2H).

EXAMPLE 36

4-(4-fluoro-3-(1-methyl-2,4,5,6-tetrahydropyrrolo[3,4-c]pyrazole-5-carbonyl)benzyl) phthalazin-1 (2H)-one

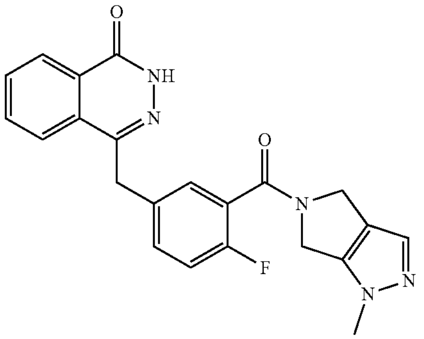 [SMILES: Cn1ncc2c1CN(C(=O)c1cc(Cc3n[nH]c(=O)c4ccccc34)ccc1F)C2]

1H NMR (400 MHz, CDCl3): δ 9.98 (s, 1H), 8.44-8.47 (m, 1H), 7.70-7.80 (m, 3H), 7.31-7.40 (m, 2H), 7.06-7.30 (m, 2H), 4.72-4.78 (brd, 2H), 4.37-4.44 (brd, 2H), 4.28-4.29 (brd, 2H), 3.73-3.85 (brd, 3H).

EXAMPLE 37

2-((5-(2-fluoro-5-((4-oxo-3,4-dihydrophthalazin-1-yl)methyl)benzoyl) hexahydropyrrolo[3,4-c]pyrrol-2 (1H)-yl)methyl)-6-methoxypyridine-1-oxide

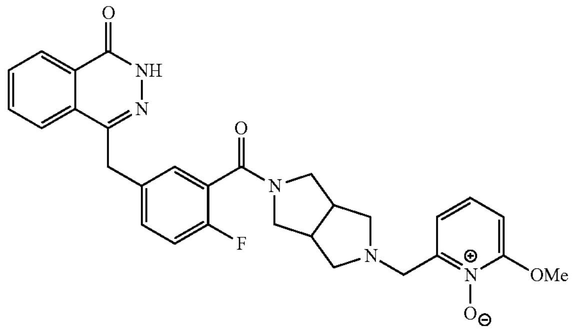 [SMILES: COc1cccc(CN2CC3CN(C(=O)c4cc(Cc5n[nH]c(=O)c6ccccc56)ccc4F)CC3C2)[n+]1[O-]]

1H NMR (400 MHz, DMSO-d6): δ 12.70 (s, 1H), 8.26 (d, J=8.8 Hz, 1H), 8.83-8.91 (m, 3H), 7.67-7.70 (m, 1H), 7.41-7.45 (m, 1H), 7.28-7.30 (m, 1H), 7.16-7.23 (m, 1H), 6.82 (d, J=8 Hz, 1H), 4.40-4.41 (brd, 2H), 4.31 (s, 2H), 3.82 (s, 3H), 3.70-3.73 (brd, 1H), 3.37-3.47 (m, 3H), 3.12-3.25 (m, 3H), 2.99-3.02 (brd, 1H).

EXAMPLE 38

4-(3-(5-(difluoromethyl)octahydropyrrolo[3,4-c] pyrrole-2-carbonyl)-4-fluorobenzyl) phthalazin-1 (2H)-one

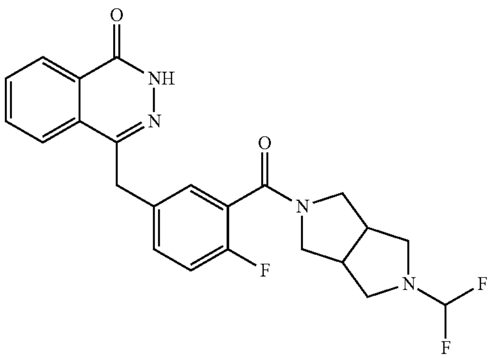 [SMILES: O=C(c1cc(Cc2n[nH]c(=O)c3ccccc23)ccc1F)N1CC2CN(C(F)F)CC2C1]

1H NMR (400 MHz, CDCl3): δ 10.25 (s, 1H), 8.45-8.47 (m, 1H), 8.21-8.24 (m, 1H), 7.71-7.79 (m, 3H), 7.30-7.32 (m, 1H), 7.26-7.29 (m, 1H), 7.01-7.05 (m, 1H), 4.27 (s, 2H), 3.87-3.93 (m, 1H), 3.73-3.82 (m, 1H), 3.56-3.70 (m, 1H), 3.46-3.50 (m, 1H), 3.30-3.34 (m, 1H), 3.18-3.23 (m, 1H), 2.92-2.95 (m, 1H).

EXAMPLE 39

4-(4-fluoro-3-((3 aR,6aS)-5-oxooctahydrocyclopenta [c]pyrrole-2-carbonyl)benzyl) phthalazin-1 (2H)-one

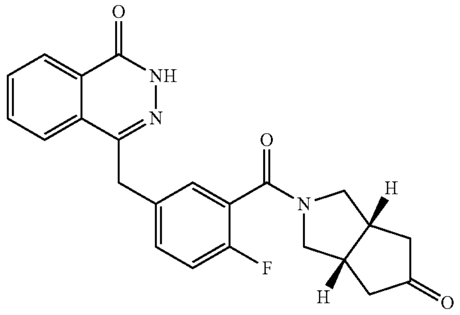 [SMILES: O=C1C[C@@H]2CN(C(=O)c3cc(Cc4n[nH]c(=O)c5ccccc45)ccc3F)C[C@@H]2C1]

1H NMR (400 MHz, CDCl3): δ 10.63 (s, 1H), 8.47-8.49 (m, 1H), 7.72-7.81 (m, 3H), 7.37-7.39 (m, 1H), 7.30-7.33 (m, 1H), 7.02-7.04 (brt, 1H), 4.30 (s, 2H), 3.95-4.00 (m, 1H), 3.55-3.65 (m, 2H), 3.18-3.22 (m, 1H), 2.94-3.10 (m, 2H), 2.44-2.61 (m, 2H), 2.22-2.28 (m, 1H), 2.08-2.18 (m, 1H).

EXAMPLE 40

Mixture of 1 & 2 Ethyl 4-(3-(2,4,5,6-tetrahydropyrrolo[3,4-c]pyrazole-5-carbonyl)-4-fluorobenzyl) phthalazin-1(2H)-one

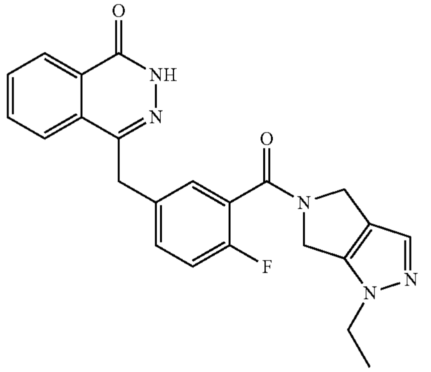

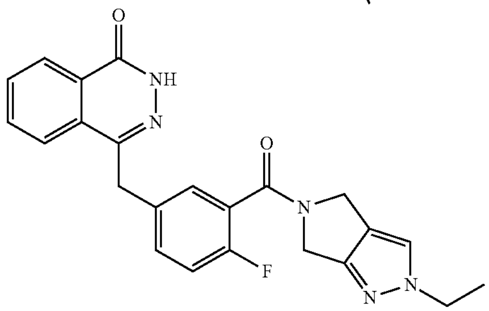

1H NMR (400 MHz, DMSO-d6): δ 12.60 (s, 1H), 8.25 (t, 1H), 7.99 (dd, J=7.6 Hz & 4 Hz, 1H), 7.91-7.87 (m, 1H), 7.85-7.81 (m, 1H), 7.61-7.42 (m, 3H), 7.28-7.23 (m, 1H), 5.31 (s, 1H), 4.55 (d, 1H), 4.52-4.43 (d, 2H), 4.34 (s, 2H), 4.28-4.20 (t, 2H), 4.14-4.08 (m, 2H), 3.39-3.35 (m, 2H), 1.67-1.10 (m, 6H).

EXAMPLE 41

4-(3-(2-ethyl-2,4,5,6-tetrahydropyrrolo[3,4-c]pyrazole-5-carbonyl)-4-fluorobenzyl) phthalazin-1 (2H)-one

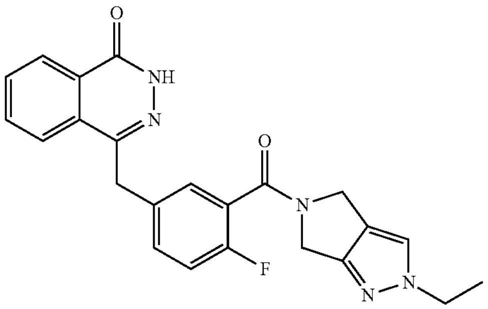 [SMILES: CCn1cc2c(n1)CN(C(=O)c1cc(Cc3n[nH]c(=O)c4ccccc34)ccc1F)C2]

1H NMR (400 MHz, DMSO-d6): δ 12.59 (s, 1H), 8.26 (d, J=8 Hz, 1H), 7.98 (d, J=7.6 Hz, 1H), 7.88 (d, J=8 Hz, 1H), 7.84 (d, J=7.6 Hz, 1H), 7.61 (s, 1H), 7.46 (d, J=5.6 Hz, 2H), 5.25 (m, 1H), 4.55 (s, 2H), 4.33 (s, 2H), 4.26 (d, 2H), 4.10 (q, 2H), 1.36-1.32 (m, 3H).

EXAMPLE 42

4-(3-(1-ethyl-1,4,5,6-tetrahydropyrrolo[3,4-c]pyrazole-5-carbonyl)-4-fluorobenzyl) phthalazin-1 (2H)-one

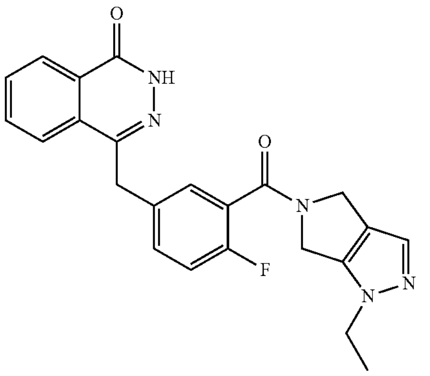 [SMILES: CCn1ncc2c1CN(C(=O)c1cc(Cc3n[nH]c(=O)c4ccccc34)ccc1F)C2]

1H NMR (400 MHz, DMSO-d6): δ 10.37-10.34 (d, 2H), 8.47-8.45 (dd, 1H), 7.82-7.22 (m, 3H), 7.41-7.33 (m, 2H), 7.20 (s, 1H), 7.13-6.99 (m, 1H), 4.82 (s, 1H), 4.72 (s, 1H), 4.46 (s, 1H), 4.37 (s, 1H), 4.37-4.31 (d, 2H), 4.15 (q, 2H), 1.48 (t,2H), 1.37 (t, 1H).

EXAMPLE 43

4-(4-fluoro-3-(1-isopropyl-1,4,5,6-tetrahydropyrrolo [3,4-c]pyrazole-5-carbonyl) benzyl)phthalazin-1 (2H)-one

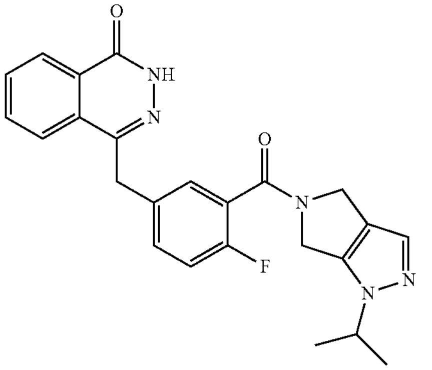

1H NMR (400 MHz, DMSO-d6): δ 12.56 (s, 1H), 8.24 (d, J=7.6 Hz, 1H), 7.95 (t, 1H), 7.87 (t, 1H), 7.81 (t, 1H), 7.46-7.42 (m, 2H), 7.27-7.22 (m, 1H), 7.15 (s, 1H), 4.74 (s, 1H), 4.48 (s, 1H), 4.45 (m, 1H), 4.32 (s, 2H), 4.30-4.26 (m, 1H), 4.16 (s, 1H), 1.37 (d, 3H), 1.23 (t, 3H).

EXAMPLE 44

Mixture of (1 & 2 isopropyl) 4-(4-fluoro-3-(1,4,5,6-tetrahydropyrrolo[3,4-c]pyrazole-5-carbonyl)benzyl) phthalazin-1(2H)-one

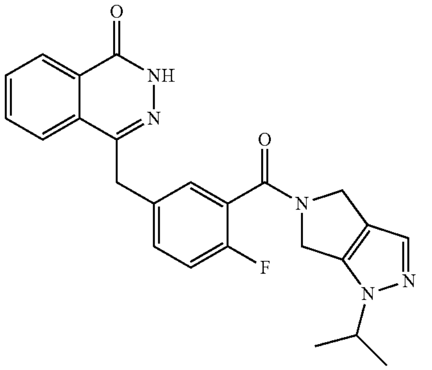 [SMILES: CC(C)n1ncc2c1CN(C(=O)c1cc(Cc3n[nH]c(=O)c4ccccc34)ccc1F)C2]

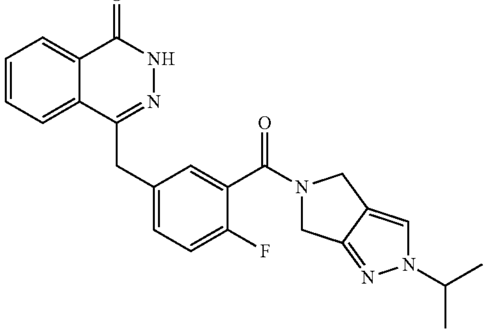

1H NMR (400 MHz, DMSO-$d_6$): δ 12.58 (s, 1H), 8.26 (d, J=7.6 Hz, 1H), 7.98 (d, J=8 Hz, 1H), 7.91-7.81 (m, 2H), 7.48-7.42 (m, 2H), 7.29-7.23 (m, 1H), 7.17 (s, 1H), 4.55 (s, 1H), 4.49-4.44 (m, 1H), 4.33 (s, 2H), 4.29 (s, 1H), 4.24 (s, 1H), 1.40 (dd, 5H), 1.25 (t, 1H).

EXAMPLE 45

4-(4-fluoro-3-(2-isopropyl-2,4,5,6-tetrahydropyrrolo [3,4-c]pyrazole-5-carbonyl)benzyl) phthalazin-1 (2H)-one

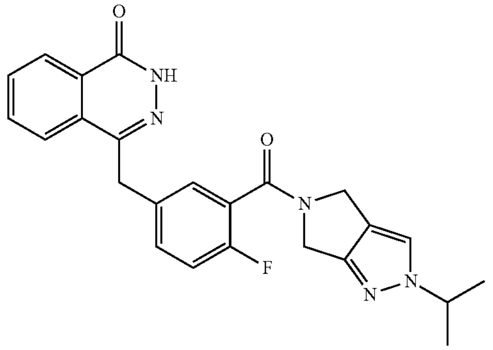 [SMILES: CC(C)n1cc2c(n1)CN(C(=O)c1cc(Cc3n[nH]c(=O)c4ccccc34)ccc1F)C2]

1H NMR (400 MHz, DMSO-d6): δ 12.57 (s, 1H), 8.26 (d, J=7.6 Hz & 1.2 Hz, 1H), 7.98 (t, 1H), 7.91-7.87 (m, 1H), 7.85-7.81 (m, 1H), 7.64-7.50 (d, 1H), 7.46-7.42 (m, 2H), 7.27 (t, 1H), 4.55 (s, 2H), 4.49-4.46 (m, 1H), 4.33 (s, 2H), 4.29 (s, 1H), 4.24 (s, 1H), 1.40-1.38 (dd, 6H).

EXAMPLE 46

4-(3-((3 aR,6aS)-5,5-difluorooctahydrocyclopenta[c] pyrrole-2-carbonyl)-4-fluorobenzyl)phthalazin-1 (2H)-one

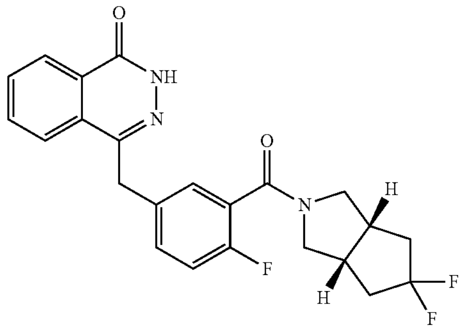 [SMILES: O=C(c1cc(Cc2n[nH]c(=O)c3ccccc23)ccc1F)N1C[C@@H]2CC(F)(F)C[C@@H]2C1]

1H NMR (400 MHz, CDCl3): δ 10.07 (s, 1H), 8.45-8.47 (m, 1H), 7.70-7.79 (m, 3H), 7.35-7.37 (m, 1H), 7.24-7.31 (m, 1H), 7.01-7.05 (brt, 1H), 4.27 (s, 2H), 3.82-3.87 (m, 1H), 3.65-3.70 (m, 1H), 3.51-3.56 (m, 1H), 3.18-3.22 (m, 1H), 2.80-2.94 (m, 2H), 2.26-2.45 (m, 2H), 1.87-2.08 (m, 2H).

EXAMPLE 47

4-(4-fluoro-3-(5-(2-methoxyethyl)octahydropyrrolo [3,4-c]pyrrole-2-carbonyl)benzyl) phthalazin-1 (2H)-one

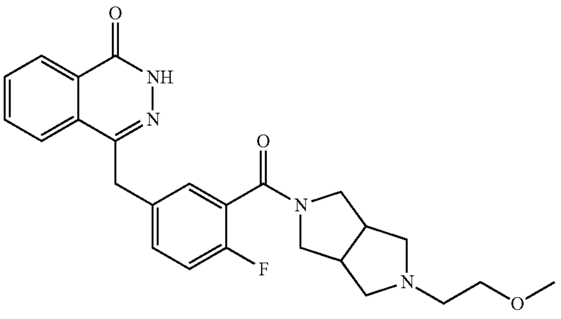 [SMILES: COCCN1CC2CN(C(=O)c3cc(Cc4n[nH]c(=O)c5ccccc45)ccc3F)CC2C1]

1H NMR (400 MHz, CDCl3): δ 10.25 (s, 1H), 8.44-8.47 (m, 1H), 7.71-7.79 (m, 3H), 7.34-7.36 (m, 1H), 7.26-7.30 (m, 1H), 6.99-7.04 (brt, 1H), 4.27 (s, 2H), 3.64-3.79 (m, 2H), 3.50-3.53 (m, 2H), 3.42-3.47 (m, 1H), 3.36 (s, 3H), 3.16-3.18 (brd, 1H), 2.80-2.97 (m, 2H), 2.64-2.68 (m, 2H), 2.41-2.42 (brd, 1H).

EXAMPLE 48

N-((3 aR,6aS)-2-(2-fluoro-5-((4-oxo-3,4-dihydrophthalazin-1-yl)methyl)benzoyl) octahydrocyclopenta[c]pyrrol-5-yl)cyclopropanecarboxamide

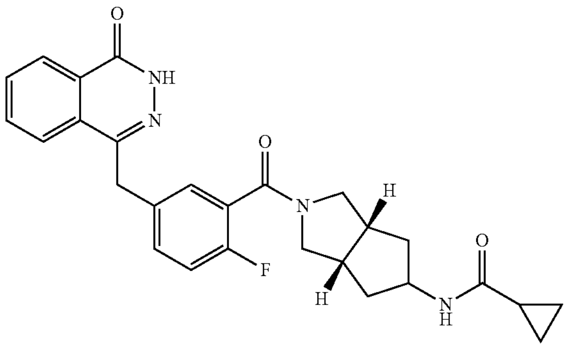 [SMILES: O=C(NC1C[C@@H]2CN(C(=O)c3cc(Cc4n[nH]c(=O)c5ccccc45)ccc3F)C[C@@H]2C1)C1CC1]

1H NMR (400 MHz, CDCl3): δ 10.38 (s, 1H), 8.44-8.46 (m, 1H), 7.72-7.78 (m, 3H), 7.42-7.44 (m, 1H), 7.26-7.29 (m, 1H), 6.98-7.03 (brt, 1H), 5.57 (brd, 1H), 4.40-4.42 (m, 1H), 4.27 (s, 2H), 3.79-3.85 (m, 1H), 3.48-3.60 (m, 2H), 3.06-3.10 (m, 1H), 2.78-2.85 (m, 2H), 1.90-2.00 (m, 1H), 1.70-1.88 (m, 1H), 1.00-1.03 (m, 2H), 0.83-0.90 (m, 1H), 0.73-0.75 (m, 2H)

EXAMPLE 50

4-(4-fluoro-3-(1-methyl-2,4,5,6-tetrahydropyrrolo[3,4-c]pyrazole-5-carbonyl)benzyl) phthalazin-1 (2H)-one hydrobromide

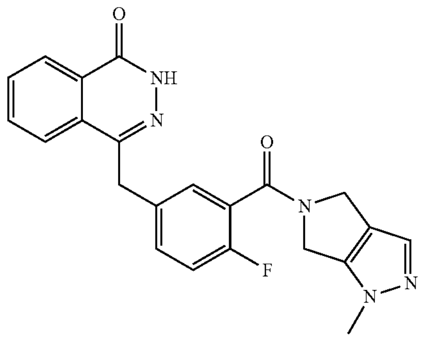 [SMILES: Cn1ncc2c1CN(C(=O)c1cc(Cc3n[nH]c(=O)c4ccccc34)ccc1F)C2]

1H NMR (400 MHz, DMSO-d6): δ 12.59 (d, J=3.6 Hz, 1H), 8.26(d. J=7.6 Hz, 1H), 8.005-7.92 (m, 1H), 7.911-7.87 (m, 1H), 7.85-7.81 (m, 1H), 7.48-7.43 (m, 2H), 7.30-7.25 (m, 1H), 7.15 (brs, 1H), 4.69 (s, 1H), 4.53 (s, 1H), 4.42 (s, 1H), 4.34 (s, 2H), 4.21 (s, 1H), 3.78-3.66 (brd, 3H).

EXAMPLE 51

4-(4-fluoro-3-(1-methyl-2,4,5,6-tetrahydropyrrolo[3,4-c]pyrazole-5-carbonyl)benzyl) phthalazin-1 (2H)-one hydrochloride

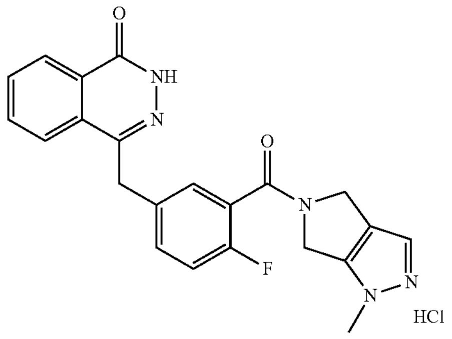 [SMILES: Cn1ncc2c1CN(C(=O)c1cc(Cc3n[nH]c(=O)c4ccccc34)ccc1F)C2 ; Cl]

1H NMR (400 MHz, DMSO-d6): δ 12.59-12.59 (d, J=3.6 Hz, 1H), 8.26 (d, J=7.6 Hz, 1H), 7.98 (t, J=8 Hz, 1H), 7.89 (t, J=3.4 Hz, 1H), 7.83 (t, J=7.4 Hz, 1H), 7.43-7.48 (m, 2H), 7.26-7.28 (m, 1H), 7.15-7.27 (brd, 1H), 4.53-4.69 (brd, 2H), 4.34 (s, 2H), 4.21-4.42 (brd, 2H), 3.66-3.78 (brd, 3H).

EXAMPLE 52

4-(4-fluoro-3-(1-methyl-1,4,5,6-tetrahydropyrrolo[3,4-c]pyrazole-5-carbonyl)benzyl) phthalazin-1 (2H)-one sulfate

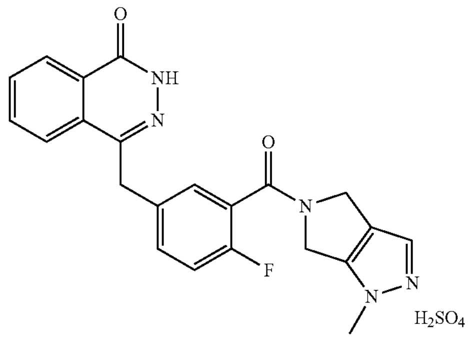

1H NMR (400 MHz DMSO-d6): δ 12.59-12.58 (d, J=3.2 Hz, 1H), 8.26 (d, J=8 Hz, 1H), 7.97 (m, 1H), 7.89 (m, 1H), 7.84 (m, 1H), 7.48-7.43 (m, 2H), 7.15 (s, 1H), 4.53 (s, 1H), 4.41 (s, 1H), 4.34 (s, 2H), 4.21 (s, 1H), 3.78 (s, 3H), 3.73 (m, 1H).

EXAMPLE 53

4-(4-fluoro-3-(1-methyl-1,4,5,6-tetrahydropyrrolo[3,4-c]pyrazole-5-carbonyl)benzyl) phthalazin-1 (2H)-one 4-methylbenzenesulfonate

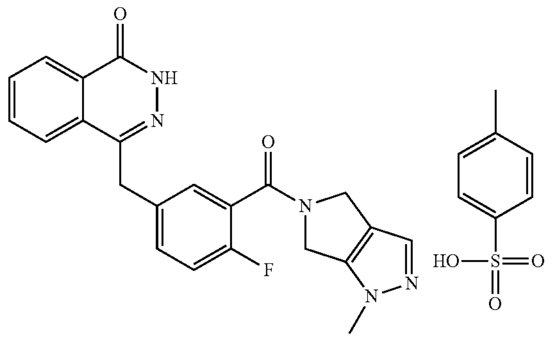

1H NMR (400 MHz, DMSO-d6): δ 12.59-12.58 (d, J=3.2 Hz, 1H), 8.26 (d, J=7.6 Hz, 1H), 7.98 (m, 1H), 7.904 (m, 1H), 7.87-7.81 (m, 1H), 7.48-7.43 (m, 4H), 7.3-7.28 (m, 1H), 7.11 (m, 2H), 4.69 (s, 1H), 4.53 (s, 1H), 4.41 (s, 1H), 4.21 (s, 1H), 3.72 (s, 3H), 2.28 (s, 3H)

EXAMPLE 54

4-(4-fluoro-3-(1-methyl-1,4,5,6-tetrahydropyrrolo[3,4-c]pyrazole-5-carbonyl)benzyl) phthalazin-1 (2H)-one benzenesulfonate

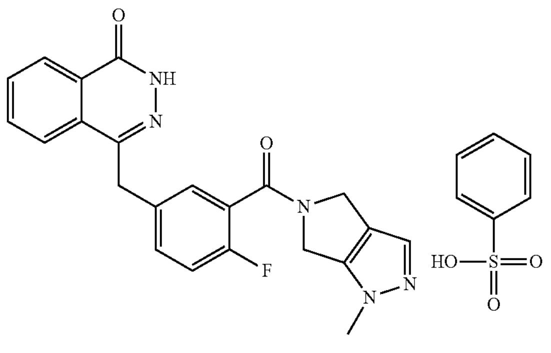

1H NMR (400 MHz, DMSO-d6): δ 12.59-12.59 (d, J=3.2 Hz, 1H), 8.26 (d, J=8 Hz, 1H), 7.87-7.92 (m, 1H), 7.83 (t, J=7.6 Hz, 1H), 7.58-7.61(m, 2H), 7.43-7.48 (m, 2H), 7.15-7.34 (m, 7H), 4.53-4.69 (brd, 2H), 4.34 (s, 2H), 4.21-4.41 (brd, 2H), 3.66-3.78 (brd, 3H).

EXAMPLE 55

5-(2-fluoro-5-((4-oxo-3,4-dihydrophthalazin-1-yl) methyl)benzoyl)-2-isopropyl-2,4,5,6-tetrahydropyrrolo[3,4-c]pyrazol-2-ium hydrogensulfate

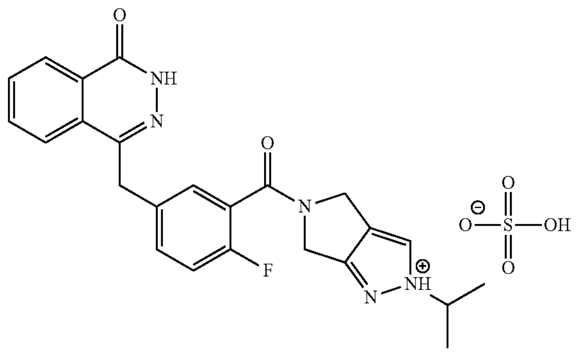 [SMILES: CC(C)[NH+]1C=C2CN(C(=O)c3cc(Cc4n[nH]c(=O)c5ccccc45)ccc3F)CC2=N1 ; O=S(=O)([O-])O]

1H NMR (400 MHz, DMSO-d6): δ 12.58 (s, 1H), 8.26 (dd, J=8 Hz & 1.2 Hz, 1H), 7.98 (dd, J=7.6 Hz & 2.4 Hz, 1H), 7.91-7.87 (m, 1H), 7.85-7.81 (m, 1H), 7.64-7.51 (brd, 1H), 7.47-7.42 (m, 2H), 7.28-7.23 (m, 1H), 4.55 (s, 2H), 4.51-4.45 (m, 1H), 4.33 (s, 2H), 4.29-4.24 (brd, 2H), 1.40-1.38 (brd, 4H).

EXAMPLE 56

4-(3-(1-cyclopropyl-1,4,5,6-tetrahydropyrrolo [3,4-c]pyrazole-5-carbonyl)-4-fluorobenzyl)phthalazin-1 (2H)-one

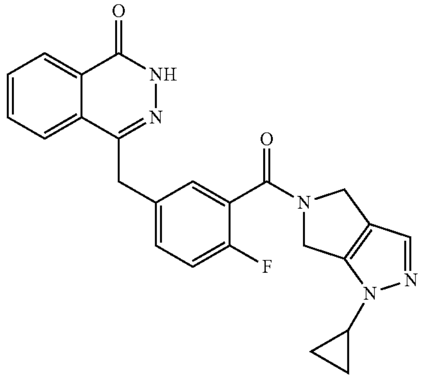 [SMILES: O=C(c1cc(Cc2n[nH]c(=O)c3ccccc23)ccc1F)N1Cc2cnn(C3CC3)c2C1]

$^1$H NMR (400 MHz, DMSO-$d_6$): δ 12.58 (d, J=2.4 Hz, 1H), 8.24(d, J=7.6 Hz, 1H), 7.98-7.37 (m, 1H), 7.89-7.85 (m, 1H), 7.81 (t, 1H), 7.47-7.39 (m, 2H), 7.28-7.22 (m, 1H), 7.14 (d, 1H), 4.70 (s, 1H), 4.48 (s, 1H), 4.42 (s, 1H), 4.32 (s, 2H), 4.16 (s, 1H), 3.57-3.44 (m, 1H), 0.98-0.82 (m, 4H).

The following compounds can be synthesized following the same procedure as described for example 1 and are considered to be encompassed within the scope of the present invention.

4-(4-fluoro-3-(1-propyl-1,4,5,6-tetrahydropyrrolo[3,4-c]pyrazole-5-carbonyl)benzyl) phthalazin-1 (2H)-one

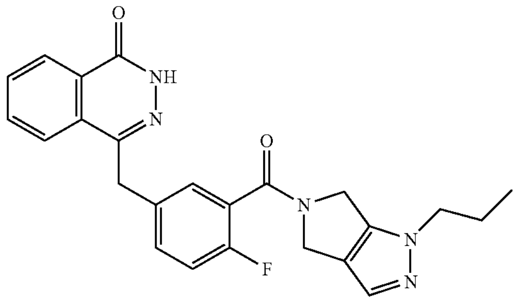 [SMILES: CCCn1ncc2c1CN(C(=O)c1cc(Cc3n[nH]c(=O)c4ccccc34)ccc1F)C2]

2-(cyclopropanecarbonyl)-5-(2-fluoro-5-((4-oxo-3,4-dihydrophthalazin-1-yl)methyl) benzoyl)tetrahydropyrrolo[3,4-c]pyrrole-1,3(2H,3aH)-dione

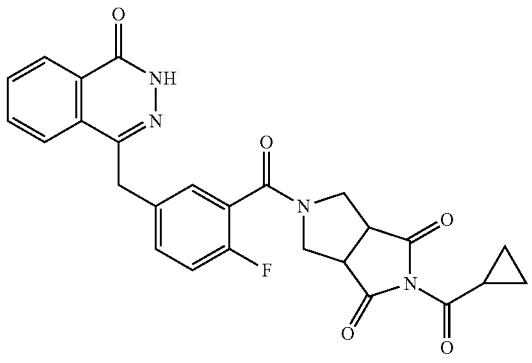 [SMILES: O=C(c1cc(Cc2n[nH]c(=O)c3ccccc23)ccc1F)N1CC2C(=O)N(C(=O)C3CC3)C(=O)C2C1]

5-(cyclopropanecarbonyl)-2-(2-fluoro-5-((4-oxo-3,4-dihydrophthalazin-1-yl)methyl) benzoyl)tetrahydro-pyrrolo[3,4-c]pyrrole-1,3(2H,3aH)-dione

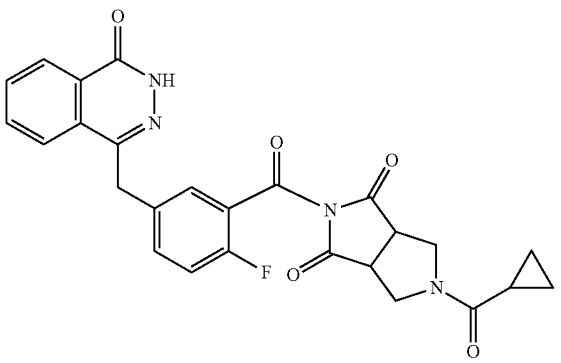 [SMILES: O=C(C1CC1)N1CC2C(=O)N(C(=O)c3cc(Cc4n[nH]c(=O)c5ccccc45)ccc3F)C(=O)C2C1]

4-(4-fluoro-3-(2-(trifluoromethyl)-5,6-dihydro-4H-pyrrolo[3,4-d]oxazole-5-carbonyl) benzyl) phthalazin-1(2H)-one

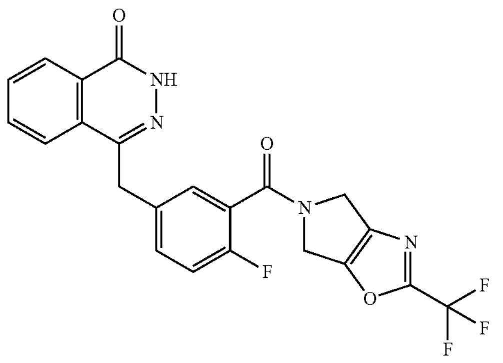 [SMILES: O=C(c1cc(Cc2n[nH]c(=O)c3ccccc23)ccc1F)N1Cc2nc(C(F)(F)F)oc2C1]

4-(3-(2-(cyclopropanecarbonyl)-5,6-dihydro-4H-pyrrolo[3,4-d]oxazole-5-carbonyl)-4-fluorobenzyl) phthalazin-1(2H)-one

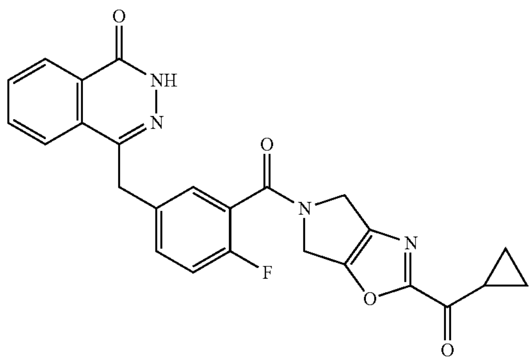 [SMILES: O=C(c1nc2c(o1)CN(C(=O)c1cc(Cc3n[nH]c(=O)c4ccccc34)ccc1F)C2)C1CC1]

4-(4-fluoro-3-(2-(trifluoromethyl)-4,5,6,6a-tetrahydro-3aH-pyrrolo[3,4-d]thiazole-5-carbonyl)benzyl)phthalazin-1(2H)-one

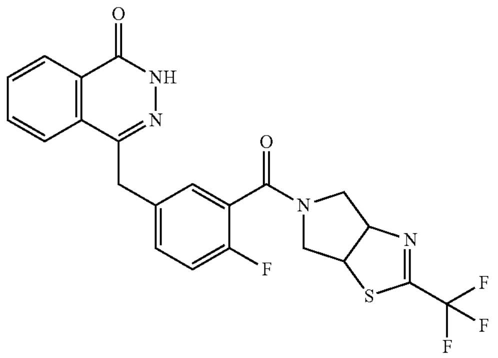 [SMILES: O=C(c1cc(Cc2n[nH]c(=O)c3ccccc23)ccc1F)N1CC2N=C(C(F)(F)F)SC2C1]

5-(2-fluoro-5-((4-oxo-3,4-dihydrophthalazin-1-yl) methyl)benzoyl)dihydro-1H-furo[3,4-c]pyrrole-4,6 (5H,6aH)-dione

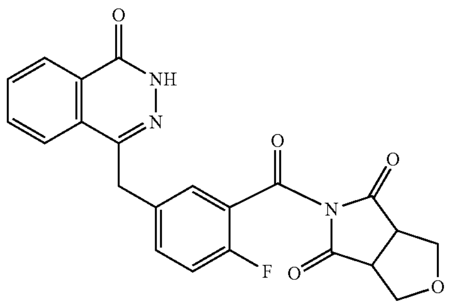 [SMILES: O=C(c1cc(Cc2n[nH]c(=O)c3ccccc23)ccc1F)N1C(=O)C2COCC2C1=O]

5-(cyclopropanecarbonyl)-2-(2-fluoro-5-((4-oxo-3,4-dihydrophthalazin-1-yl)methyl) benzoyl)pyrrolo[3,4-c]pyrrole-1,3(2H,5H)-dione

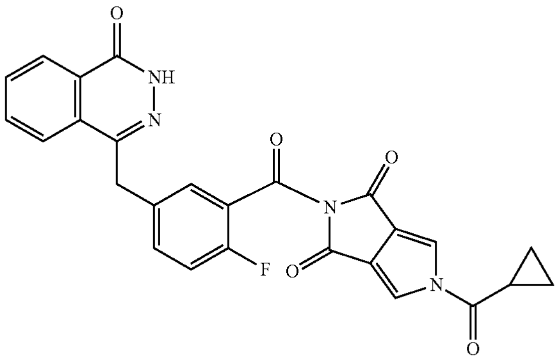 [SMILES: O=C(c1cc(Cc2n[nH]c(=O)c3ccccc23)ccc1F)N1C(=O)c2cn(C(=O)C3CC3)cc2C1=O]

4-(3-(5-benzyl-1,2,3,4,5,6-hexahydropyrrolo[3,4-c]pyrrole-2-carbonyl)-4-fluorobenzyl)phthalazin-1(2H)-one

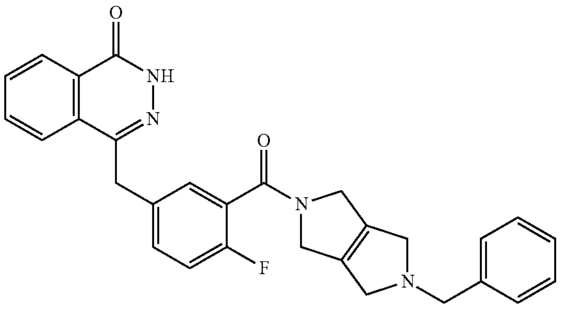 [SMILES: O=C(c1cc(Cc2n[nH]c(=O)c3ccccc23)ccc1F)N1CC2=C(CN(Cc3ccccc3)C2)C1]

5-(cyclopropylmethyl)-2-(2-fluoro-5-((4-oxo-3,4-dihydrophthalazin-1-yl)methyl)benzoyl)pyrrolo[3,4-c]pyrrole-1,3(2H,5H)-dione

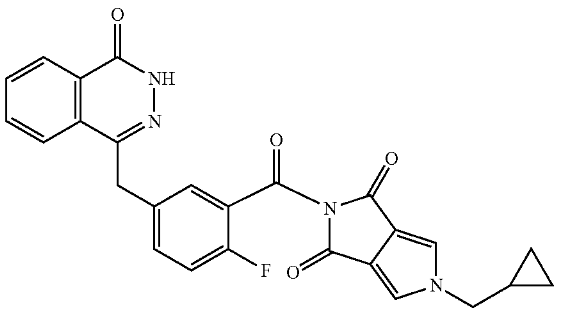 [SMILES: O=C(c1cc(Cc2n[nH]c(=O)c3ccccc23)ccc1F)N1C(=O)c2cn(CC3CC3)cc2C1=O]

4-(3-(5-(cyclopropanecarbonyl)-1,2,3,4,5,6-hexahydropyrrolo[3,4-c]pyrrole-2-carbonyl)-4-fluorobenzyl)phthalazin-1(2H)-one

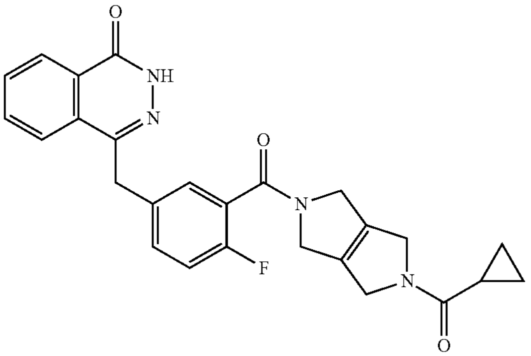 [SMILES: O=C(c1cc(Cc2n[nH]c(=O)c3ccccc23)ccc1F)N1CC2=C(C1)CN(C(=O)C1CC1)C2]

2-(cyclopropylmethyl)-5-(2-fluoro-5-((4-oxo-3,4-dihydrophthalazin-1-yl)methyl) benzoyl)tetrahydropyrrolo[3,4-c]pyrrole-1,3(2H,3aH)-dione

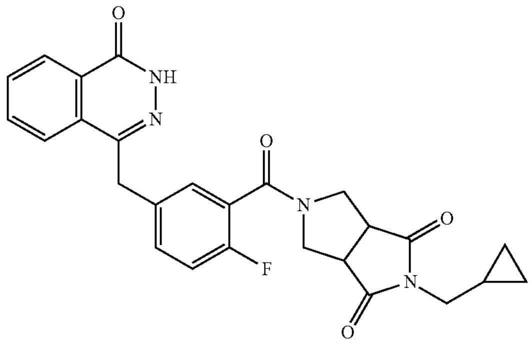 [SMILES: O=C(c1cc(Cc2n[nH]c(=O)c3ccccc23)ccc1F)N1CC2C(=O)N(CC3CC3)C(=O)C2C1]

Biological Activity—In vitro Study

In vitro Study

Potentiation of cell killing activity of Methyl Methane Sulphonate (MMS) by selected compounds according to present invention was evaluated in MCF-7 cell line obtained from National Centre for Cell Science, Pune, by using MTT assay according to general protocol described in *Methods in Molecular Biology*, Volume-43*, In vitro Toxicity Testing Protocol*, Chapter-6, page:137-149. Compounds were tested for PARP 1 activity based on percent cell survival of MCF-7 cells with alkylating agent MMS.

The compounds were tested for PARP-1 inhibitory activity by using HT universal colorimetric PARP assay kit obtained from Trevigen, following manufacturer's protocol.

The results of the compounds are provided in Table 1.

Result of Table 1 shows that the compounds are found to possess PARP 1 inhibitory activity, thus have potential to be developed as compounds for therapeutic use.

In vivo Study

On basis of the in vitro data, the ability of selected compounds to potentiate the antitumor activity of the methylating chemotherapeutic agent, temozolomide, was evaluated in an SW 620 tumor model.

Animals bearing SW 620 xenograft tumors were treated with the compounds in combination with TMZ (50 mg/Kg, po) once daily for 5 consecutive days, after which the tumors were left to grow out. A considerable inhibition of tumor volumes as compared with that of the TMZ alone group was observed for the TMZ plus compounds combinations (mean values given as relative tumor volumes (RTV) [table 2]. The compounds did not exacerbate the systemic toxicity of TMZ, with a maximum mean body weight loss of 9-10% on day 6 with full recovery of body weight within 3 days and with no mortalities, which indicates that the combination therapy was well tolerated by compounds under the dosing regimen.

Female athymic nude mice were used for antitumor in vivo studies. SW620 colorectal tumor cells ($1\times10^7$ cells per animal) were implanted s.c. into one flank of each mouse. When tumors were palpable (10-12 days after implantation), animals were treated (n=6-8/group) with five daily doses of temozolomide administered per os as a suspension in 0.5% methyl cellulose at 50 mg/kg either alone or in combination with a five daily per os administrations of PARP inhibitor at different doses. Tumor growths were measured using two-dimensional caliper measurements. Tumor volume was calculated using the equation $a^2 \times b/2$, where a is the smallest measurement and b is the largest. Data are presented as median relative tumor volumes (RTV), defined as the calculated tumor volume divided by the calculated tumor volume on the initial day of treatment (day 0). Thus, on day 0, the RTV value is 1 and RTV4 is when the tumor is four times as large as its initial value. Control animals were treated with vehicle (15 tween 80 in methyl cellulose) alone tumor growth delay (TGD)=Time to RTV4 in treated group−time to RTV4 control.

TABLE 1

In-Vitro PARP-1 activity

| Compound | PARP-1 activity in vitro IC50(nM)[a] |
|---|---|
| Olaparib | 8.39 ± 2.3 |
| Compound 1 | 11.54 |
| Compound 2 | 8.41 |
| Compound 3 | 14.55 |
| Compound 6 | 46.71 |
| Compound 7 | 38.63 |
| Compound 9 | 23.97 |
| Compound 12 | 14.15 |
| Compound 14 | 46.45 |
| Compound 15 | 11.64 |
| Compound 16 | 103.8 |
| Compound 17 | 30.27 |
| Compound 19 | 34.41 |
| Compound 20 | 11.78 |
| Compound 21 | 22.56 |
| Compound 22 | 20.22 |
| Compound 23 | 67.85 |
| Compound 24 | 9.85 |
| Compound 25 | 27.81 |
| Compound 26 | 35.95 |
| Compound 27 | 12.47 |
| Compound 28 | 20.73 |
| Compound 29 | 18.43 |
| Compound 30 | 9.87 |
| Compound 31 | 24.25 |
| Compound 32 | 11.54 |
| Compound 33 | 28.5 |
| Compound 34 | 11.68 |
| Compound 35 | 29.87 |
| Compound 36 | 27.87 |
| Compound 38 | 90.95 |
| Compound 39 | 54.52 |
| Compound 40 | 9.9 |
| Compound 41 | 8.9 |
| Compound 42 | 48.6 |
| Compound 43 | 55.1 |
| Compound 44 | 19.87 |
| Compound 45 | 13.8 |
| Compound 46 | 27.8 |
| Compound 47 | 48.3 |
| Compound 48 | 74.5 |
| Compound 54 | 15.4 |
| Compound 55 | 13.23 |

[a]PARP 1 $IC_{50}$ are estimation as calculated from a 4 point dose response curve

TABLE 2

In vivo antitumor efficacy of compounds in combination with temozolomide (TMZ) in an SW620 tumor model [b].

| Compounds | Median time to RTV4(days) | Tumor growth delay(days) |
|---|---|---|
| Vehicle(control) | 10 | |
| Temozolomide (50 mg/kg, po) | 22 | 12 |
| TMZ (50 mg/kg, po) + example 20 (50 mg/kg, po) | 43 | 33 |
| TMZ (50 mg/kg, po) + example 35 (10 mg/kg, po) | 50 | 40 |

TABLE 2-continued

In vivo antitumor efficacy of compounds in combination with temozolomide (TMZ) in an SW620 tumor model [b].

| Compounds | Median time to RTV4(days) | Tumor growth delay(days) |
|---|---|---|
| TMZ (50 mg/kg, po) + example 36 (10 mg/kg, po) | 37 | 27 |
| TMZ (50 mg/kg, po) + example 36 (30 mg/kg, po) | 44 | 34 |
| TMZ (50 mg/kg, po) + example 36 (100 mg/kg, po) | 65 | 55 |

[b] Mice were orally dosed once daily for 5 consecutive days. The compounds were administered 45 min before TMZ.

We claim:

1. Compound having the structure of general formula (I)

(I)

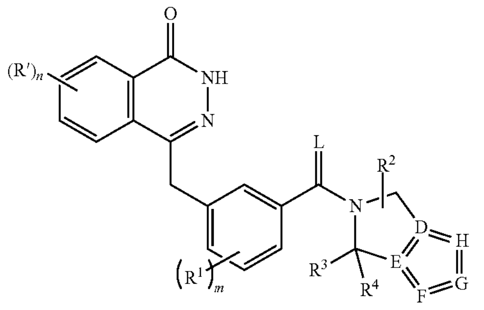

wherein $R^1$ at each occurrence is independently selected from hydrogen, halogen, or the groups selected from $(C_1$-$C_6)$alkyl, haloalkyl, $(C_3$-$C_6)$cycloalkyl, alkylthio or the group $(OSO_2)$alkyl;

R' at each occurrence is independently selected from hydrogen, halogen, $(C_1$-$C_6)$alkyl, $(C_1$-$C_6)$alkoxy, hydroxyl, haloalkyl, haloalkoxy, cyano, thioalkyl, $(C_3$-$C_6)$cycloalkyl groups;

m=1-4;

L=—O, —S, —NH;

n=0-4

$R^2$ is selected from hydrogen atom, hydroxyl, $(C_1$-$C_6)$ alkyl, $(C_3$-$C_6)$cycloalkyl, oxo, $C(O)OR^5$, —$C(O)R^5$, or —$C(O)NR^6R^7$, wherein said $(C_1$-$C_6)$alkyl and $(C_3$-$C_6)$ cycloalkyl groups are further substituted by one or more substituents selected from halogen, hydroxyl, $(C_1$-$C_6)$alkyl or $(C_1$-$C_6)$alkoxy groups;

$R^3$ and $R^4$ are each independently selected from hydrogen atom, $(C_1$-$C_6)$alkyl, hydroxyl, $(C_1$-$C_6)$alkoxy, $(C_3$-$C_6)$ cycloalkyl, —$C(O)OR^5$, —$OC(O)R^5$, —$O(CH_2)_pC(O)OR^5$, —$C(O)R^5$, —$NHC(O)R^5$, —$NR^6R^7$, —$OC(O)NR^6R^7$ or —$C(O)NR^6R^7$ or alternatively, $R^3$ and $R^4$ together forms an oxo group;

each of the ring atoms 'D' and 'E' is independently selected from C or N atoms;

each of the ring atoms 'F', 'G' and 'H' is independently selected from C, N, O and S atoms the ring formed by 'D', 'E', 'F', 'G' and 'H' represents a substituted or non-substituted five-membered bicyclic aromatic or non-aromatic heterocyclic ring;

$R^5$ at each occurrence is independently selected from hydrogen atom, optionally substituted groups selected from $(C_1$-$C_6)$alkyl, $(C_3$-$C_6)$cycloalkyl, $(C_6$-$C_{10})$heterocyclyl, $(C_6$-$C_{10})$aryl or $(C_6$-$C_{10})$heteroaryl groups;

each of $R^6$ or $R^7$ at each occurrence are independently selected from $(C_6-C_{10})$heterocyclyl, $(C_6-C_{10})$aryl or $(C_6-C_{10})$heteroaryl, optionally $R^6$ and $R^7$ are joined together with nitrogen atom to form a $(C_6-C_{10})$heterocyclyl ring; wherein said heterocyclyl and heteroaryl ring contains one or more heteroatoms selected from N, O, $S(O)_n$, n is 0, 1 or 2 and p is 0, 1 or 2.

2. The compound as claimed in claim 1, wherein heterocycles representing

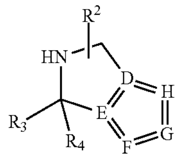

are selected from a member of the group consisting of

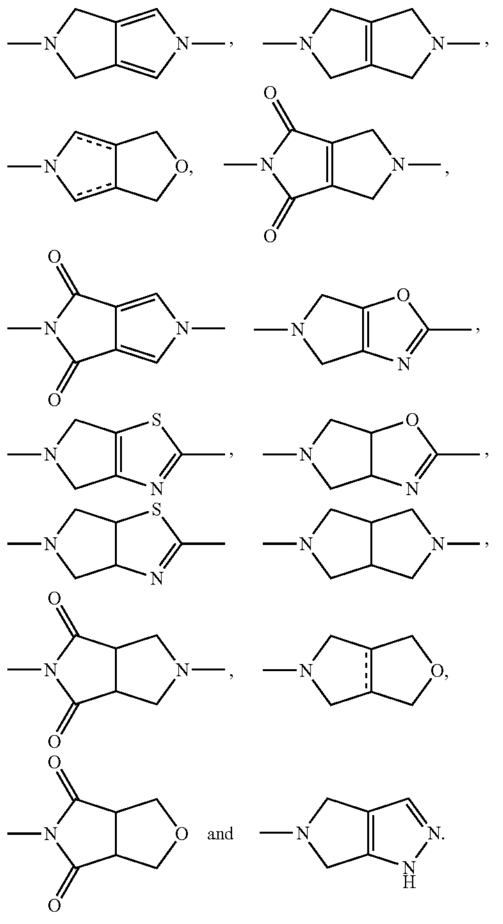

3. The compound as claimed in claim 1, wherein the substituents on $R^1$ is selected from hydroxyl, oxo, halo, thio, nitro, amino, $(C_1-C_6)$alkyl, $(C_1-C_6)$alkoxy, haloalkyl or haloalkoxy groups alone or in combination with other radicals.

4. The compound as claimed in claim 1 wherein the substituents on $R^5$ is selected from $(C_1-C_6)$alkyl, halogen, hydroxyl, $(C_1-C_6)$alkoxy, $(C_3-C_6)$cycloalkyl, $(C_6-C_{10})$ heterocyclyl, $(C_6-C_{10})$aryl, $(C_6-C_{10})$heteroaryl, carboxylic acid or carboxylic acid ester substituents.

5. The compound as claimed in claim 1 wherein the substituents on $R^6$ & $R^7$ at each occurrence is independently selected from $(C_1-C_6)$alkyl, halogen, hydroxyl, $(C_1-C_6)$ alkoxy, $(C_3-C_6)$cycloalkyl, $(C_6-C_{10})$heterocyclyl, $(C_6-C_{10})$ aryl, $(C_6-C_{10})$heteroaryl, carboxylic acid or carboxylic acid ester substituents.

6. The compound as claimed in claim 1, wherein the substituents on substituted or non-substituted bicyclic aromatic or non-aromatic five membered heterocyclic ring is selected from halogen, hydroxyl, oxo, optionally substituted groups selected from $(C_1-C_6)$alkyl, $(C_1-C_6)$alkoxy, $(C_3-C_6)$ cycloalkyl, $(C_6-C_{10})$heterocyclyl, $(C_6-C_{10})$aryl, $(C_6-C_{10})$ heteroaryl, benzyl, $OR^5$, $—C(O)OR^5$, $—OC(O)R^5$, $—O(CH_2)_pC(O)OR^5$, $C(O)R^5$, $S(O)_nR^5$, $—NHC(O)R^5$, $NR^6R^7$, $—OC(O)NR^6R^7$ or $—C(ONR^6R^7$, wherein each of $R^5$, $R^6$ & $R^7$ are as defined in claim 1 and wherein the $(C_1-C_6)$alkyl, $(C_3-C_6)$cycloalkyl, $(C_6-C_{10})$heterocyclyl, $(C_6-C_{10})$aryl, $(C_6-C_{10})$heteroaryl or benzyl group are each independently substituted further with one or more substituents selected from $(C_1-C_6)$alkyl, halogen, hydroxyl, $(C_1-C_6)$ alkoxy, $(C_3-C_6)$cycloalkyl, $(C_6-C_{10})$heterocyclyl, $(C_6-C_{10})$ aryl, $(C_6-C_{10})$heteroaryl, oxo, $—C(O)OR^5$, $—OC(O)R^5$, $O(CH_2)_pC(O)OR^5$, $—C(O)R^5$, $—S(O)nR^5$, $—NHC(O)R^5$, $NR^6R^7$, $—OC(O)NR^6R^7$ or $—C(O)NR^6R^7$ groups.

7. The compound as claimed in claim 1, wherein aryl groups are selected from a member of the group consisting of phenyl, naphthyl, tetrahydronaphthyl, indenyl, dihydroindenyl, and biphenyl.

8. The compound as claimed in claim 1, wherein the substituents on aryl groups are independently selected from hydrogen, halogen, $(C_1-C_6)$alkyl, $(C_1-C_6)$alkoxy, hydroxyl, haloalkyl, haloalkoxy, cyano, thioalkyl, $(C_3-C_6)$cycloalkyl groups.

9. The compound as claimed in claim 1, wherein the heteroaryl or heteroaromatic group is selected from pyridyl, thienyl, furyl, pyrrolyl, indolinyl, indolyl, pyridofuranyl, pyridothienyl, thienopyrimidyl, quinolinyl, pyrimidinyl, pyrazolyl, quinazolinyl, pyridazinyl, purinyl groups.

10. The compound as claimed in claim 1, where in the substitution on heteroaryl or heteroaromatic group is selected from hydrogen, halogen, $(C_1-C_6)$alkyl, $(C_1-C_6)$ alkoxy, hydroxyl, haloalkyl, haloalkoxy, $(C_6-C_{10})$aryl, aralkyl, cyano, alkylthio, thioalkyl groups.

11. The compound as claimed in claim 1, wherein the heterocyclyl group is selected from aziridinyl, azetidinyl, pyrrolidinyl, imidazolidinyl, piperidinyl, piperazinyl, 2-oxopiperidinyl, 4-oxopiperidinyl, 2-oxopiperazinyl, 3-oxopiperazinyl, morpholinyl, thiomorpholinyl, 2-oxomorpholinyl, azepinyl, diazepinyl, oxapinyl, thiazepinyl, oxazolidinyl, thiazolidinyl, dihydrothiophene, dihydropyran, dihydrofuran, dihydrothiazole, benzopyranyl, benzopyranonyl, benzodihydrofuranyl, benzodihydrothienyl, pyrazolopyrimidonyl, azaquinazolinoyl, thienopyrimidonyl, quinazolonyl, pyrimidonyl, benzoxazinyl, benzoxazinonyl, benzothiazinyl, benzothiazinonyl, thienopiperidinyl, groups.

12. The compound as claimed in claim 1, wherein the substituents on heterocyclyl group is selected from hydrogen, halogen, $(C_1-C_6)$alkyl, $(C_1-C_6)$alkoxy, hydroxyl, haloalkyl, haloalkoxy, $(C_6-C_{10})$aryl, aralkyl, cyano, alkylthio, thioalkyl groups.

13. The compound as claimed in claim 1 selected from a member of the group consisting of:

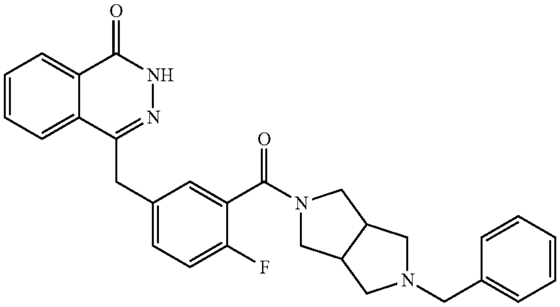,
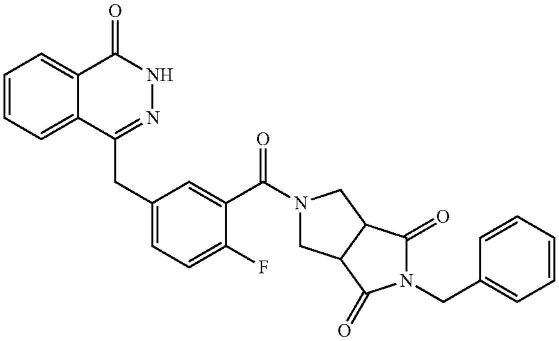,
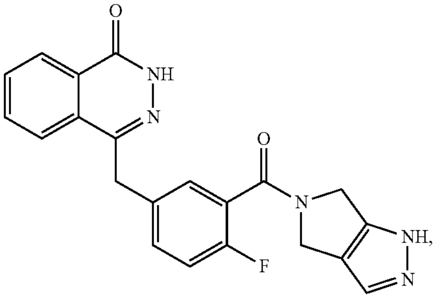
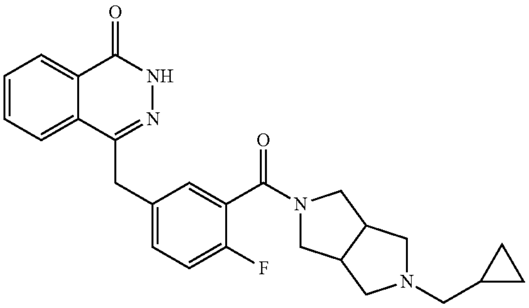,
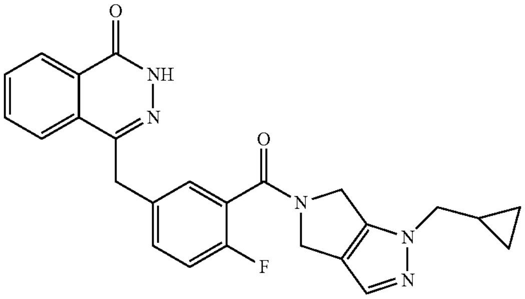,
-continued
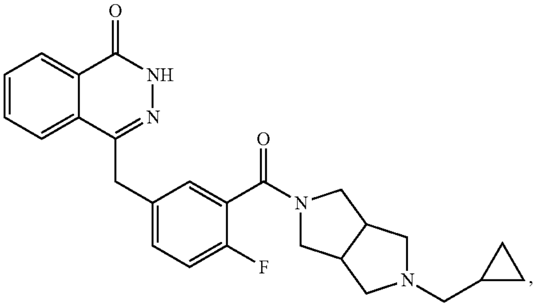,
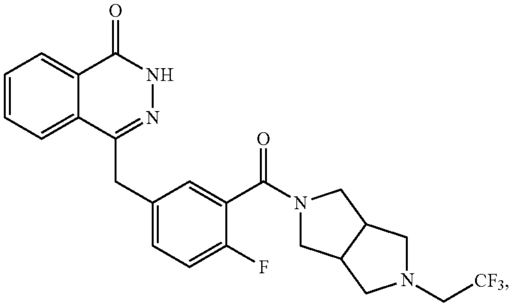
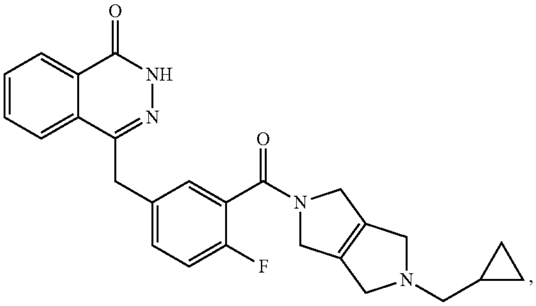,
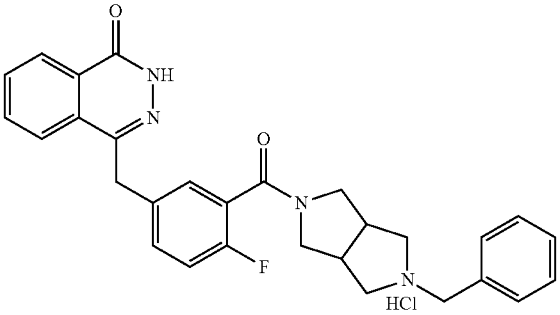,
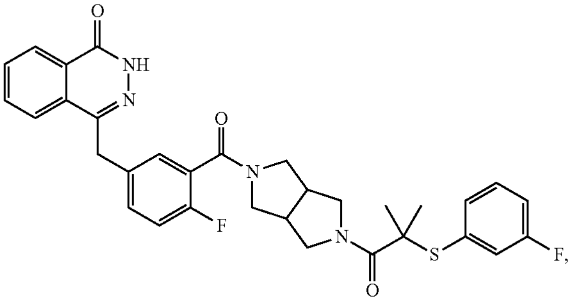

-continued
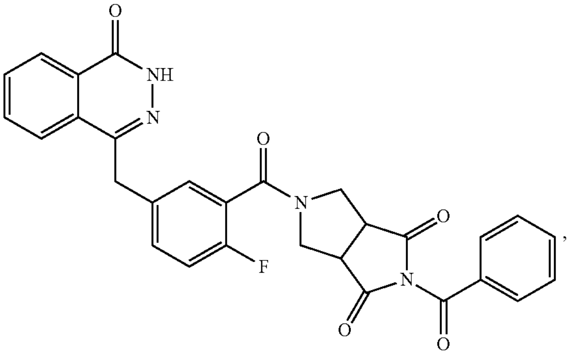
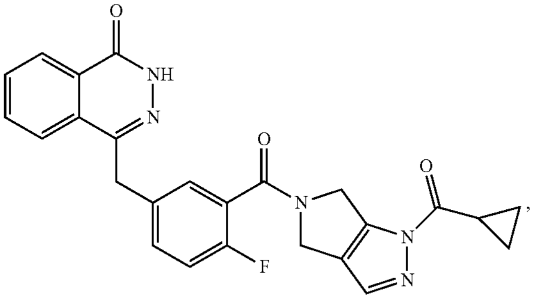
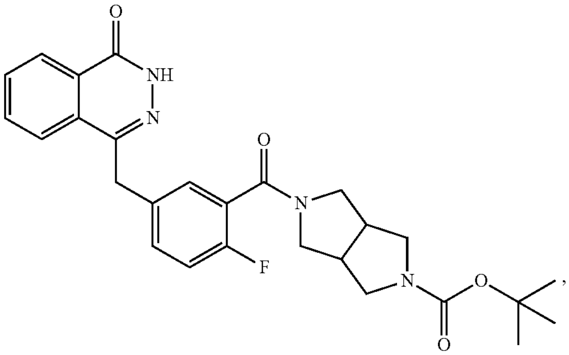
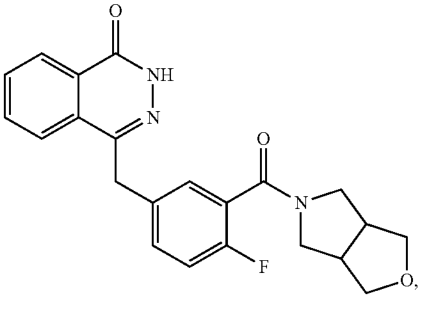
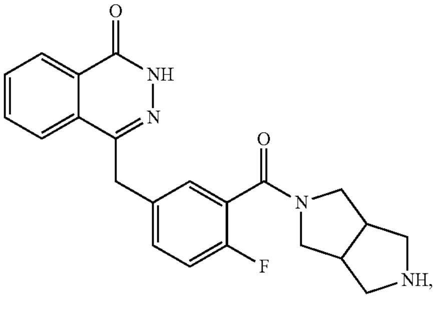
-continued
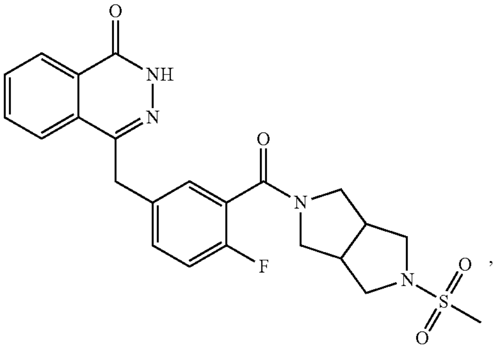
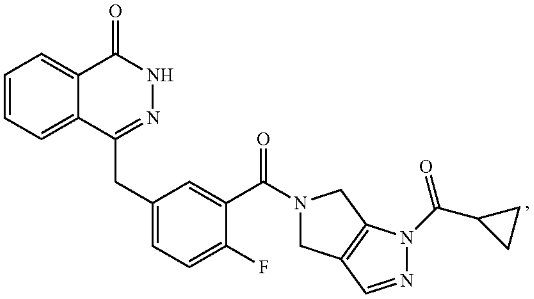
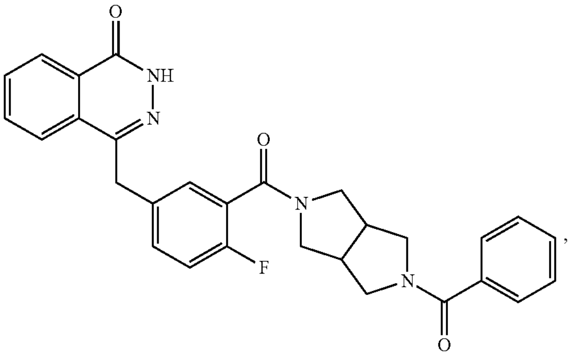
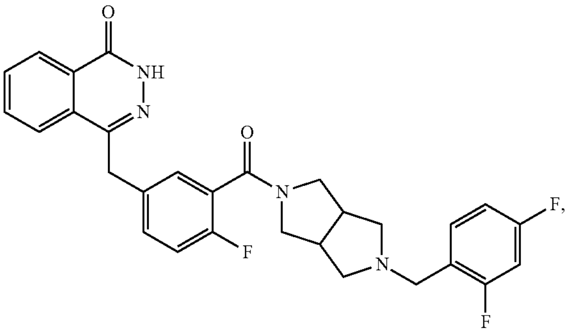
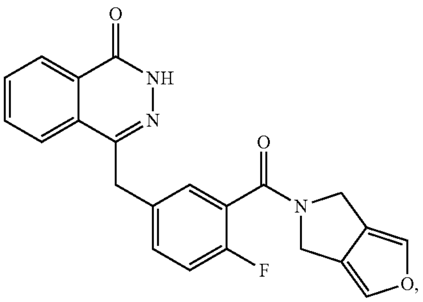

-continued
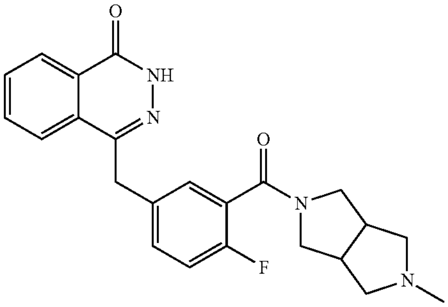
,
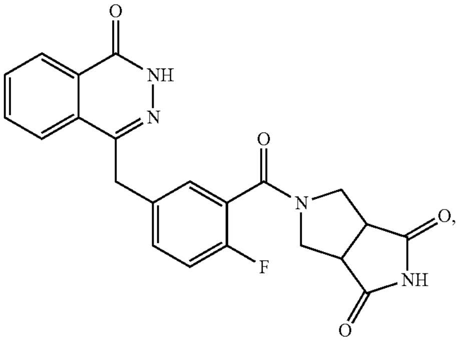
,
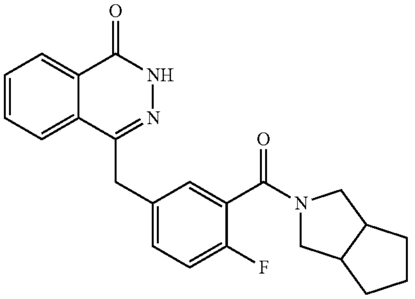
,
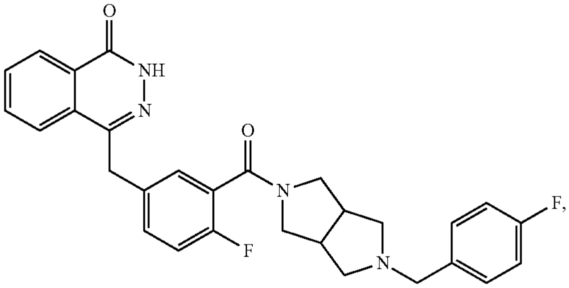
,
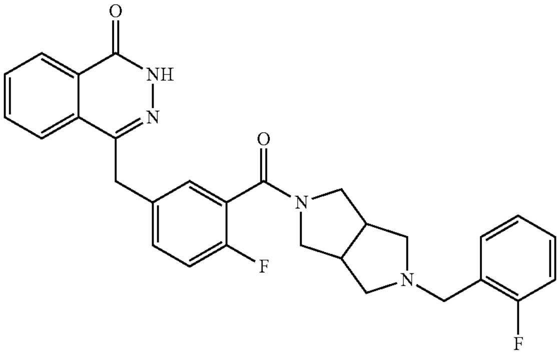
,
-continued
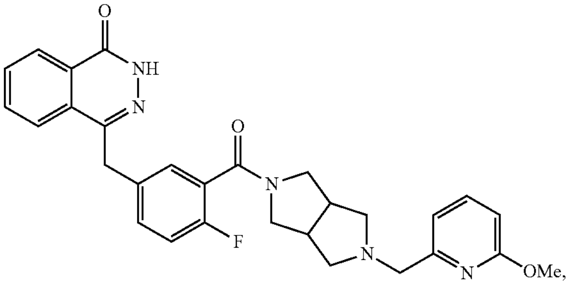
,
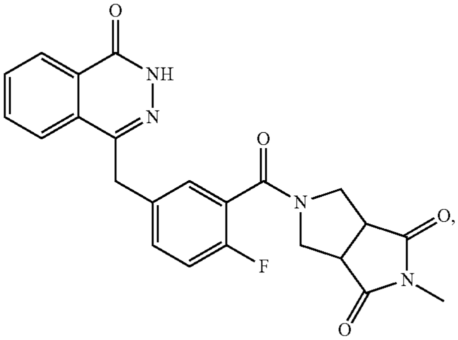
,
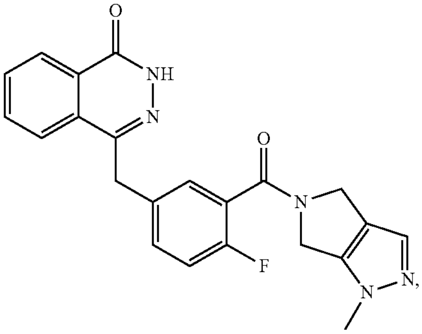
,
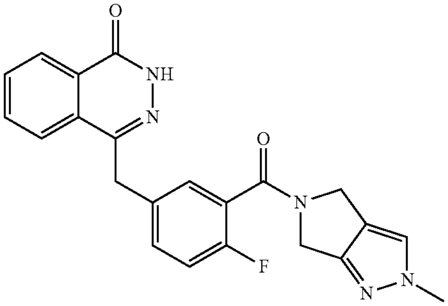
,
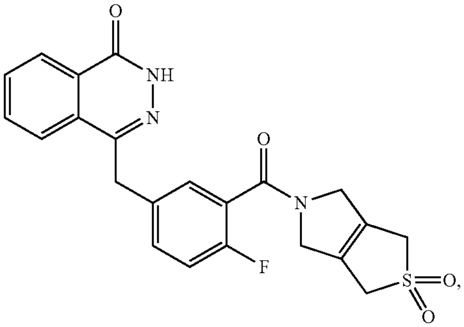
, -continued
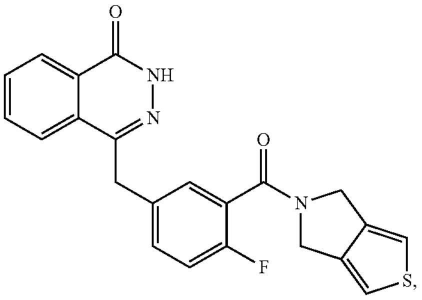
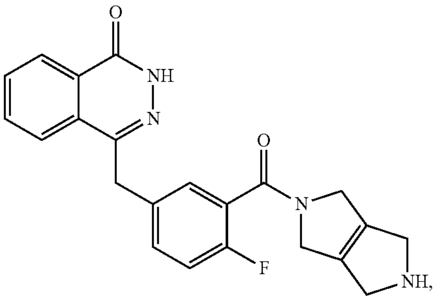
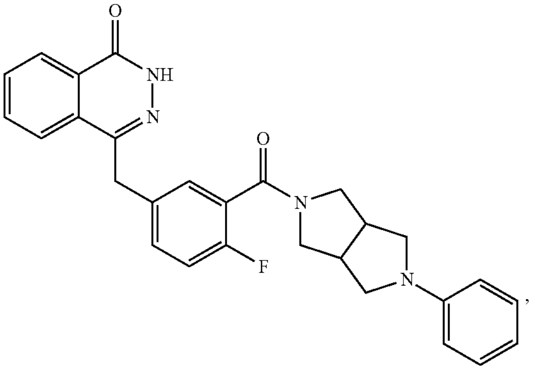
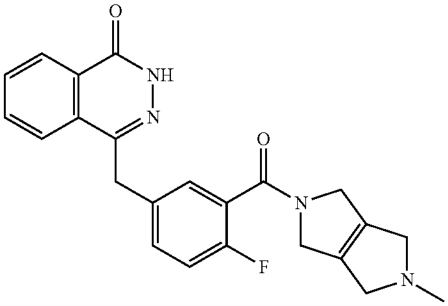
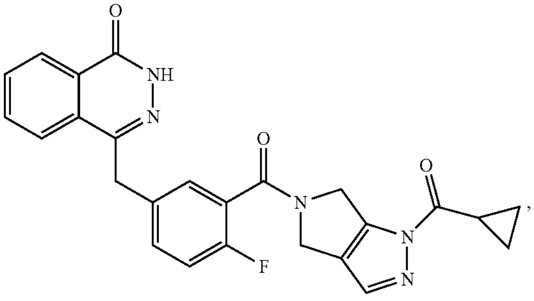
-continued
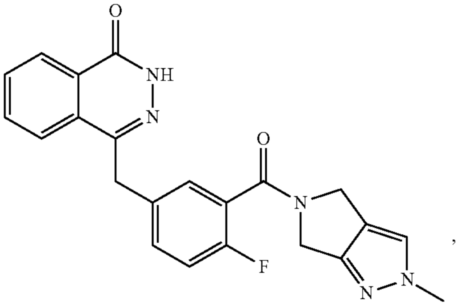
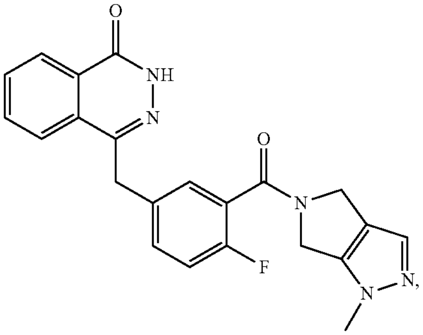
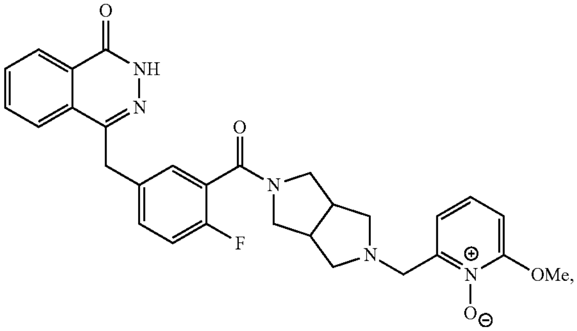
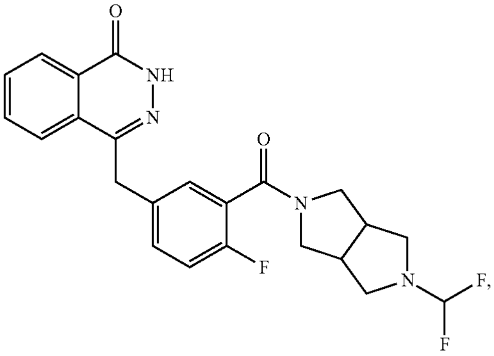
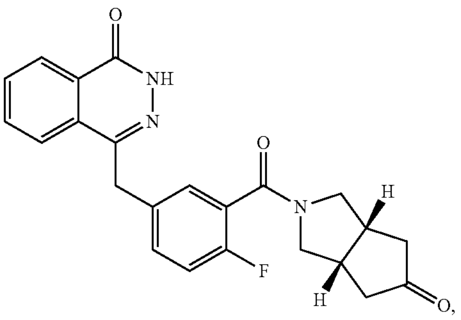

-continued
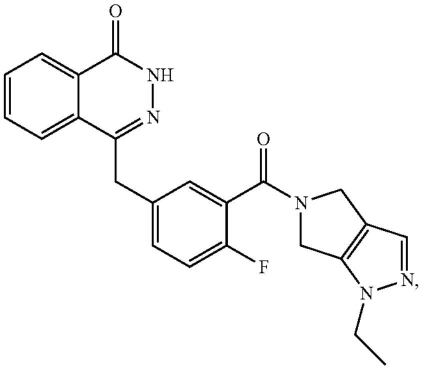
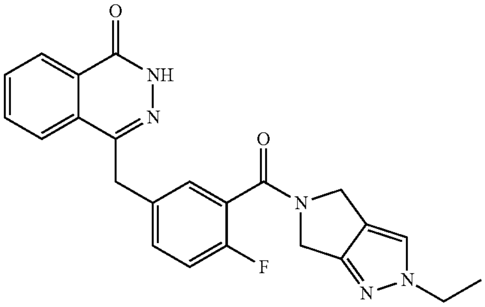
,
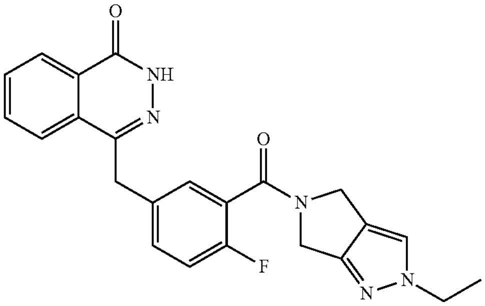
,
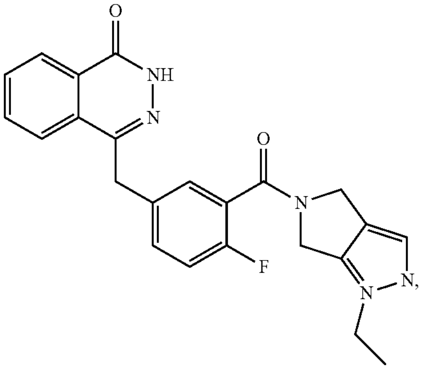
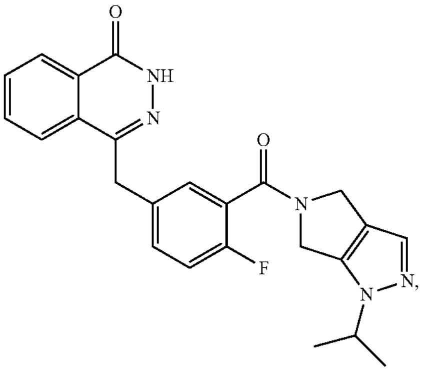
-continued
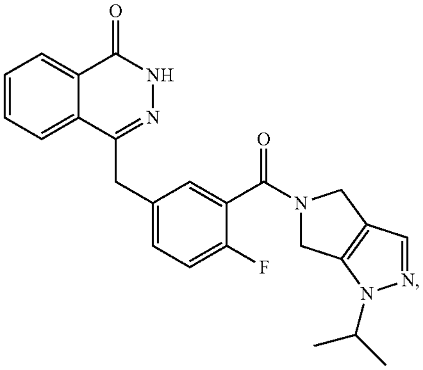
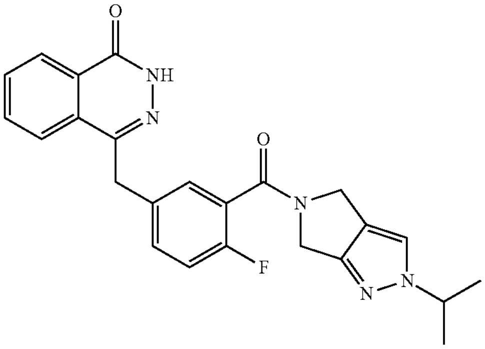
,
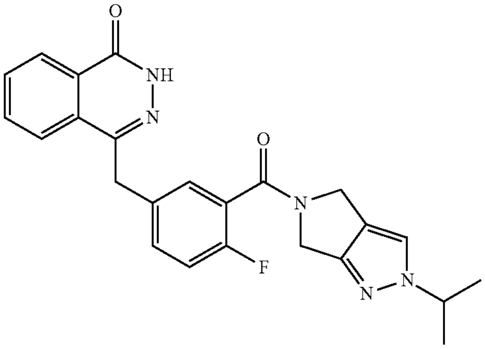
,
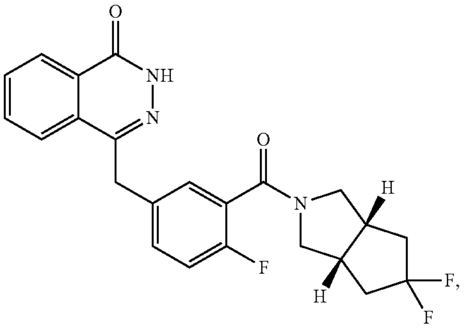
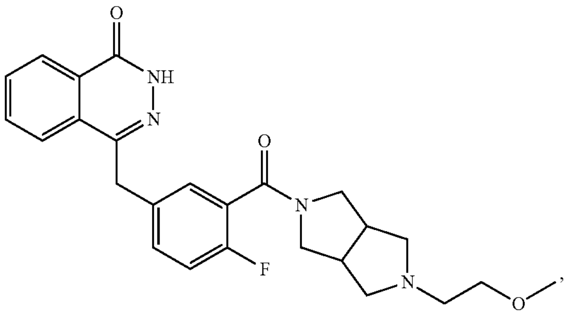

-continued
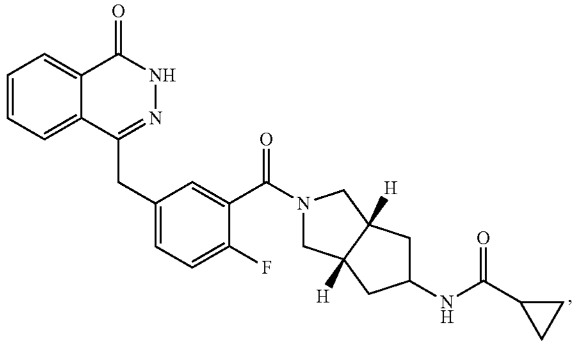
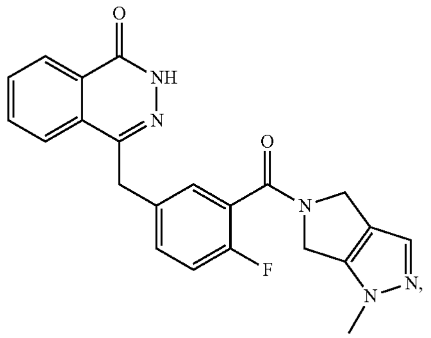
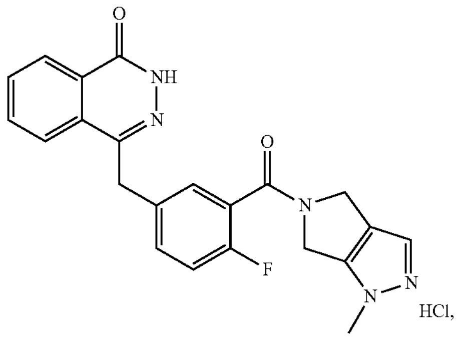
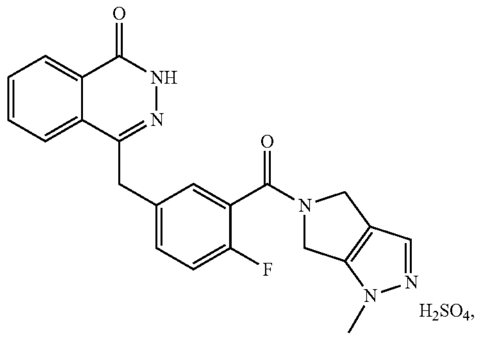
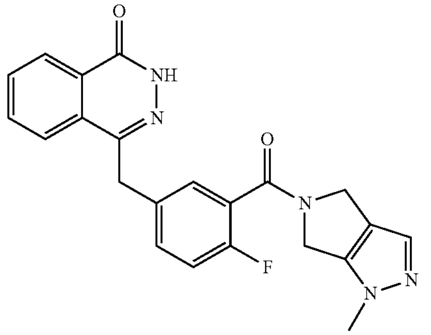
-continued
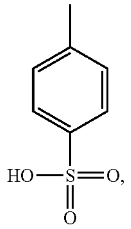
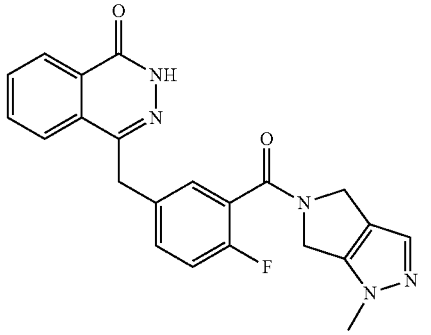
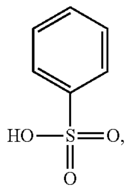
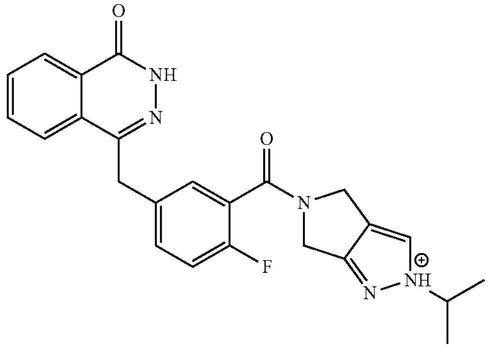
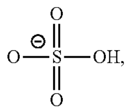
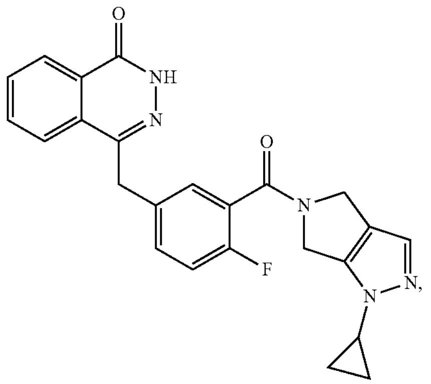

-continued
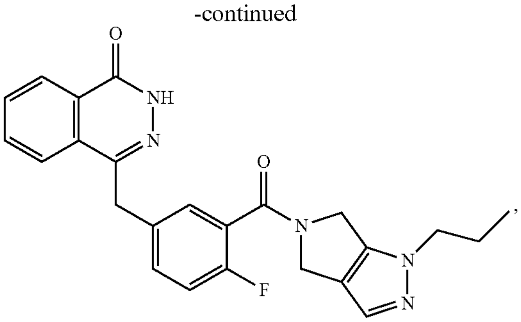,
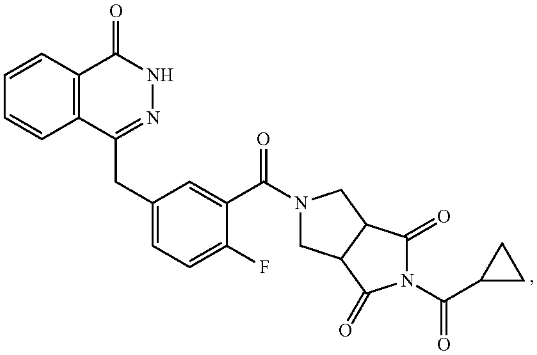,
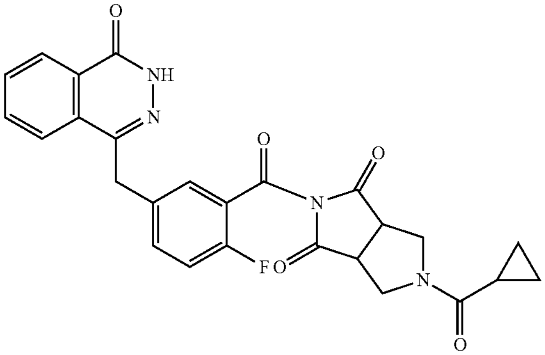,
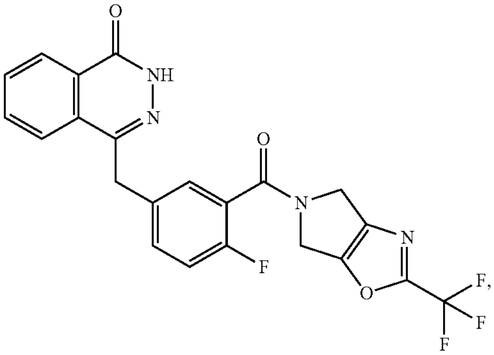,
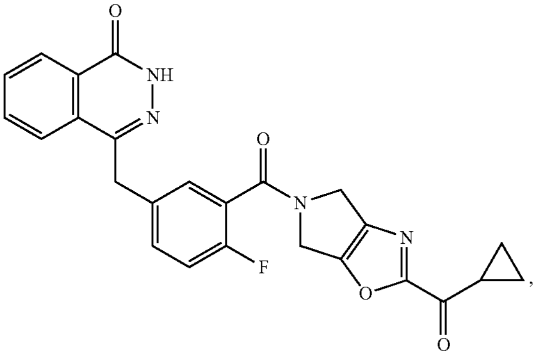,
-continued
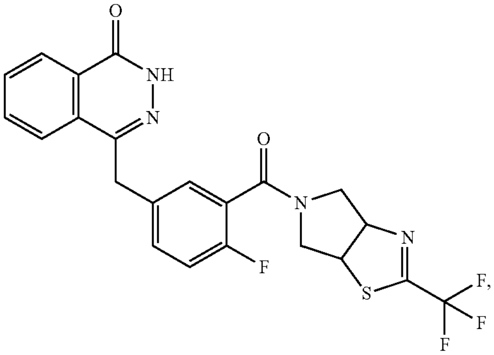,
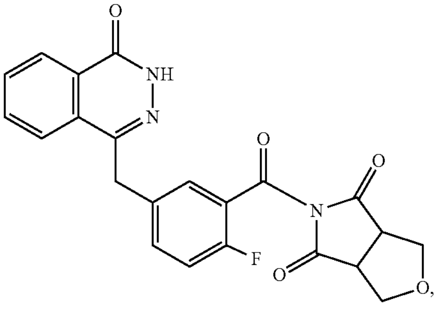,
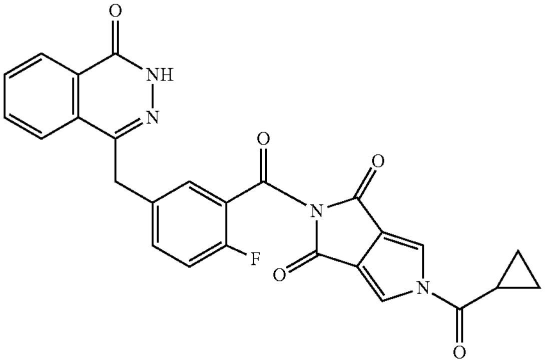,
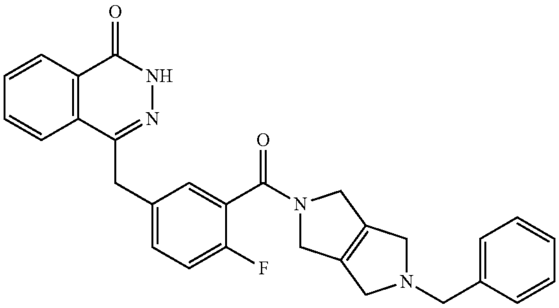,
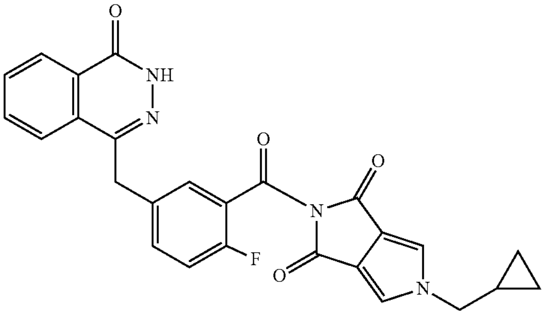, -continued
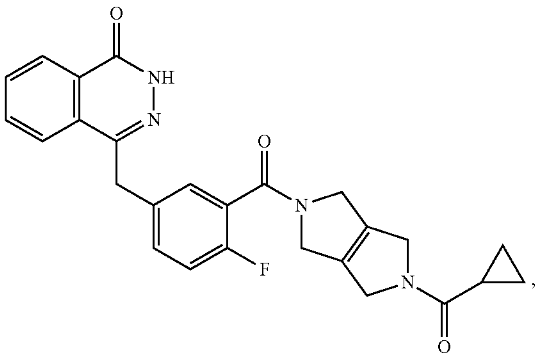,
and
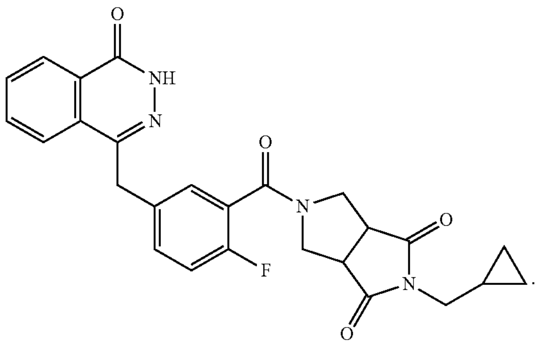.
14. The compound as claimed in claim 1 selected from a member of the group consisting of:
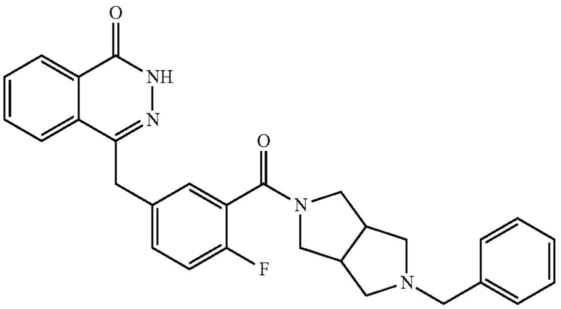,
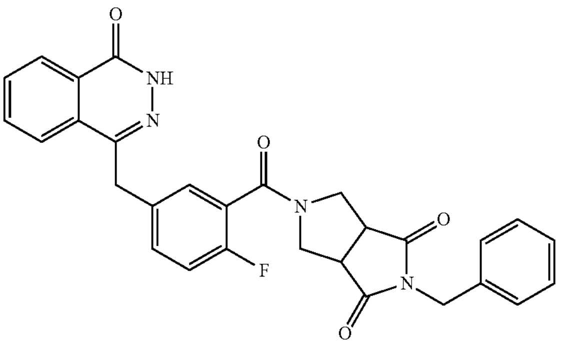,
-continued
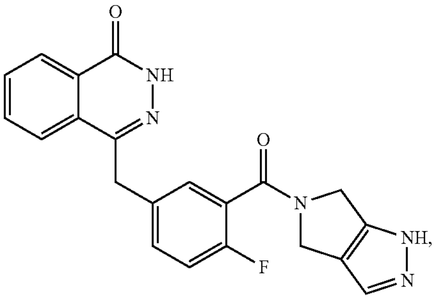,
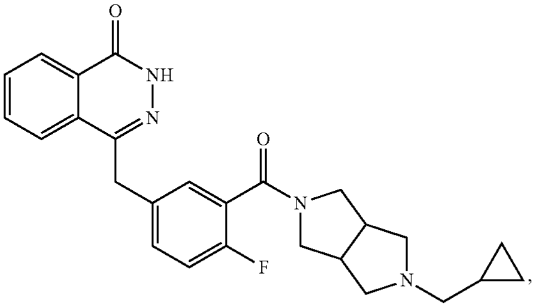,
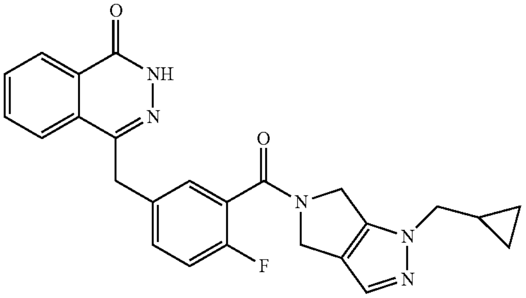,
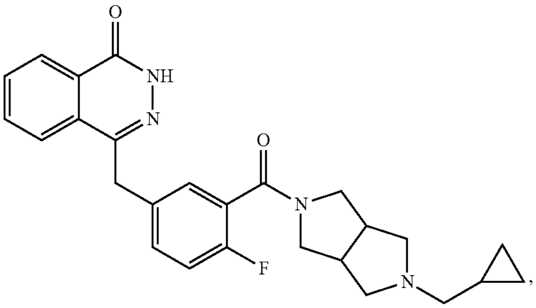,
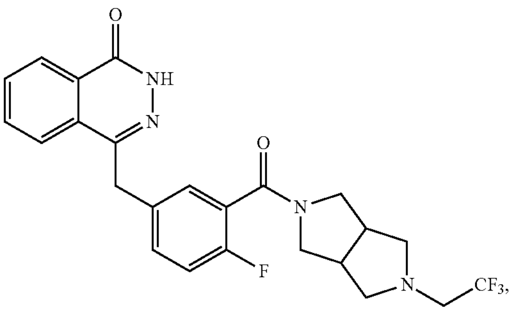, -continued
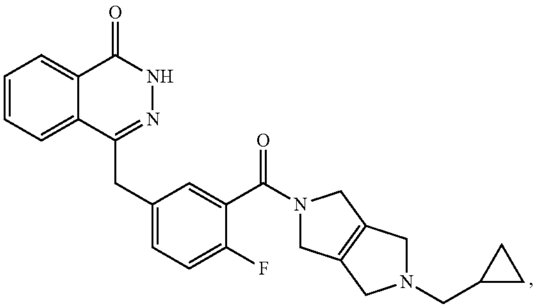
,
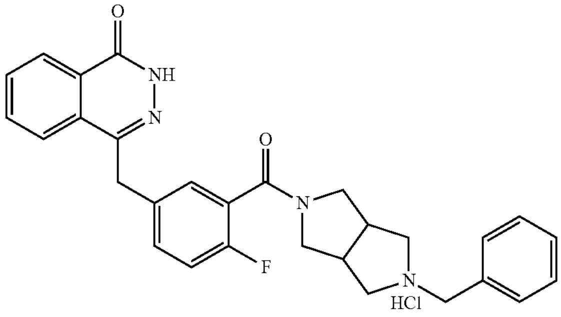
,
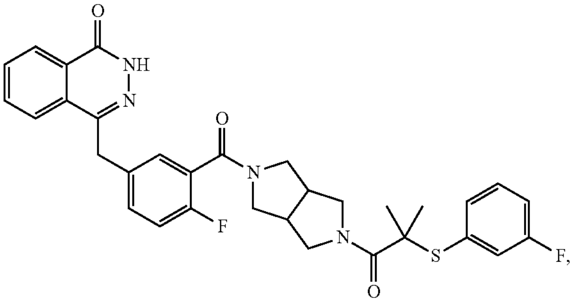
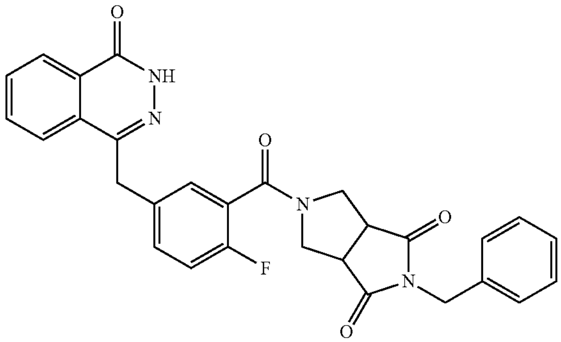
,
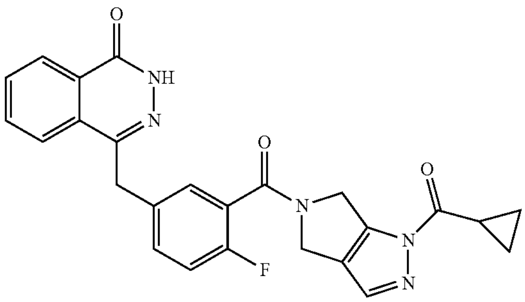
,
-continued
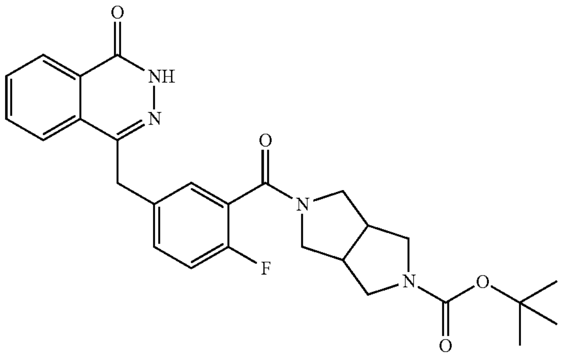
,
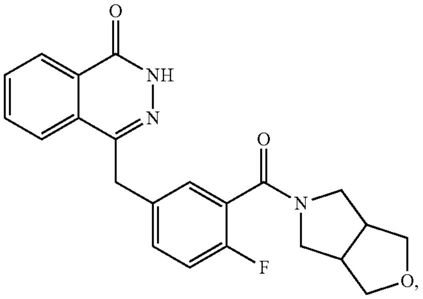
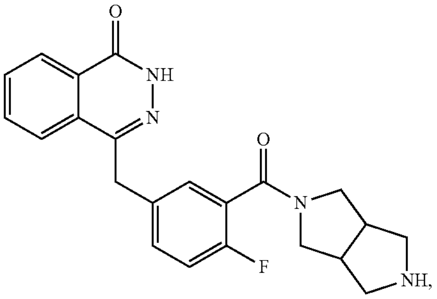
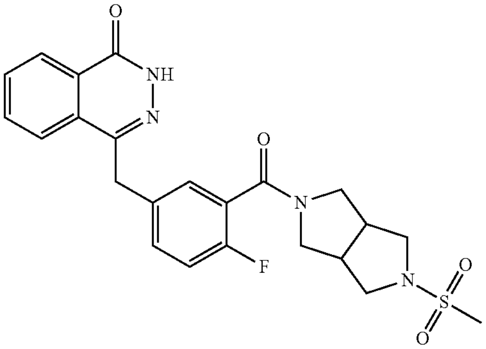
,
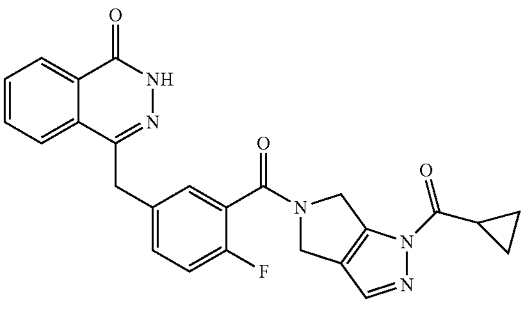
, -continued
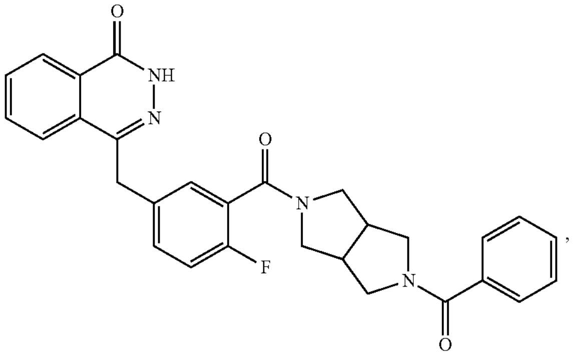
,
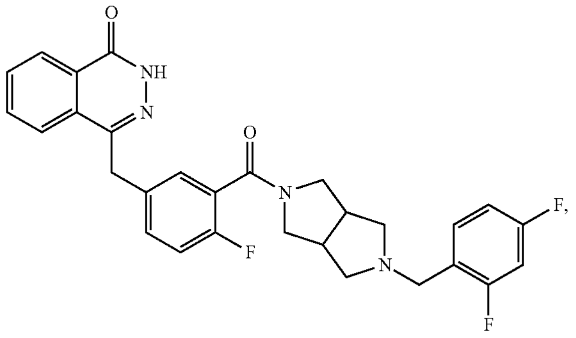
,
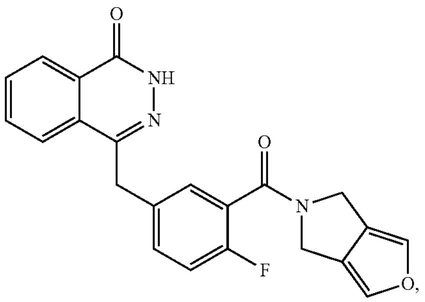
,
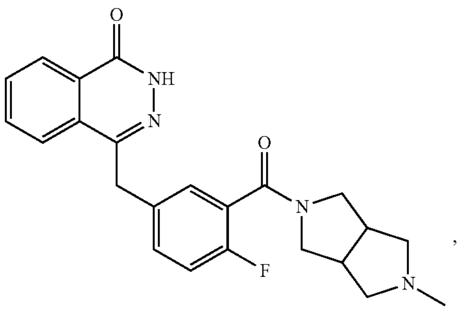
,
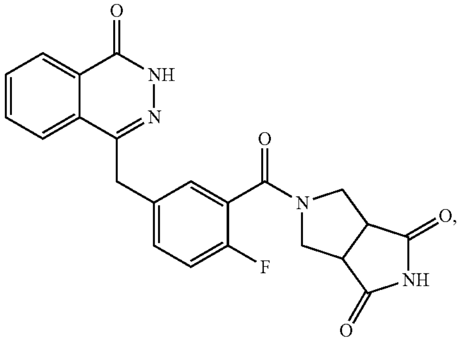
,
-continued
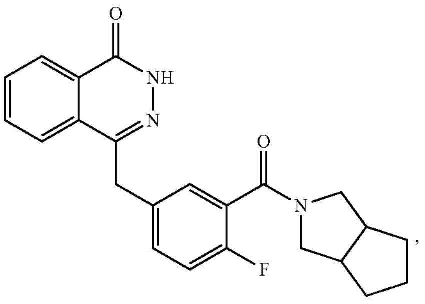
,
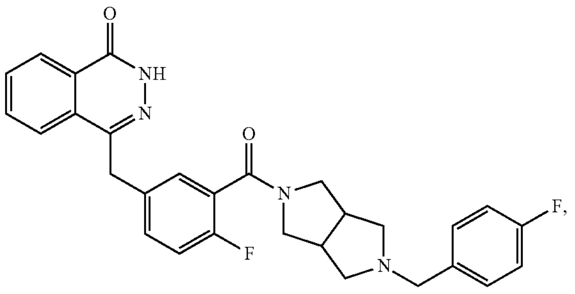
,
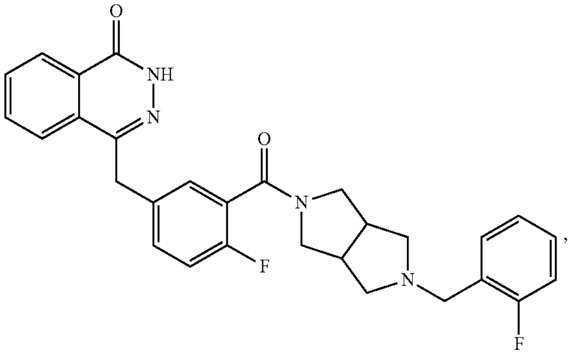
,
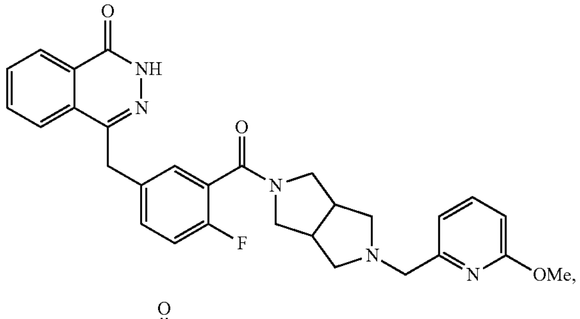
,
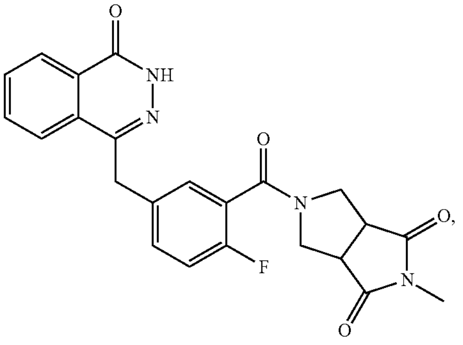
, -continued
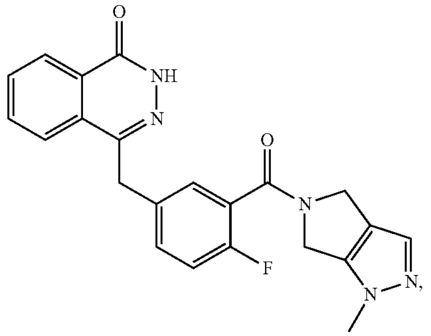
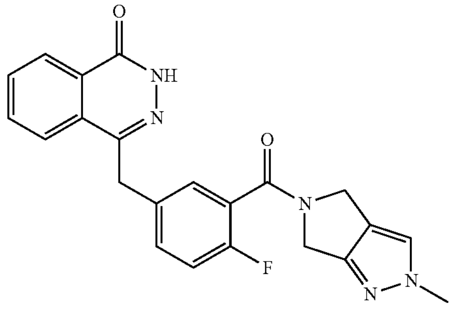
,
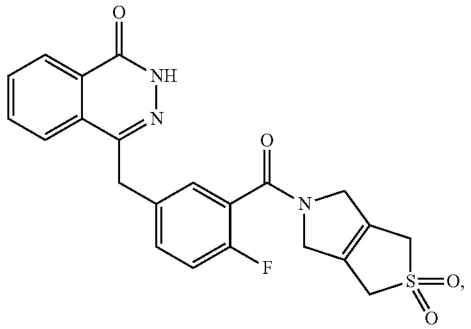
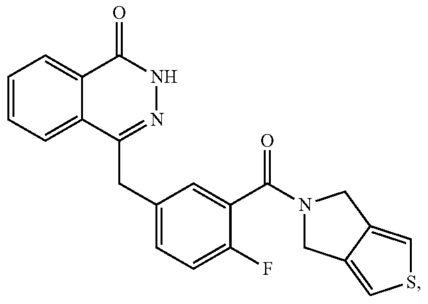
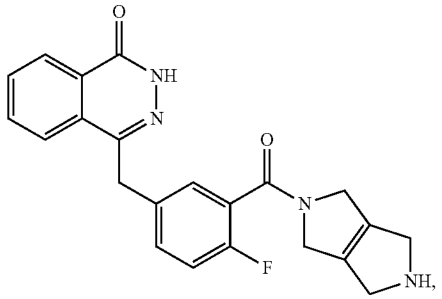
-continued
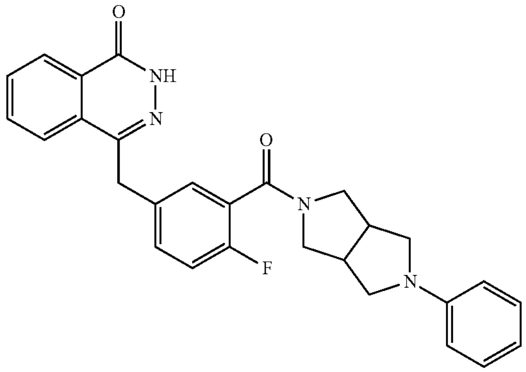
,
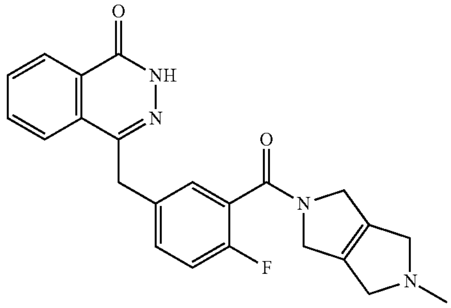
,
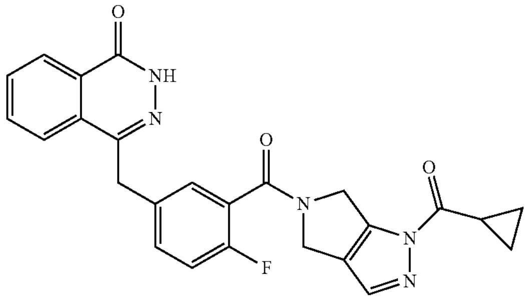
,
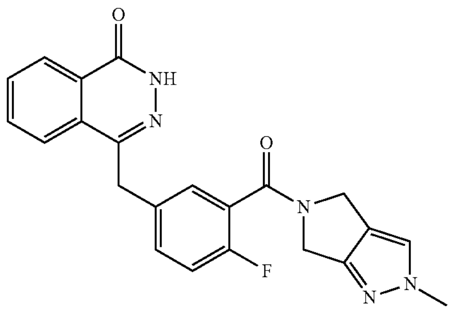
,
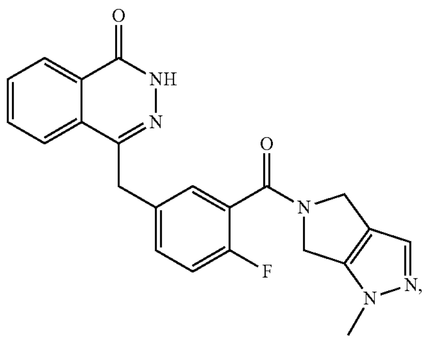

-continued
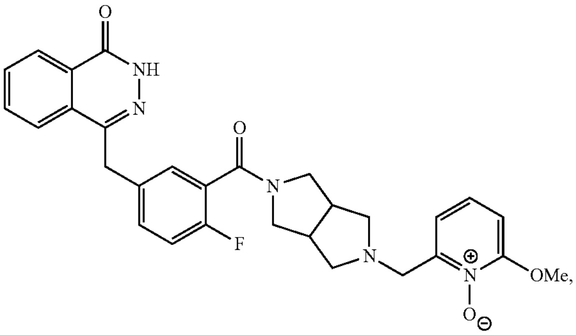,
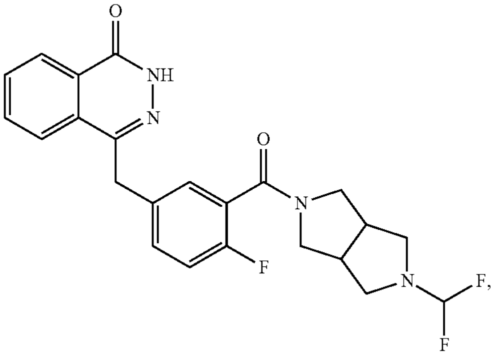,
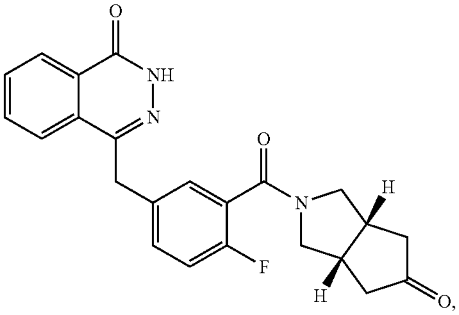,
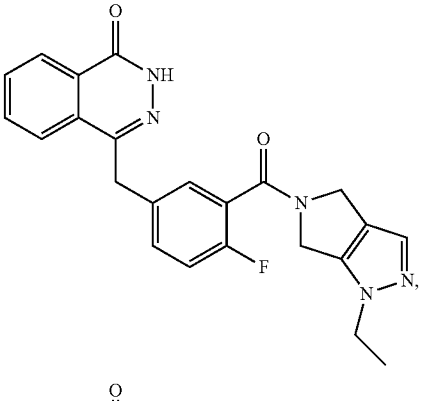,
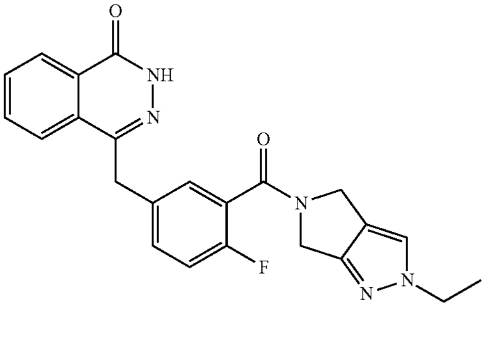,
-continued
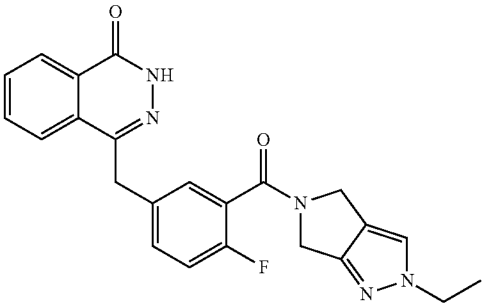,
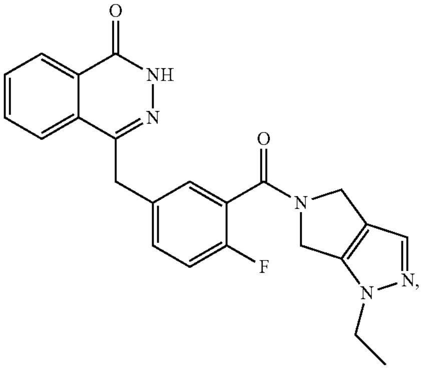,
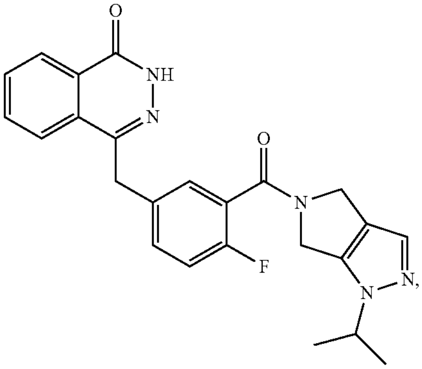,
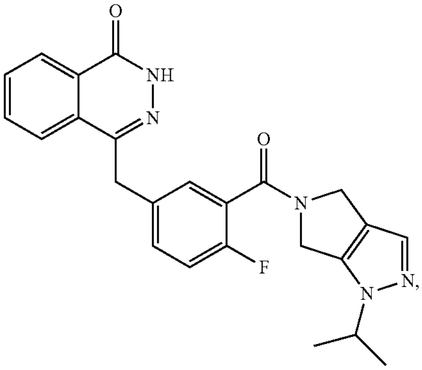, -continued
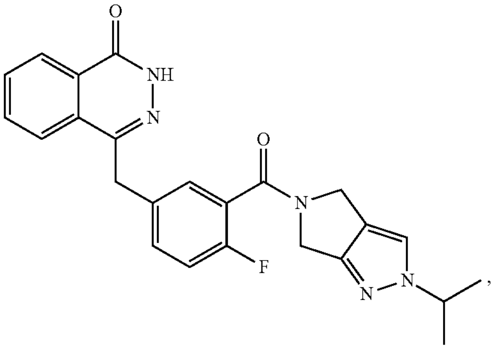
,
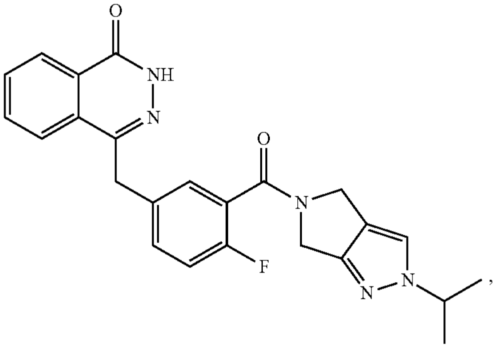
,
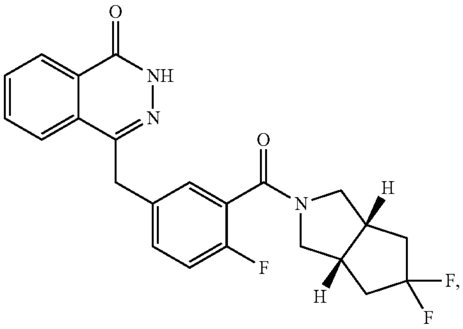
,
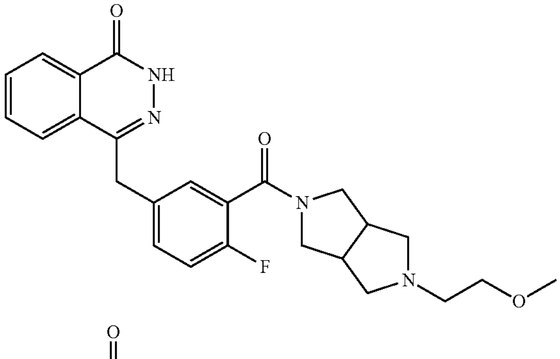
,
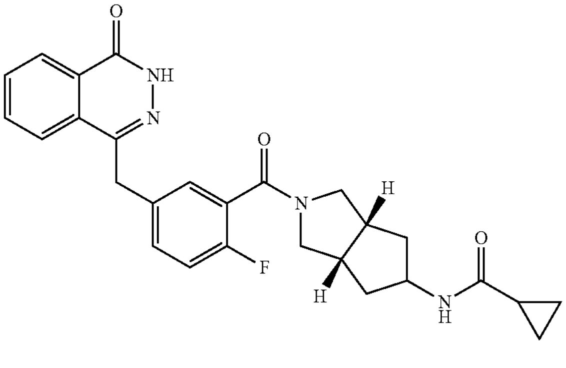
,
-continued
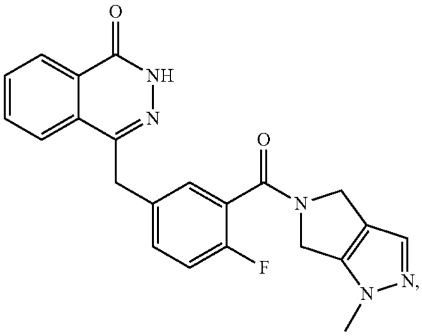
,
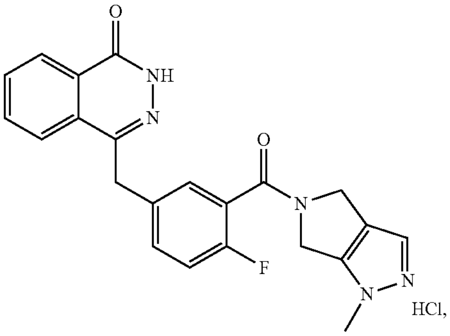
$HCl$,
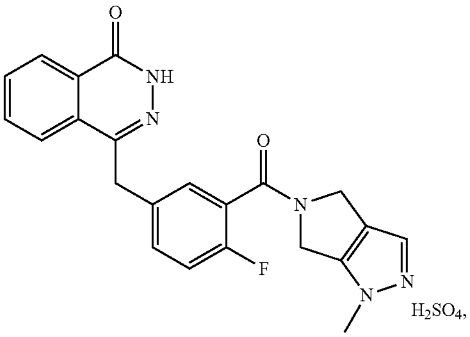
$H_2SO_4$,
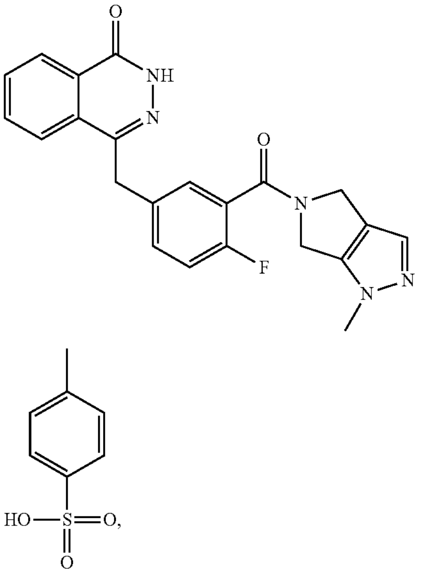
, -continued
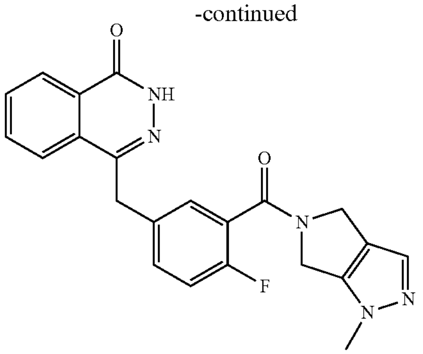
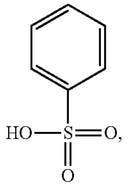
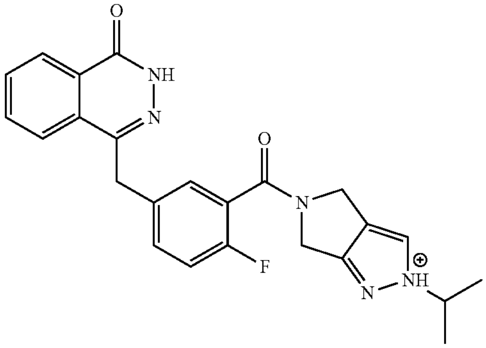
-continued
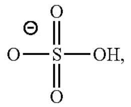
and
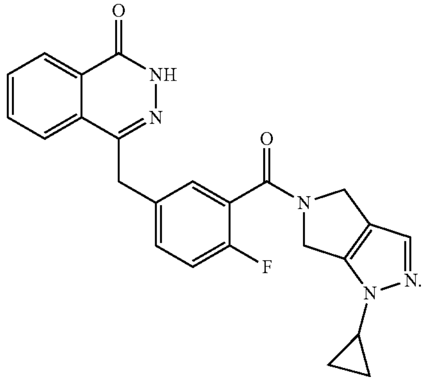
15. A pharmaceutical composition comprising a therapeutically effective amount of a compound of Formula (I) as claimed in claim 1 and optionally one or more pharmaceutically acceptable carriers, diluents or excipients.
* * * * *